(12) United States Patent
Shibley et al.

(10) Patent No.: US 11,134,929 B2
(45) Date of Patent: Oct. 5, 2021

(54) PNEUMOPERITONEUM DEVICE

(71) Applicant: ATROPOS LIMITED, Bray (IE)

(72) Inventors: Kirk Anthony Shibley, Wayzata, MN (US); Frank Bonadio, Bray (IE); Trevor Vaugh, Birr (IE); Shane Joseph MacNally, Delgany (IE); Lucy Dolores Halpin, Dublin (IE); Stephen Williams, County Dublin (IE)

(73) Assignee: Atropos Limited, Bray (IE)

( * ) Notice: Subject to any disclaimer, the term of this patent is extended or adjusted under 35 U.S.C. 154(b) by 205 days.

(21) Appl. No.: 16/206,408

(22) Filed: Nov. 30, 2018

(65) Prior Publication Data

US 2019/0090863 A1    Mar. 28, 2019

Related U.S. Application Data

(63) Continuation of application No. 14/996,610, filed on Jan. 15, 2016, now abandoned, which is a
(Continued)

(51) Int. Cl.
*A61B 1/32* (2006.01)
*A61B 17/00* (2006.01)
(Continued)

(52) U.S. Cl.
CPC .... *A61B 17/00234* (2013.01); *A61B 17/0218* (2013.01); *A61B 17/22* (2013.01); *A61B 17/3423* (2013.01); *A61J 1/10* (2013.01); *A61M 13/003* (2013.01); *A61B 17/0293* (2013.01); *A61B 17/3474* (2013.01); *A61B 2017/00287* (2013.01); *A61B 2017/00557* (2013.01);
(Continued)

(58) Field of Classification Search
CPC combination set(s) only.
See application file for complete search history.

(56) References Cited

U.S. PATENT DOCUMENTS 30,471 A    10/1860  Dudley
4,346,699 A   8/1982  Little et al.
(Continued)

FOREIGN PATENT DOCUMENTS

CN    100477968 C    4/2009
CN    202397525 U    8/2012
(Continued)

OTHER PUBLICATIONS

Matsuda, Tadashi, et al., Future of Urologic Laparascopy, World J. Surg. 24, pp. 1172-1175, Jul. 17, 2000.
(Continued)

*Primary Examiner* — Sameh R Boles
(74) *Attorney, Agent, or Firm* — Bookoff McAndrews, PLLC

(57) ABSTRACT

A method for performing a laparoscopic procedure may include inserting a bag through an opening. The method may also include delivering tissue into the bag, sealing the bag, and inflating the bag to create an artificial pneumoperitoneum that extends the abdomen and provides additional working and viewing space. Further, the method may include carrying out a procedure on the tissue located in the inflated bag.

20 Claims, 85 Drawing Sheets

Related U.S. Application Data continuation of application No. 14/584,865, filed on Dec. 29, 2014, now Pat. No. 9,265,492, which is a continuation of application No. 14/251,362, filed on Apr. 11, 2014, now Pat. No. 8,920,431, which is a continuation-in-part of application No. 13/725,148, filed on Dec. 21, 2012, now abandoned.

(60) Provisional application No. 61/968,770, filed on Mar. 21, 2014, provisional application No. 61/940,681, filed on Feb. 17, 2014, provisional application No. 61/839,461, filed on Jun. 26, 2013, provisional application No. 61/742,125, filed on Aug. 3, 2012, provisional application No. 61/580,088, filed on Dec. 23, 2011.

(51) Int. Cl.
  *A61B 17/34* (2006.01)
  *A61B 17/02* (2006.01)
  *A61M 13/00* (2006.01)
  *A61B 17/22* (2006.01)
  *A61J 1/10* (2006.01)
  *A61B 17/42* (2006.01)
  *A61B 17/32* (2006.01)

(52) U.S. Cl.
  CPC .......... *A61B 2017/00659* (2013.01); *A61B 2017/00946* (2013.01); *A61B 2017/00951* (2013.01); *A61B 2017/0225* (2013.01); *A61B 2017/22061* (2013.01); *A61B 2017/320024* (2013.01); *A61B 2017/3429* (2013.01); *A61B 2017/3447* (2013.01); *A61B 2017/3466* (2013.01); *A61B 2017/4216* (2013.01)

(56) References Cited

U.S. PATENT DOCUMENTS

| | | |
|---|---|---|
| 5,037,379 A | 8/1991 | Clayman et al. |
| 5,074,867 A | 12/1991 | Wilk |
| 5,147,371 A | 9/1992 | Washington et al. |
| 5,190,555 A | 3/1993 | Wetter et al. |
| 5,192,284 A | 3/1993 | Pleatman |
| 5,215,521 A | 6/1993 | Cochran et al. |
| 5,224,930 A | 7/1993 | Spaeth et al. |
| 5,312,416 A | 5/1994 | Spaeth et al. |
| 5,320,627 A | 6/1994 | Sorensen et al. |
| 5,330,483 A | 7/1994 | Heaven et al. |
| 5,337,754 A | 8/1994 | Heaven et al. |
| 5,341,815 A | 8/1994 | Cofone et al. |
| 5,350,387 A | 9/1994 | Semm |
| 5,352,184 A | 10/1994 | Goldberg et al. |
| 5,353,784 A | 10/1994 | Nady-Mohamed |
| 5,354,303 A | 10/1994 | Spaeth et al. |
| 5,368,545 A | 11/1994 | Schaller et al. |
| 5,465,731 A | 11/1995 | Bell et al. |
| 5,480,404 A | 1/1996 | Kammerer et al. |
| 5,522,790 A | 6/1996 | Moll et al. |
| 5,562,603 A | 10/1996 | Moll et al. |
| 5,611,803 A | 3/1997 | Heaven et al. |
| 5,618,296 A | 4/1997 | Sorensen et al. |
| 5,640,977 A | 6/1997 | Leahy et al. |
| 5,645,083 A | 7/1997 | Essig et al. |
| 5,735,289 A | 4/1998 | Pfeffer et al. |
| 5,755,724 A | 5/1998 | Yoon |
| 5,769,794 A | 6/1998 | Conlan et al. |
| 5,785,677 A | 7/1998 | Auweiler |
| 5,788,709 A | 8/1998 | Riek et al. |
| 5,813,409 A | 9/1998 | Leahy et al. |
| 5,836,936 A | 11/1998 | Cuschieri |
| 5,895,392 A | 4/1999 | Riek et al. |
| 5,980,544 A | 11/1999 | Vaitekunas |
| 5,997,547 A | 12/1999 | Nakao et al. |
| 6,004,330 A | 12/1999 | Middleman et al. |
| 6,036,681 A | 3/2000 | Hooven |
| 6,162,235 A | 12/2000 | Vaitekunas |
| 6,206,889 B1 | 3/2001 | Bennardo |
| 6,228,095 B1 | 5/2001 | Dennis |
| 6,270,505 B1 | 8/2001 | Yoshida et al. |
| 6,344,026 B1 | 2/2002 | Burbank et al. |
| 6,350,267 B1 | 2/2002 | Stefanchik |
| 6,383,197 B1 | 5/2002 | Conlon et al. |
| 6,409,733 B1 | 6/2002 | Conlon et al. |
| 6,450,983 B1 | 9/2002 | Rambo |
| 6,508,773 B2 | 1/2003 | Burbank et al. |
| 6,613,952 B2 | 9/2003 | Rambo |
| 6,659,105 B2 | 12/2003 | Burbank et al. |
| 6,685,628 B2 | 2/2004 | Vu |
| 6,887,255 B2 | 5/2005 | Shimm |
| 7,163,510 B2 | 1/2007 | Kahle et al. |
| 7,670,338 B2 | 3/2010 | Albrecht et al. |
| 7,670,346 B2 | 3/2010 | Whitfield |
| 7,955,292 B2 | 6/2011 | Leroy et al. |
| 8,152,820 B2 | 4/2012 | Mohamed et al. |
| 8,187,178 B2 | 5/2012 | Bonadio et al. |
| 8,282,572 B2 | 10/2012 | Bilsbury |
| 8,409,217 B2 | 4/2013 | Parihar et al. |
| 8,486,087 B2 | 7/2013 | Fleming |
| 8,827,968 B2 | 9/2014 | Taylor et al. |
| 8,920,431 B2 | 12/2014 | Shibley et al. |
| 8,956,286 B2 | 2/2015 | Shibley et al. |
| 9,044,210 B1 | 6/2015 | Hoyte et al. |
| 9,265,492 B2 | 2/2016 | Shibley et al. |
| 9,655,644 B2 | 5/2017 | Collins |
| 9,877,893 B2 | 1/2018 | Taylor et al. |
| 2004/0097960 A1 | 5/2004 | Terachi et al. |
| 2004/0138587 A1 | 7/2004 | Lyons, IV |
| 2004/0158261 A1 | 8/2004 | Vu |
| 2004/0215063 A1 | 10/2004 | Bonadio et al. |
| 2005/0090717 A1 | 4/2005 | Bonadio et al. |
| 2006/0200169 A1 | 9/2006 | Sniffin |
| 2006/0241586 A1 | 10/2006 | Wilk |
| 2007/0135780 A1 | 6/2007 | Pagedas |
| 2007/0135781 A1 | 6/2007 | Hart |
| 2008/0033451 A1 | 2/2008 | Rieber et al. |
| 2009/0043315 A1 | 2/2009 | Moon |
| 2009/0326546 A1 | 12/2009 | Mohamed et al. |
| 2010/0219091 A1 | 9/2010 | Turner |
| 2010/0228092 A1 | 9/2010 | Ortiz et al. |
| 2011/0071359 A1 | 3/2011 | Bonadio et al. |
| 2011/0071361 A1* | 3/2011 | Mollenauer ........ A61B 17/0218 600/207 |
| 2011/0087235 A1 | 4/2011 | Taylor et al. |
| 2011/0299799 A1 | 12/2011 | Towe |
| 2012/0277758 A1 | 11/2012 | Davis et al. |
| 2013/0131457 A1 | 5/2013 | Seckin |
| 2013/0131689 A1 | 5/2013 | Farascioni |
| 2013/0184536 A1 | 7/2013 | Shibley et al. |
| 2013/0218170 A1 | 8/2013 | Uznanski et al. |
| 2013/0253267 A1 | 9/2013 | Collins |
| 2015/0305772 A1 | 10/2015 | McCauley |
| 2016/0100857 A1 | 4/2016 | Wachli et al. |
| 2016/0135798 A1 | 5/2016 | Macleod et al. |
| 2016/0183932 A1 | 6/2016 | Shibley et al. |
| 2016/0199051 A1 | 7/2016 | Shibley et al. |
| 2016/0242751 A1 | 8/2016 | Bonadio et al. |
| 2017/0049427 A1 | 2/2017 | Do et al. |
| 2017/0056065 A1 | 3/2017 | Do et al. |
| 2017/0231611 A1 | 8/2017 | Holsten et al. |
| 2017/0325798 A1 | 11/2017 | Prior |
| 2017/0325800 A1 | 11/2017 | Prior |
| 2018/0021030 A1 | 1/2018 | Fridlin |

FOREIGN PATENT DOCUMENTS

| | | |
|---|---|---|
| CN | 205683099 U | 11/2016 |
| DE | 4405831 A1 | 8/1995 |
| DE | 4405831 C2 | 9/1996 |
| EP | 0 578 997 A1 | 1/1994 |
| EP | 0 465 051 B1 | 8/1995 |
| EP | 2 265 186 B1 | 11/2011 |
| GB | 2460099 A | 11/2009 |

(56) References Cited

FOREIGN PATENT DOCUMENTS

| | | |
|---|---|---|
| IN | 5813/CHE/2014 | 12/2014 |
| JP | H04-309340 | 10/1992 |
| JP | H06-319795 | 11/1994 |
| JP | H08-140983 | 6/1996 |
| JP | H08-294493 | 11/1996 |
| JP | H09-173337 | 7/1997 |
| JP | 2009-039504 | 2/2009 |
| JP | 2010-207578 | 9/2010 |
| JP | 2011-103926 | 6/2011 |
| WO | WO 95/09666 | 4/1995 |
| WO | WO 98/09569 | 3/1998 |
| WO | WO 2005/025427 A1 | 3/2005 |
| WO | WO 2006/044797 A2 | 4/2006 |
| WO | WO 2009/158301 A1 | 12/2009 |
| WO | WO 2010/099541 A1 | 9/2010 |
| WO | WO 2011/090866 A2 | 7/2011 |
| WO | WO 2011/110836 A2 | 9/2011 |
| WO | WO 2013/054093 A1 | 4/2013 |
| WO | WO 2013/075103 A1 | 5/2013 |
| WO | WO 2013/093093 A1 | 6/2013 |
| WO | WO 2014/207077 A1 | 12/2014 |
| WO | WO 2015/151117 A1 | 10/2015 |
| WO | WO 2016/028429 A1 | 2/2016 |
| WO | WO 2016/130982 A1 | 8/2016 |

OTHER PUBLICATIONS

Invitation to Pay Additional Fees and Partial International Search Report from International Application No. PCT/EP2014/063458, dated Oct. 1, 2014 (7pages).
International Preliminary Report on Patentability for International No. PCT/EP2012/076703, dated Jun. 24, 2014 (9 pages).
Requirement for Restriction/Election of Species from U.S. Appl. No. 13/725,148, dated Jun. 5, 2014 (8 pages).
Reply to Requirement for Restriction/Election of Species from U.S. Appl. No. 13/725,148, filed Aug. 5, 2014 (8 pages).
Non-Final Office Action from U.S. Appl. No. 13/725,148, dated Aug. 27, 2014 (13 pages).
International Search Report dated Nov. 14, 2014, in PCT/EP2014/063458 (8 pages).
Final Office Action dated Mar. 18, 2015, in U.S. Appl. No. 13/725,148 (18 pages).
Reply to Office Action filed on Sep. 17, 2015, in U.S. App. No. 13/725,148 (16 pages).
Restriction Requirement in U.S. Appl. No. 14/996,610, dated Jul. 29, 2016 (6 pages).
International Search Report and Written Opinion for Application No. PCT/EP2015/079163, dated Mar. 23, 2016 (11 pages).

* cited by examiner

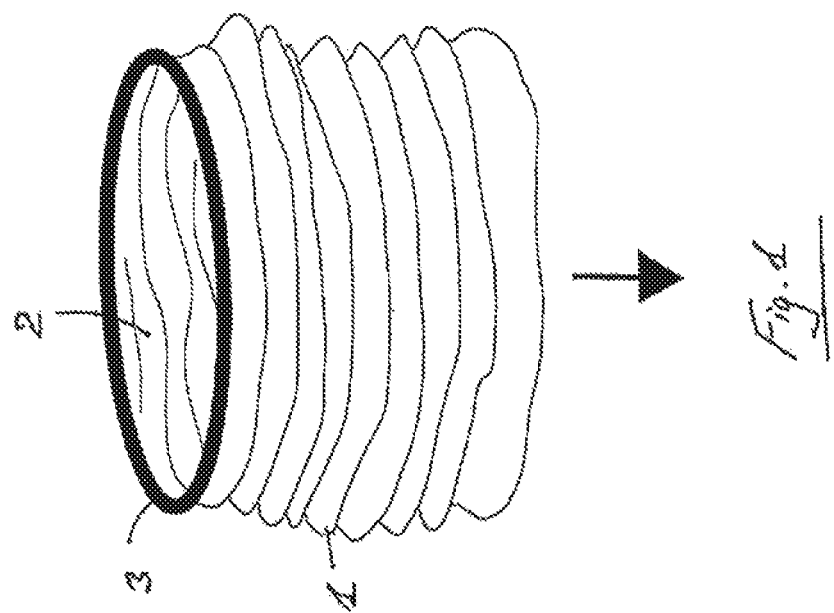
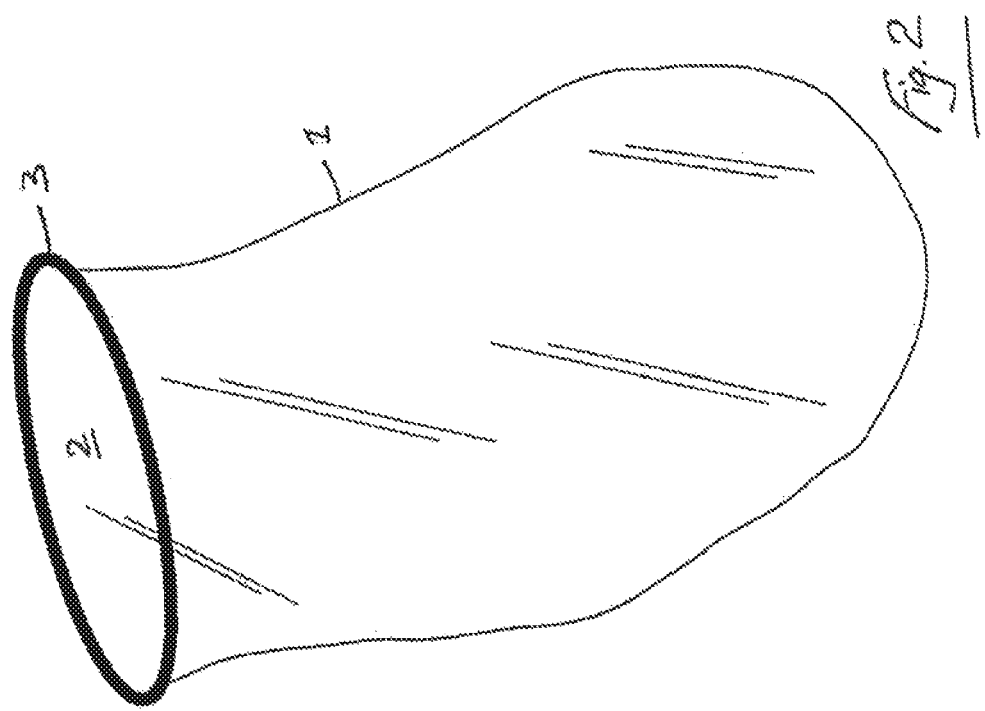

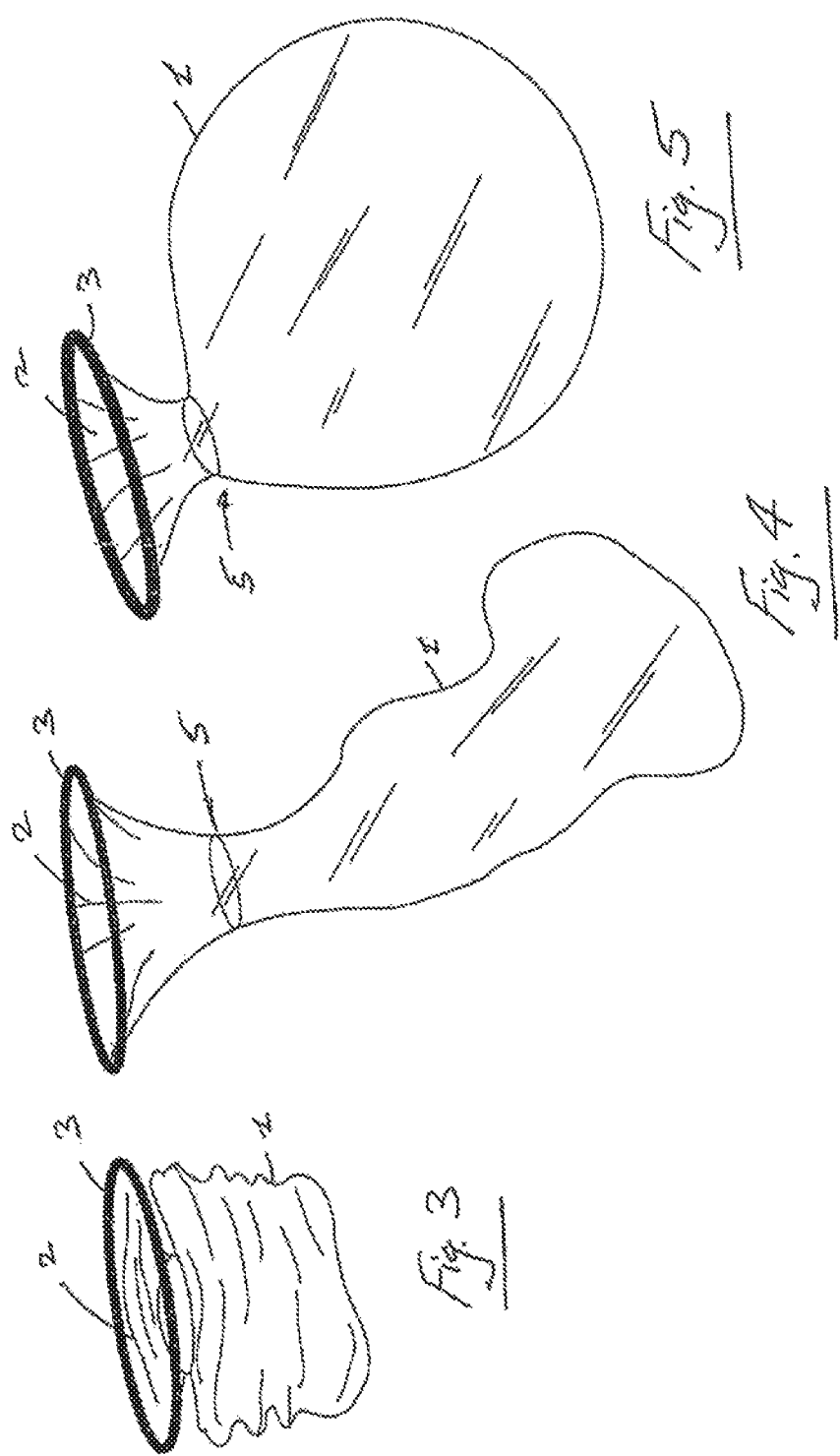

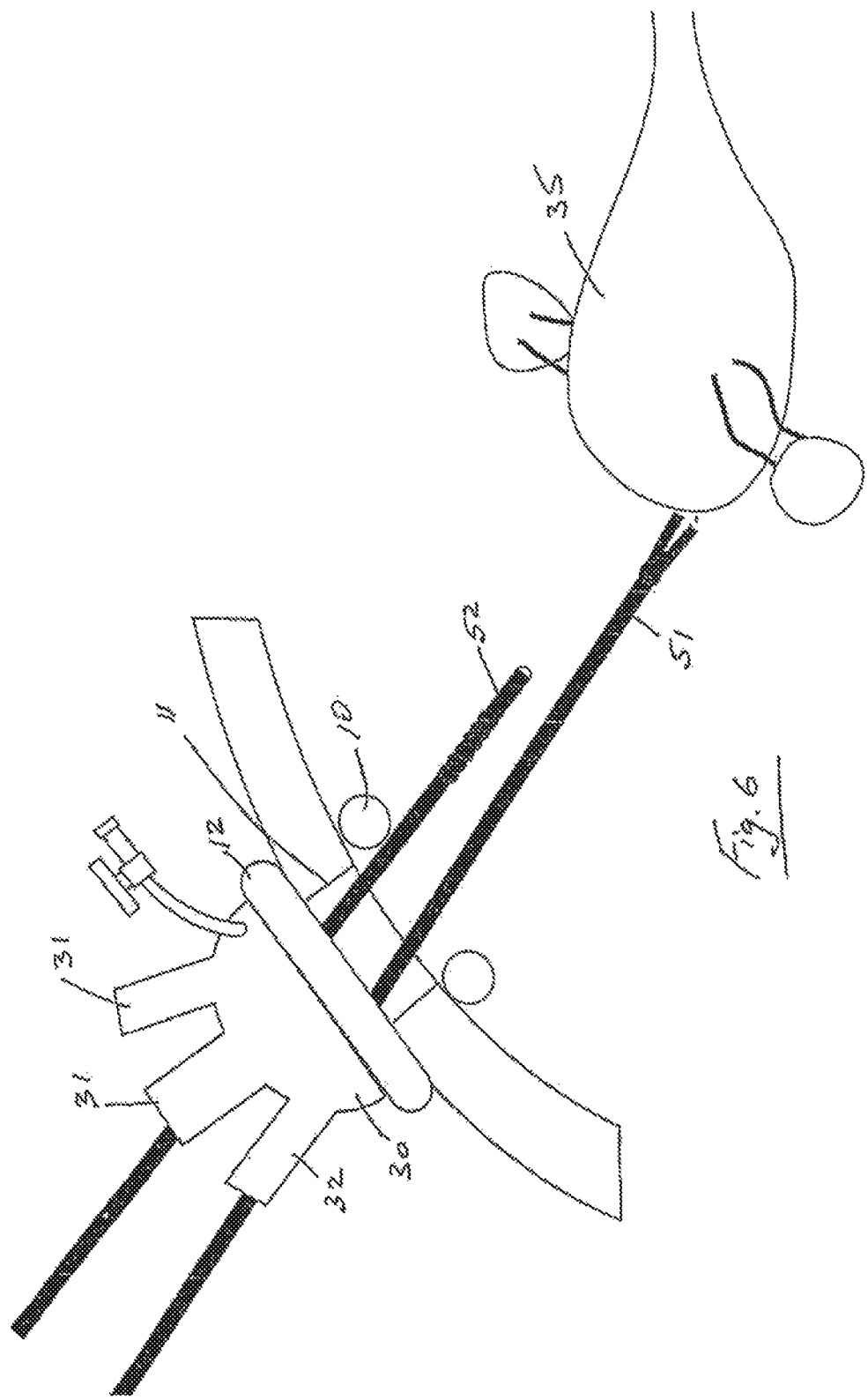

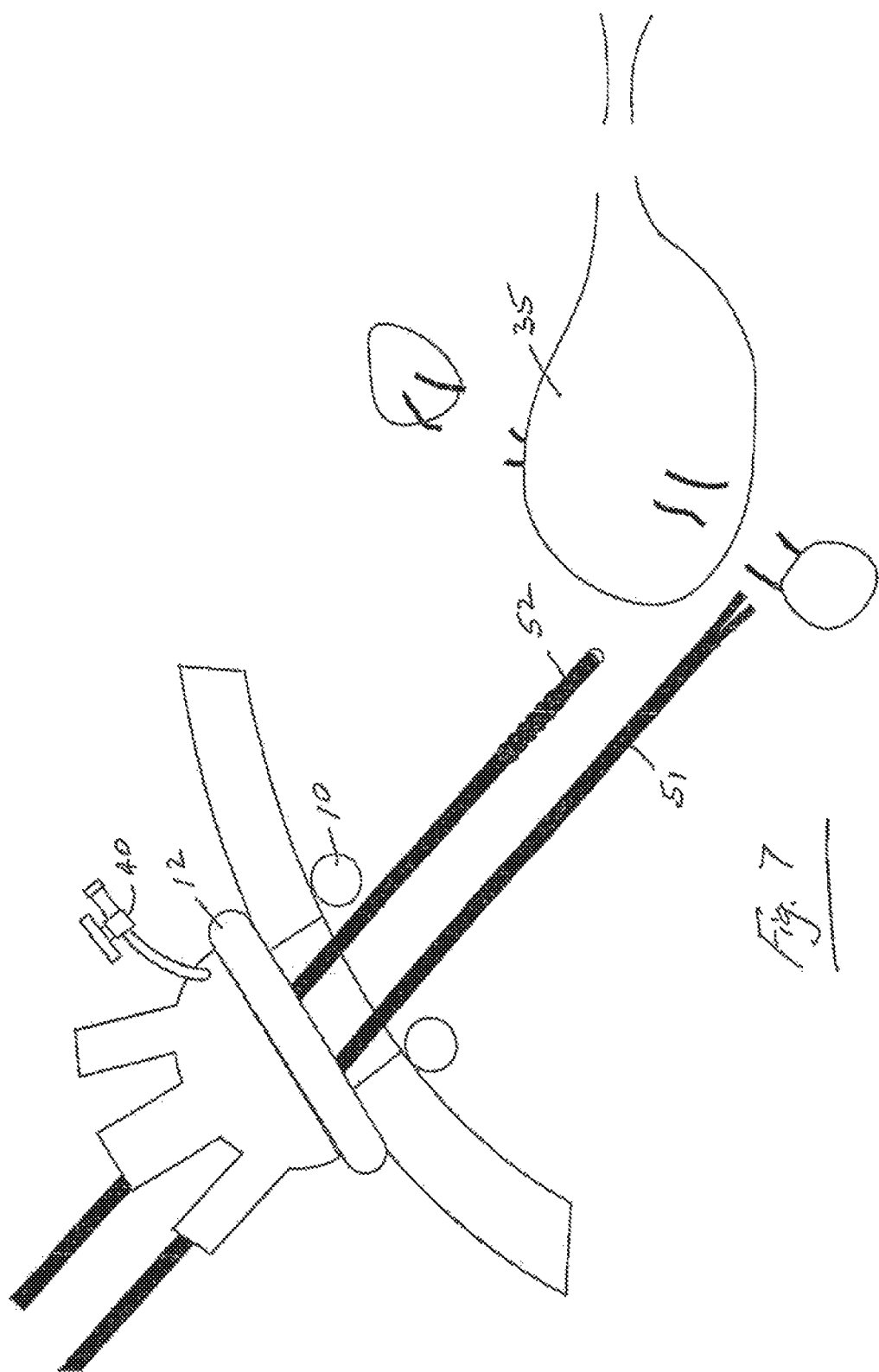

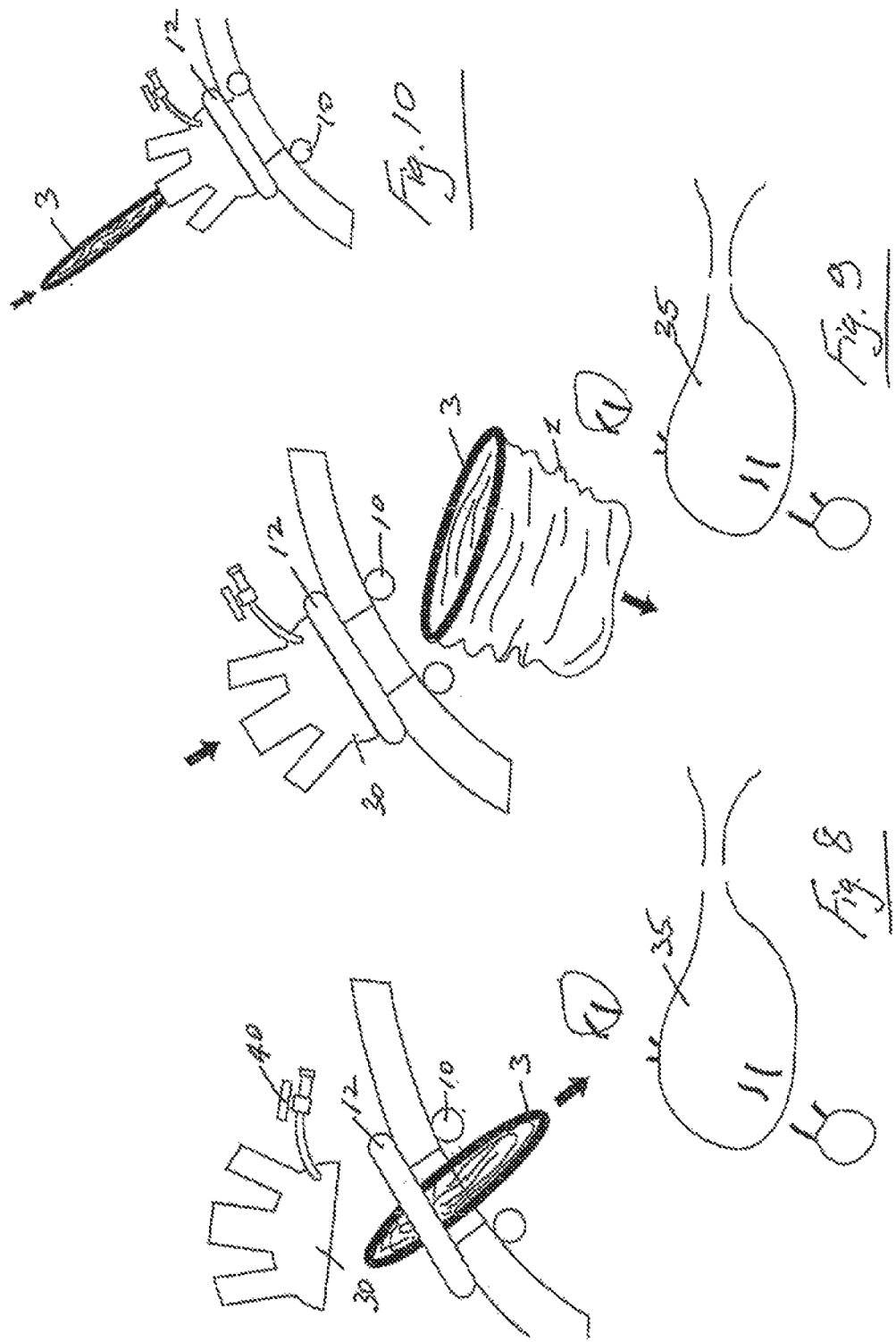

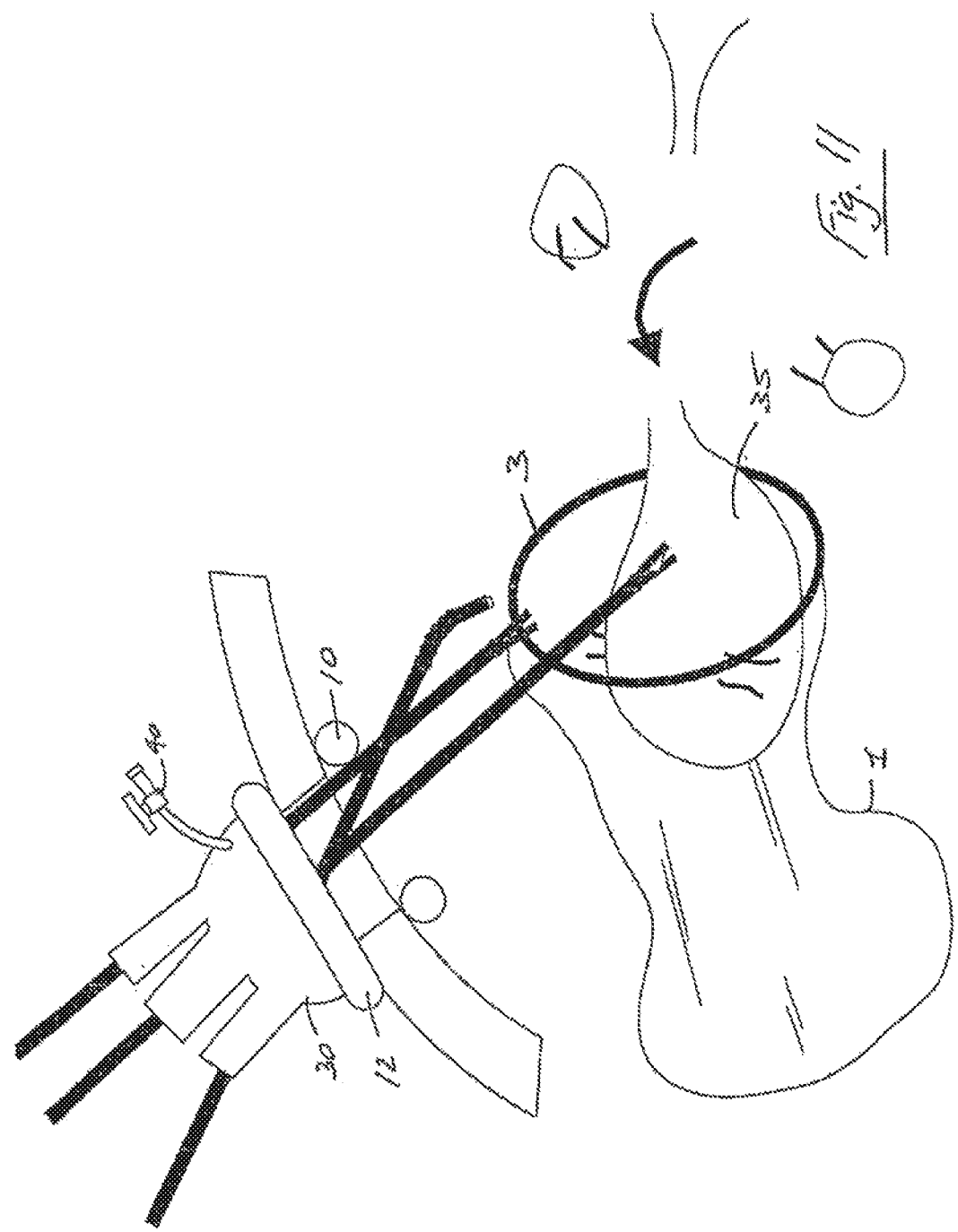

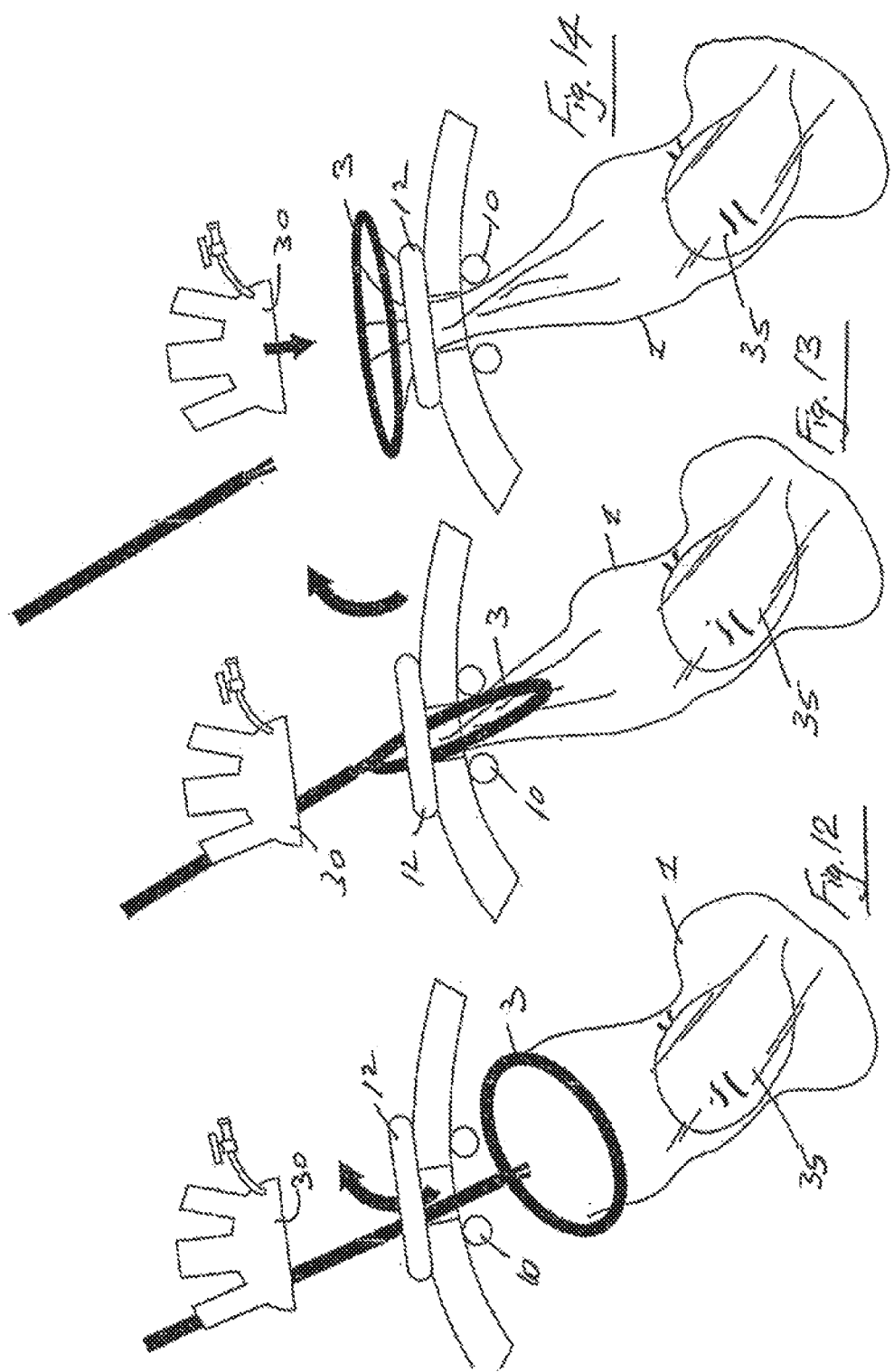

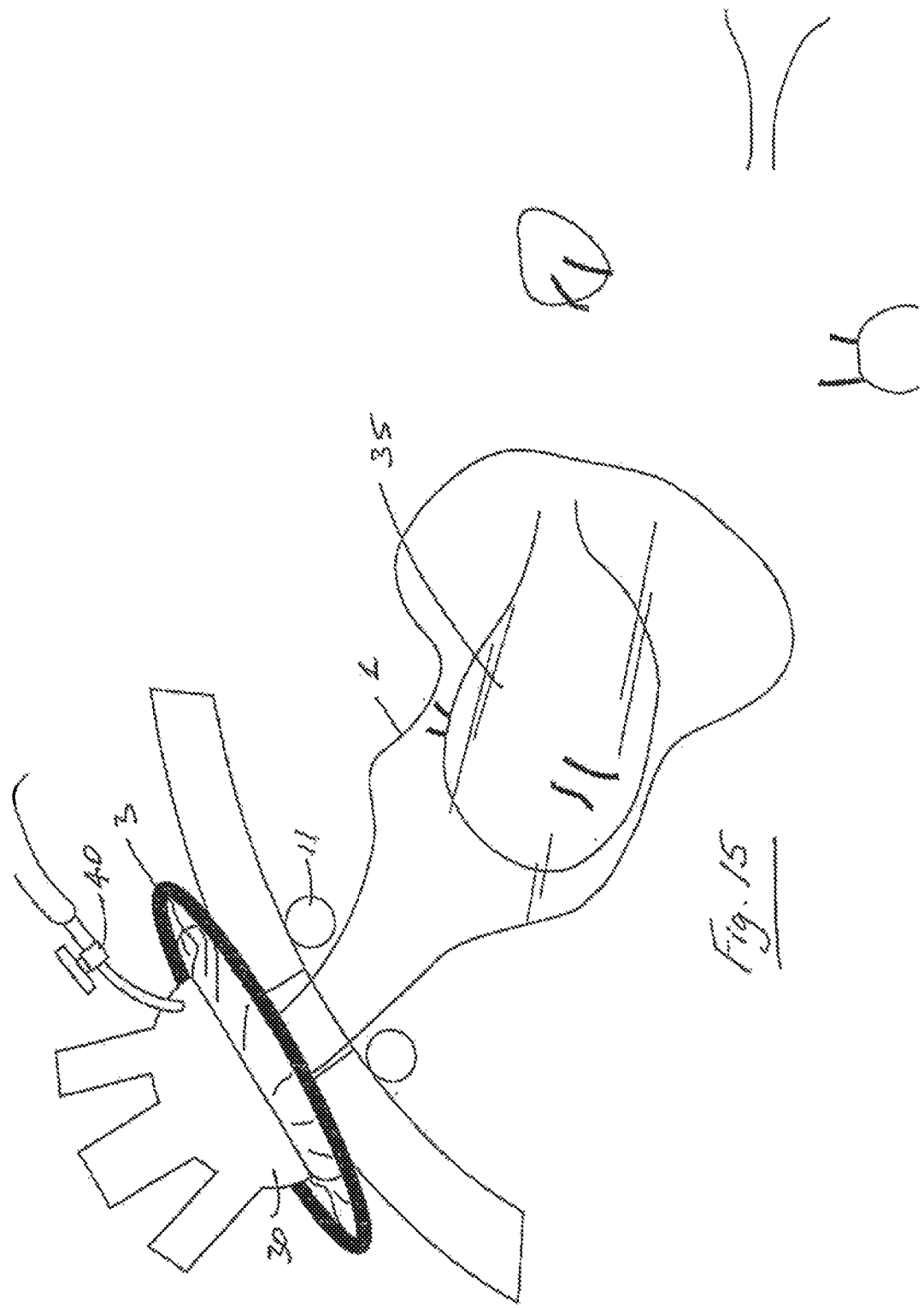

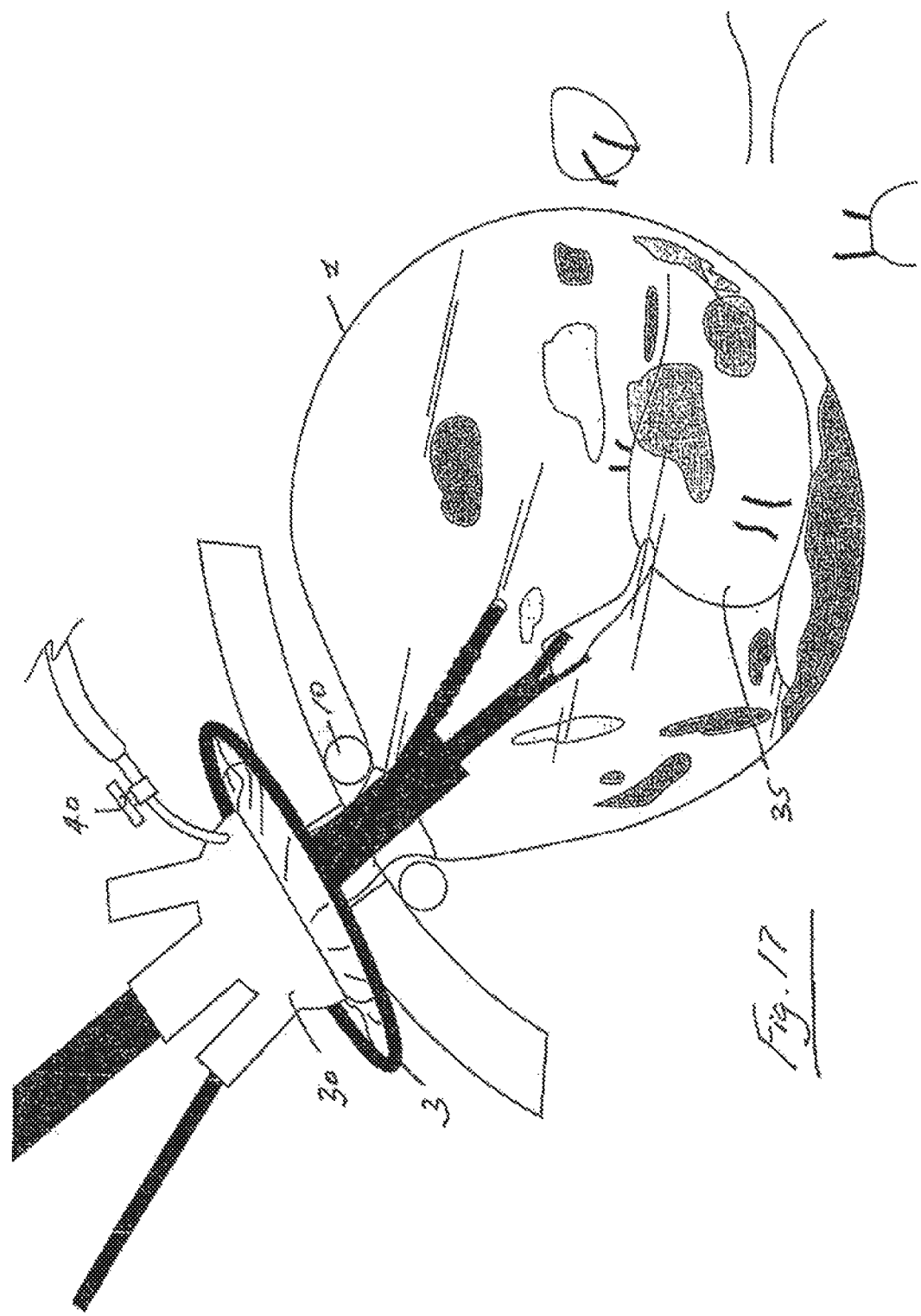

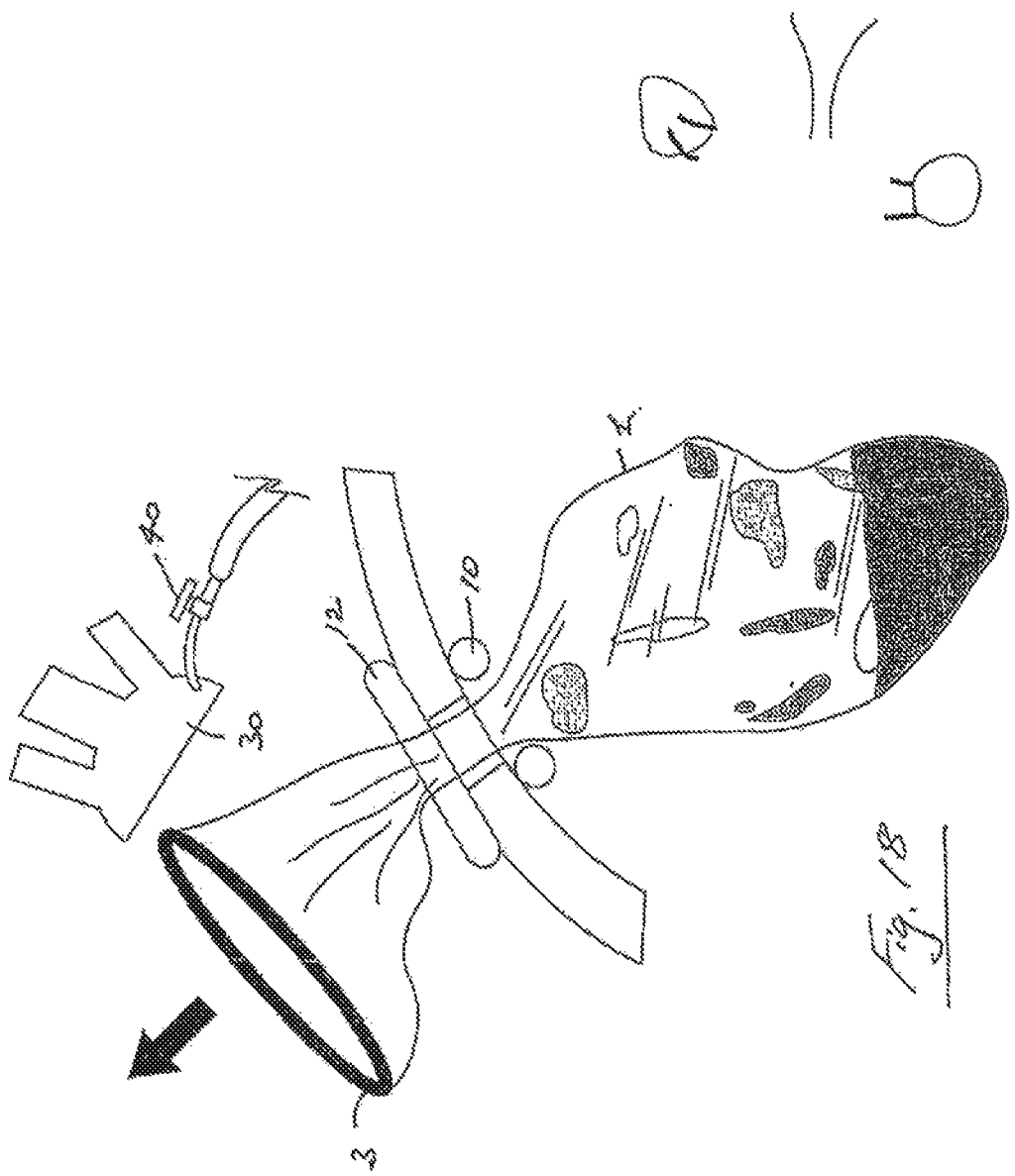

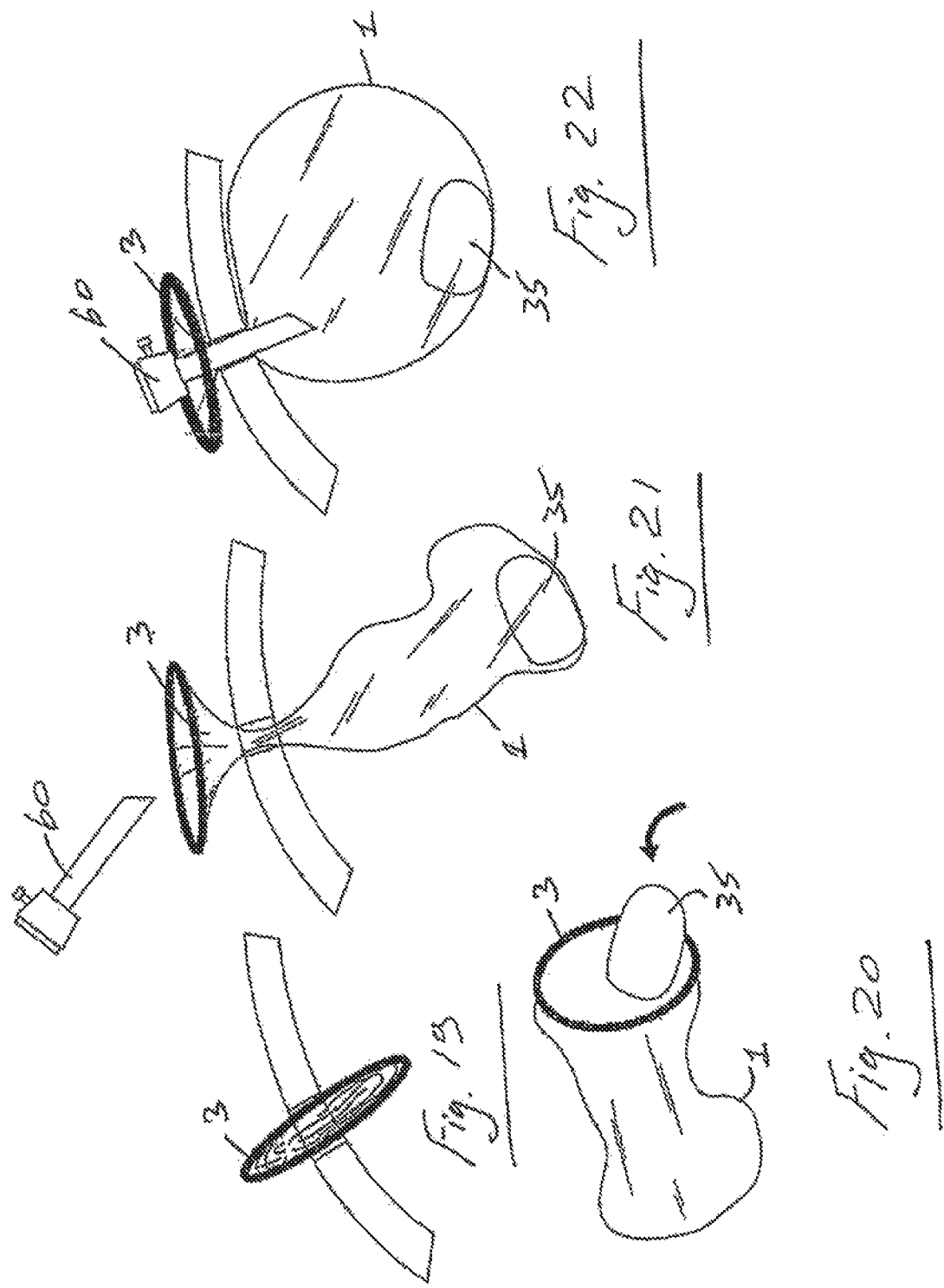

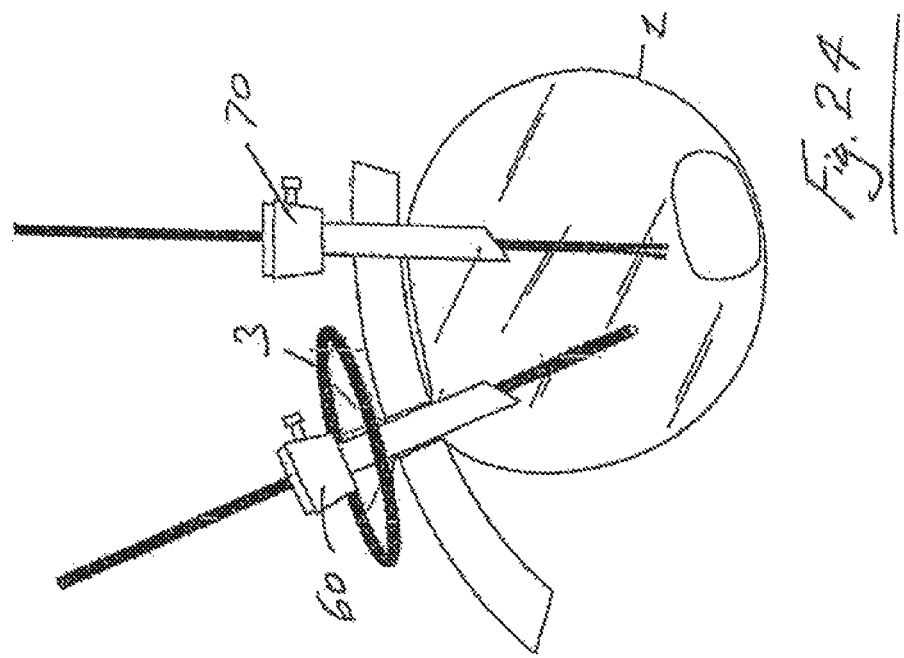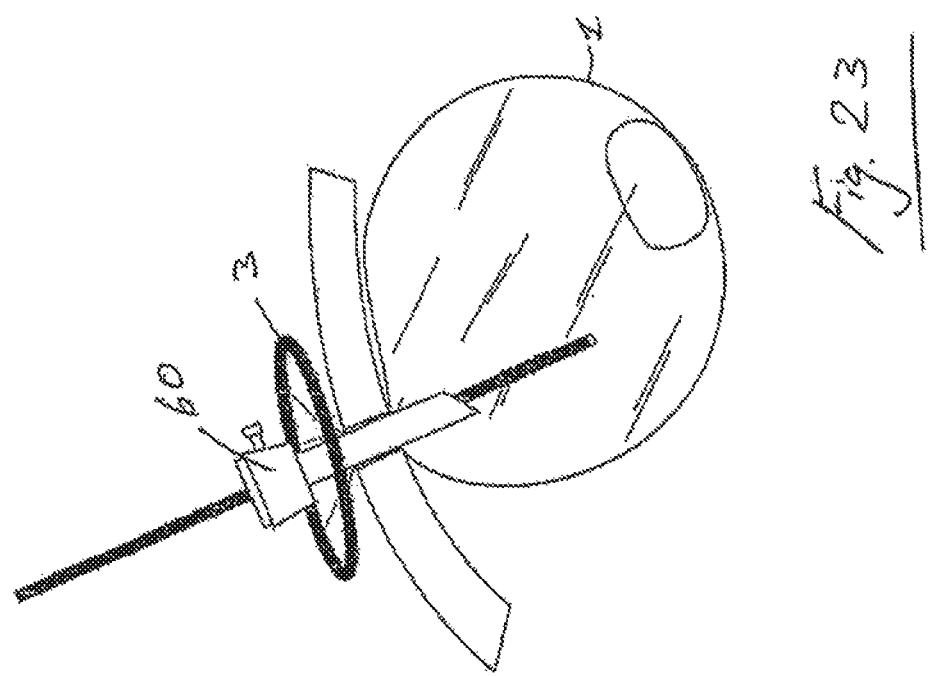

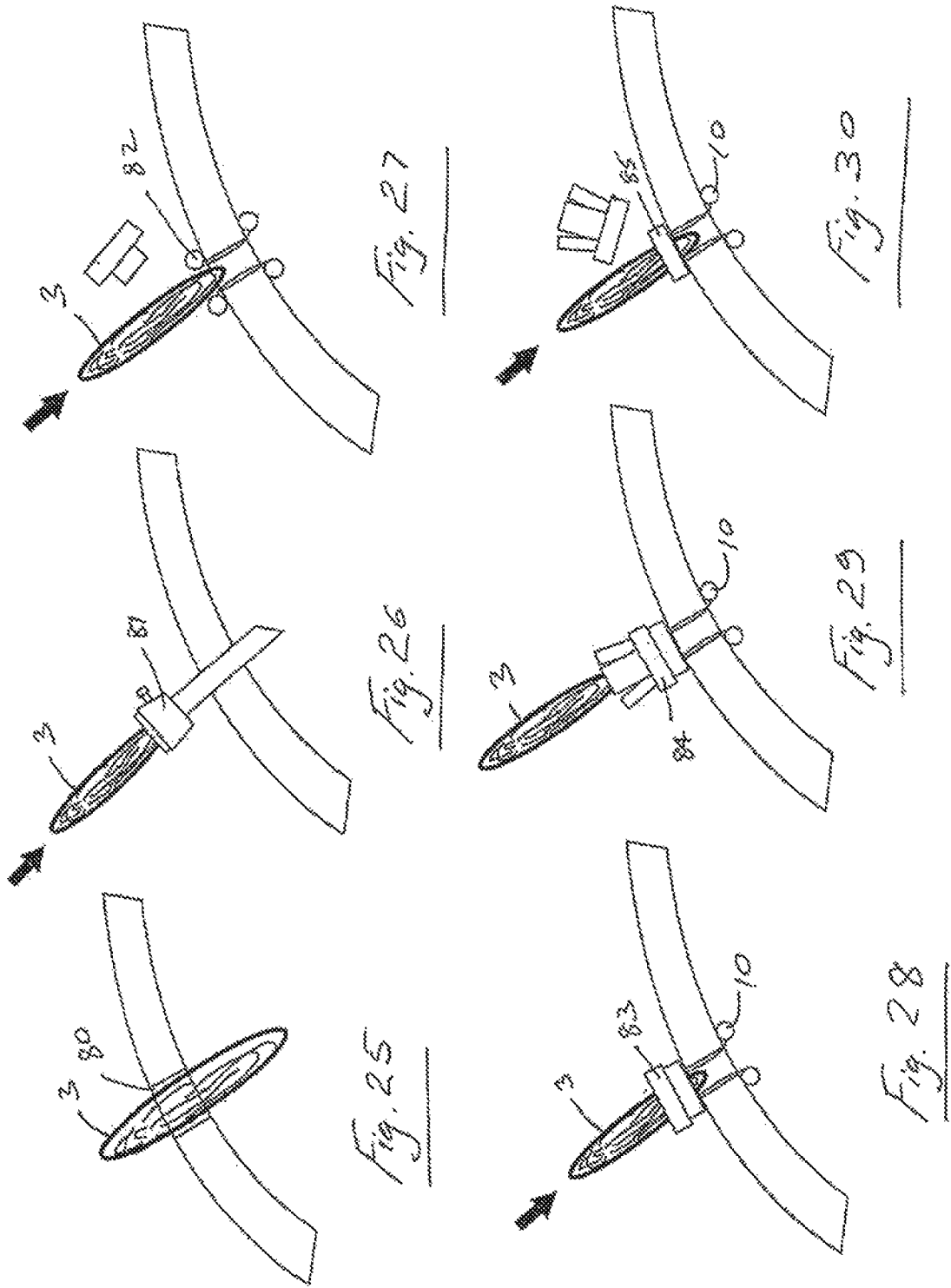

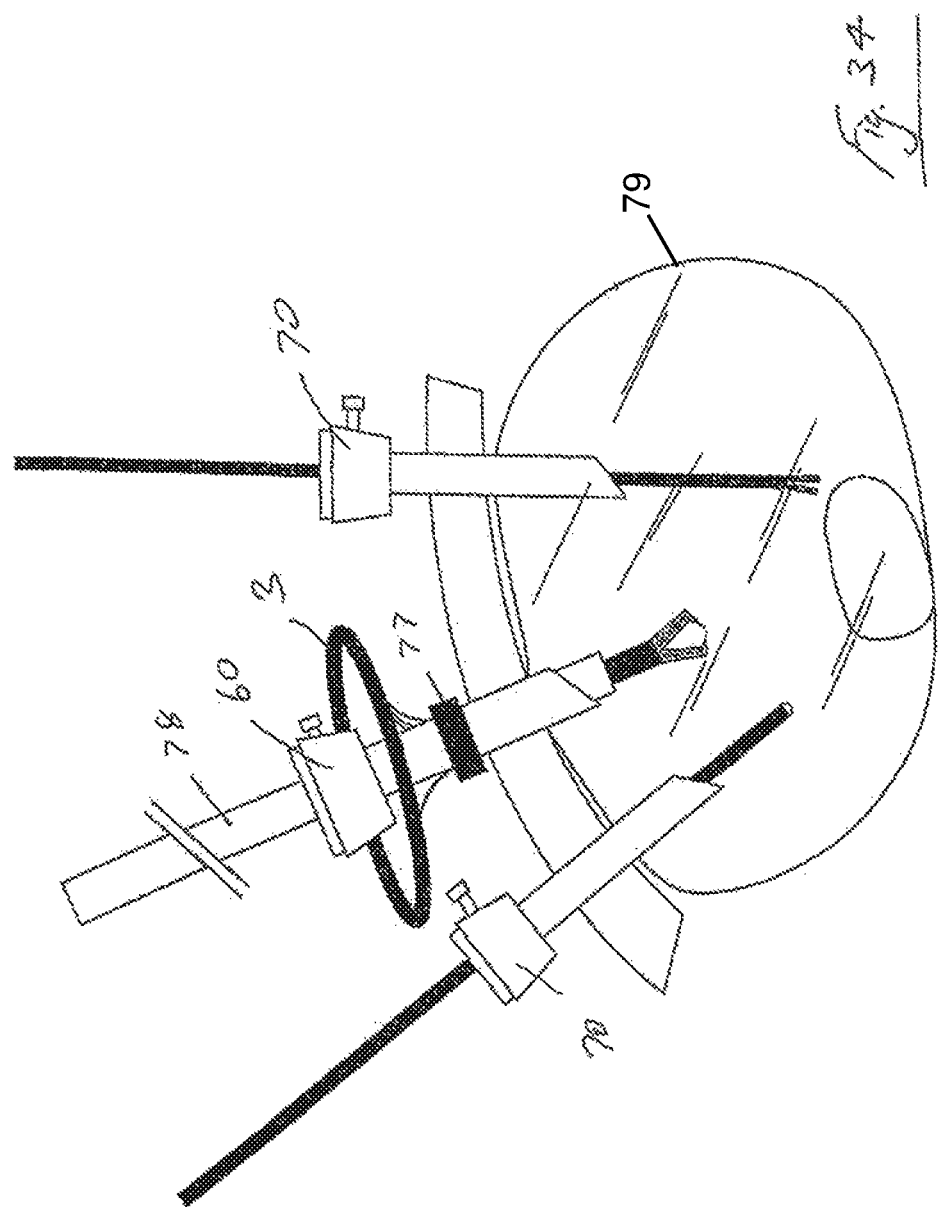

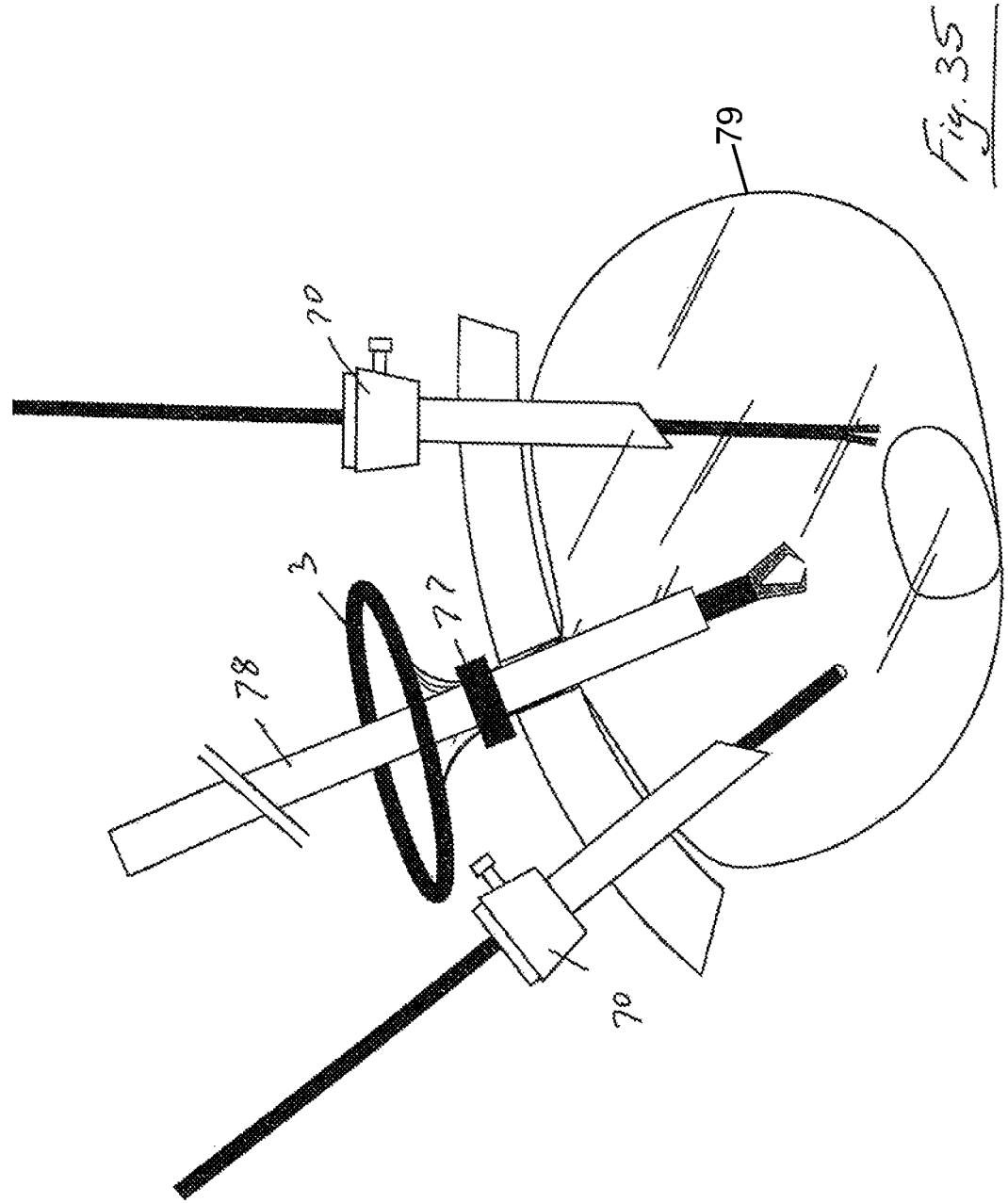

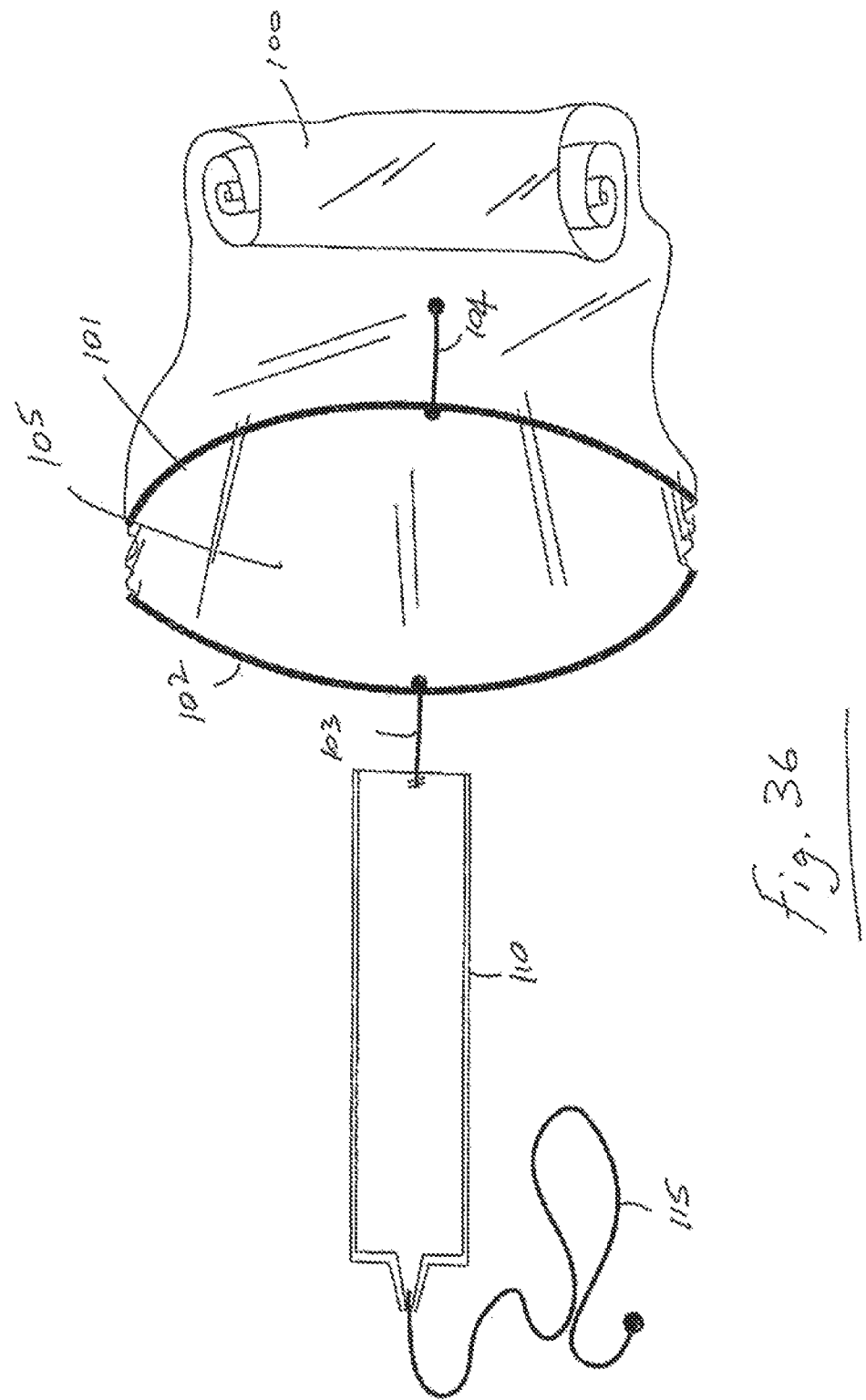

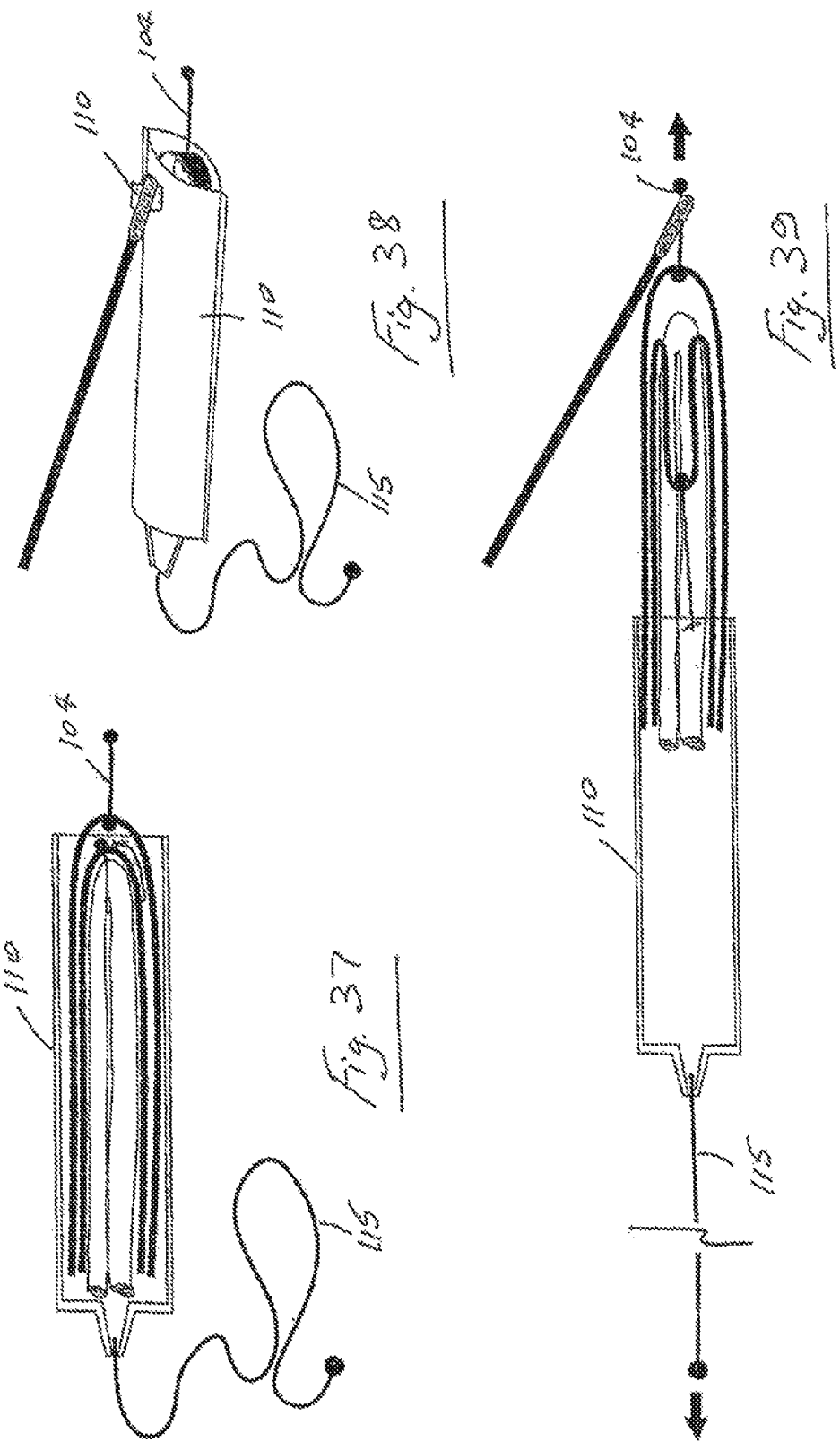

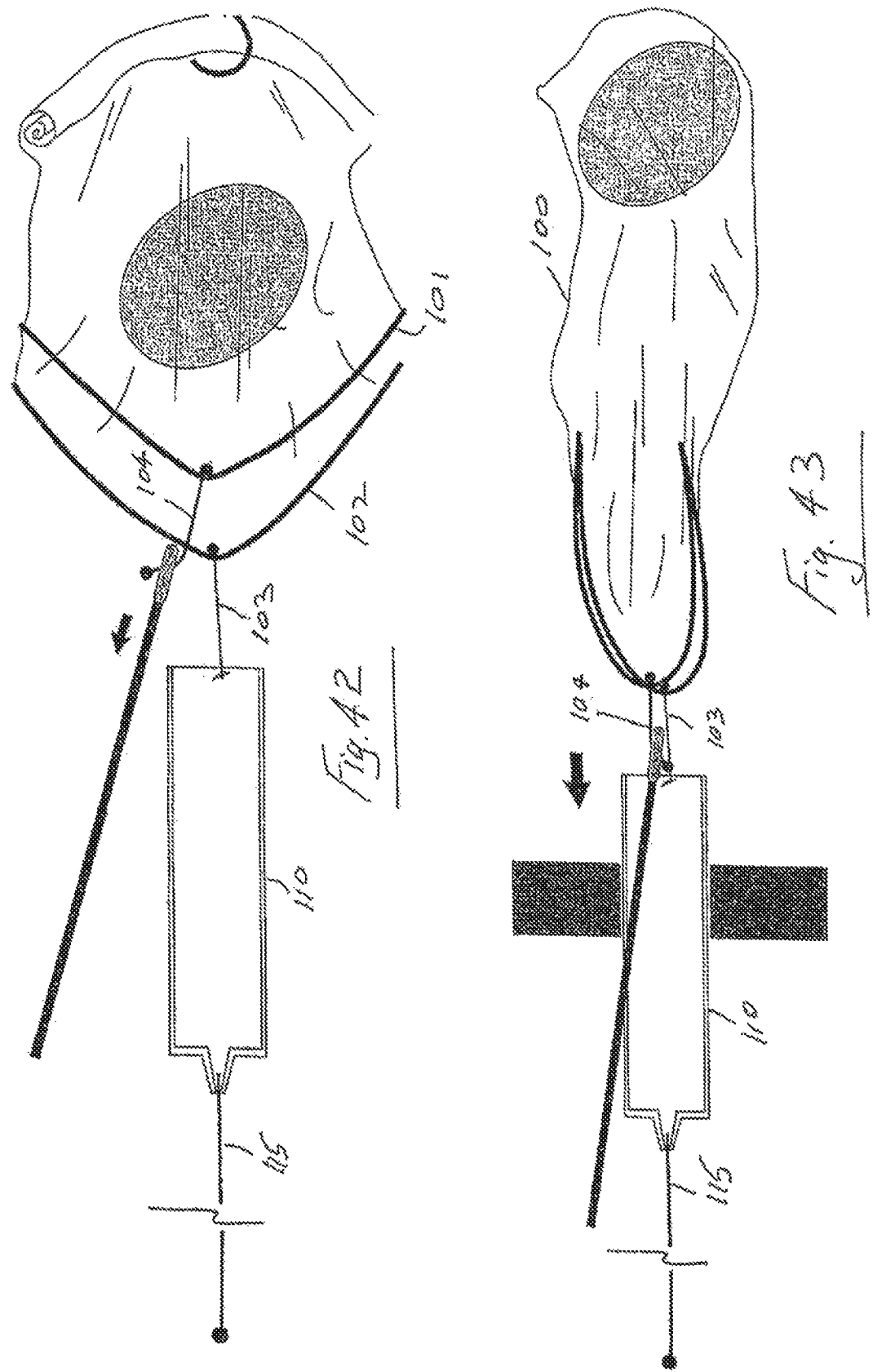

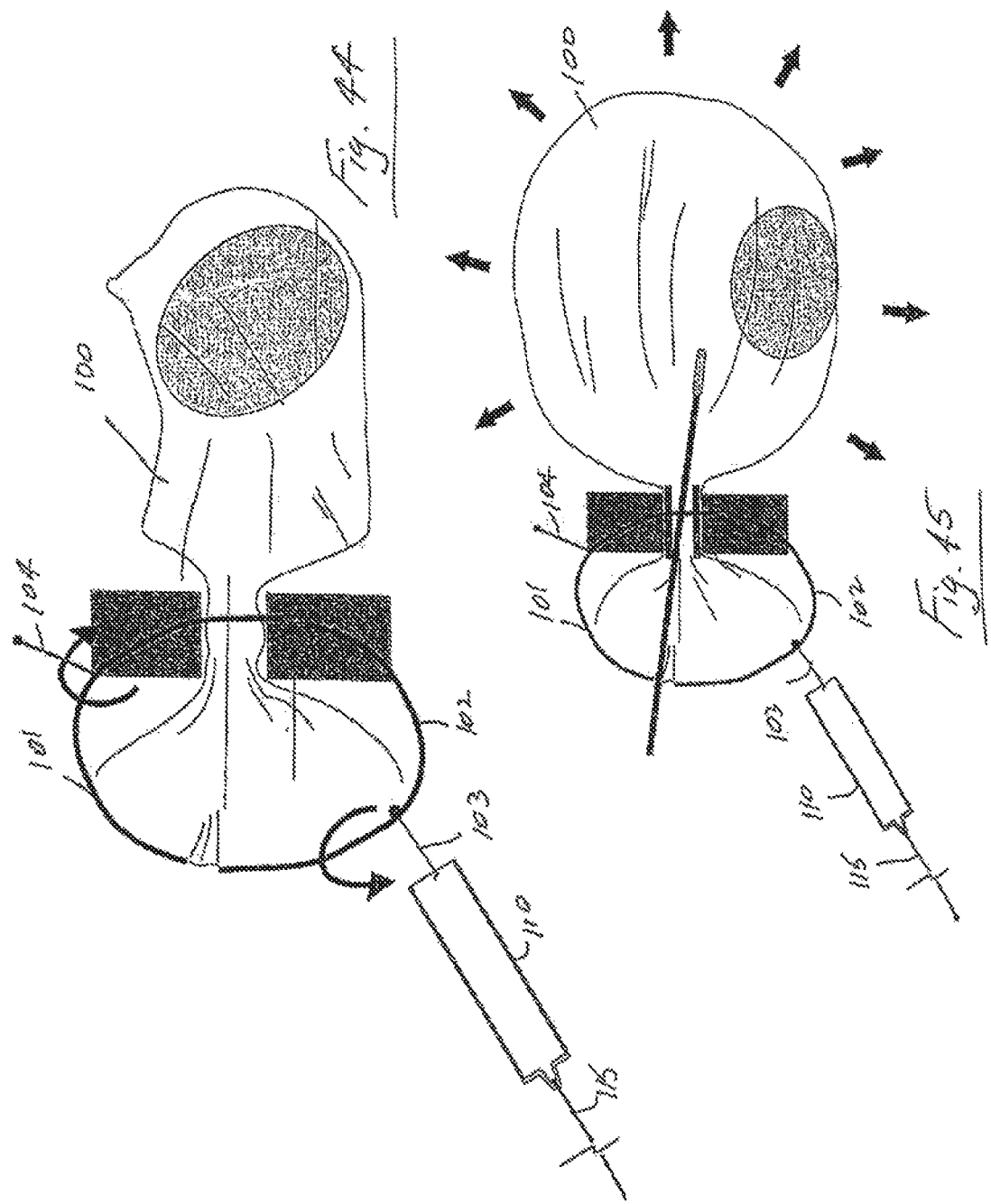

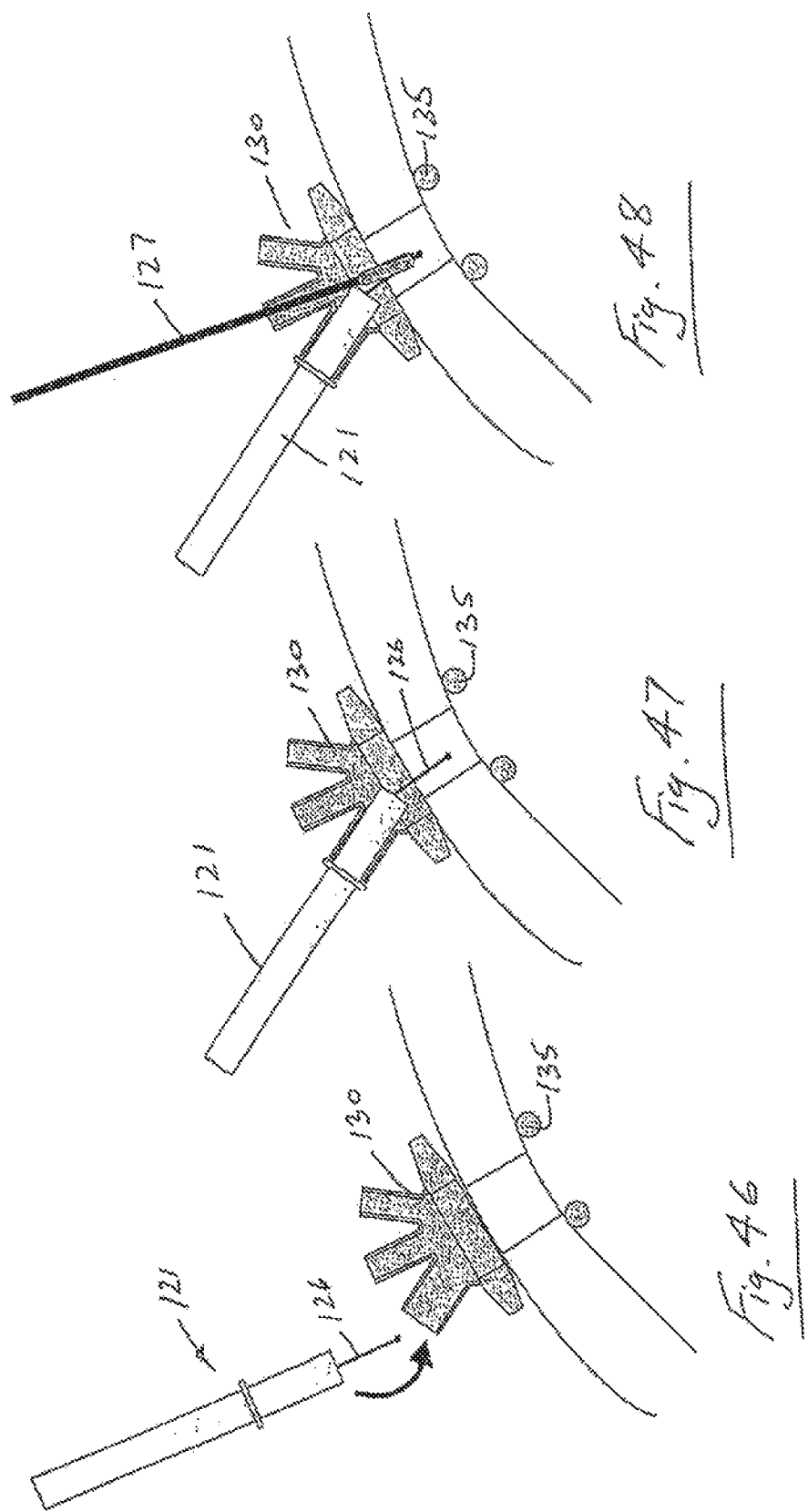

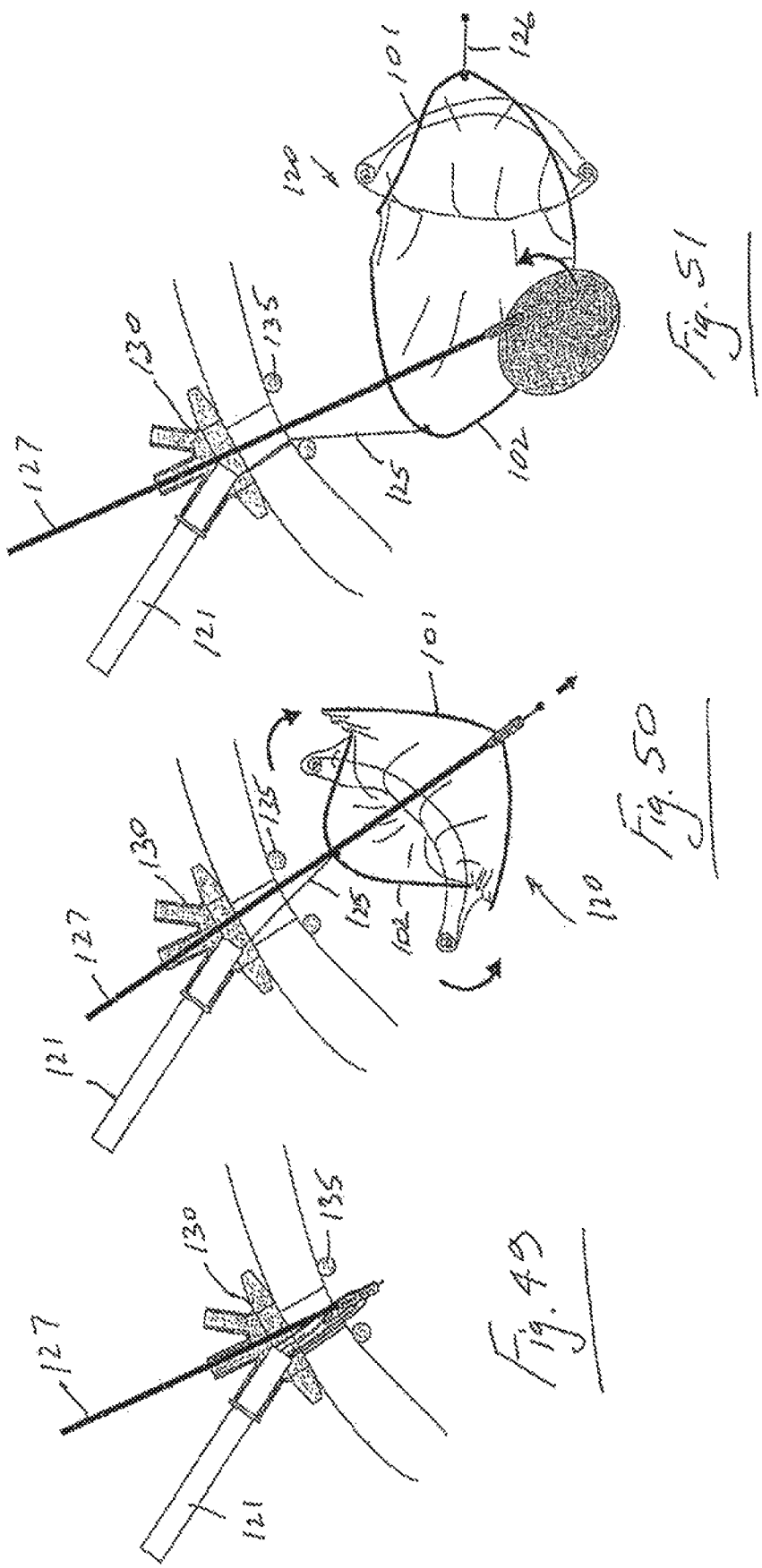

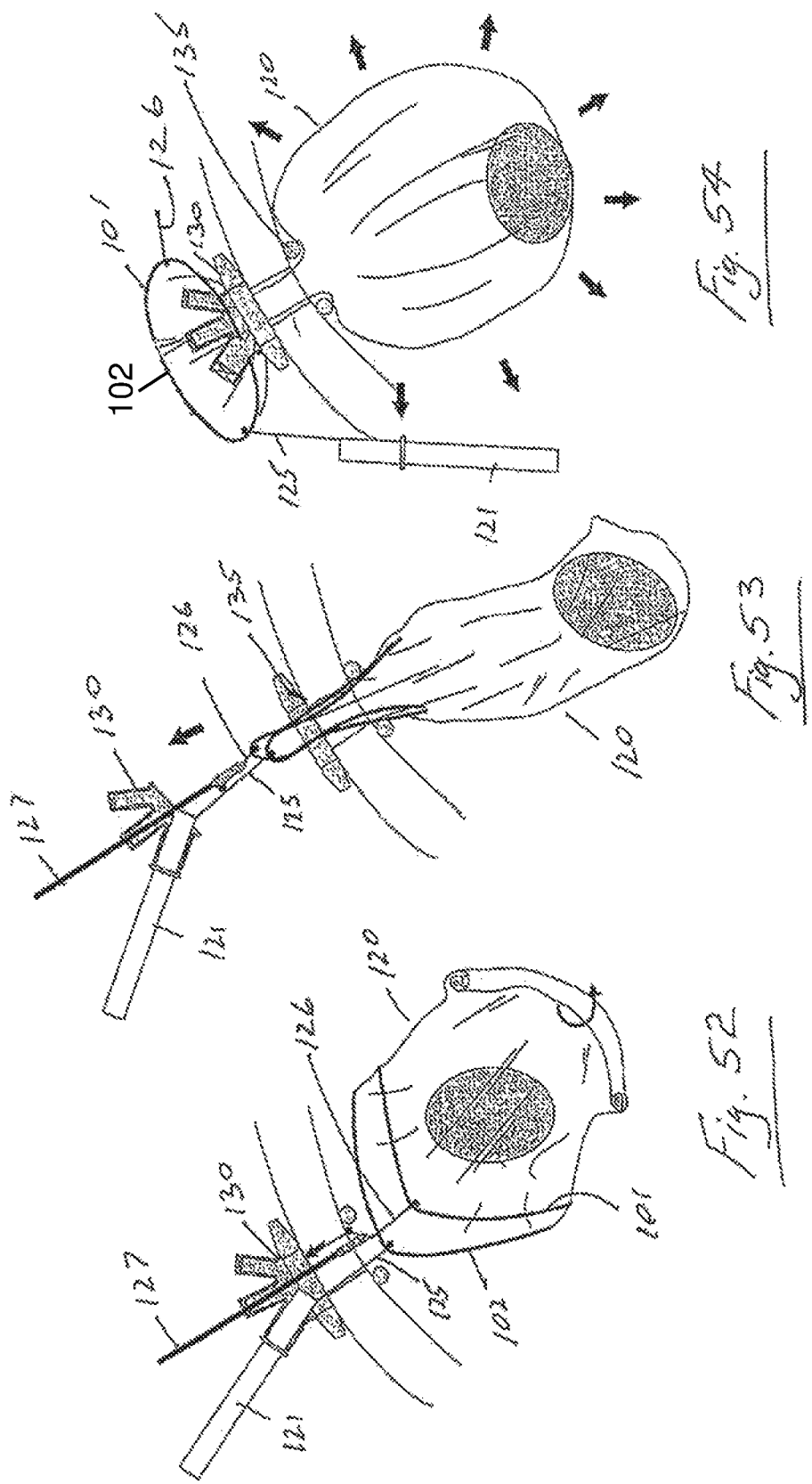

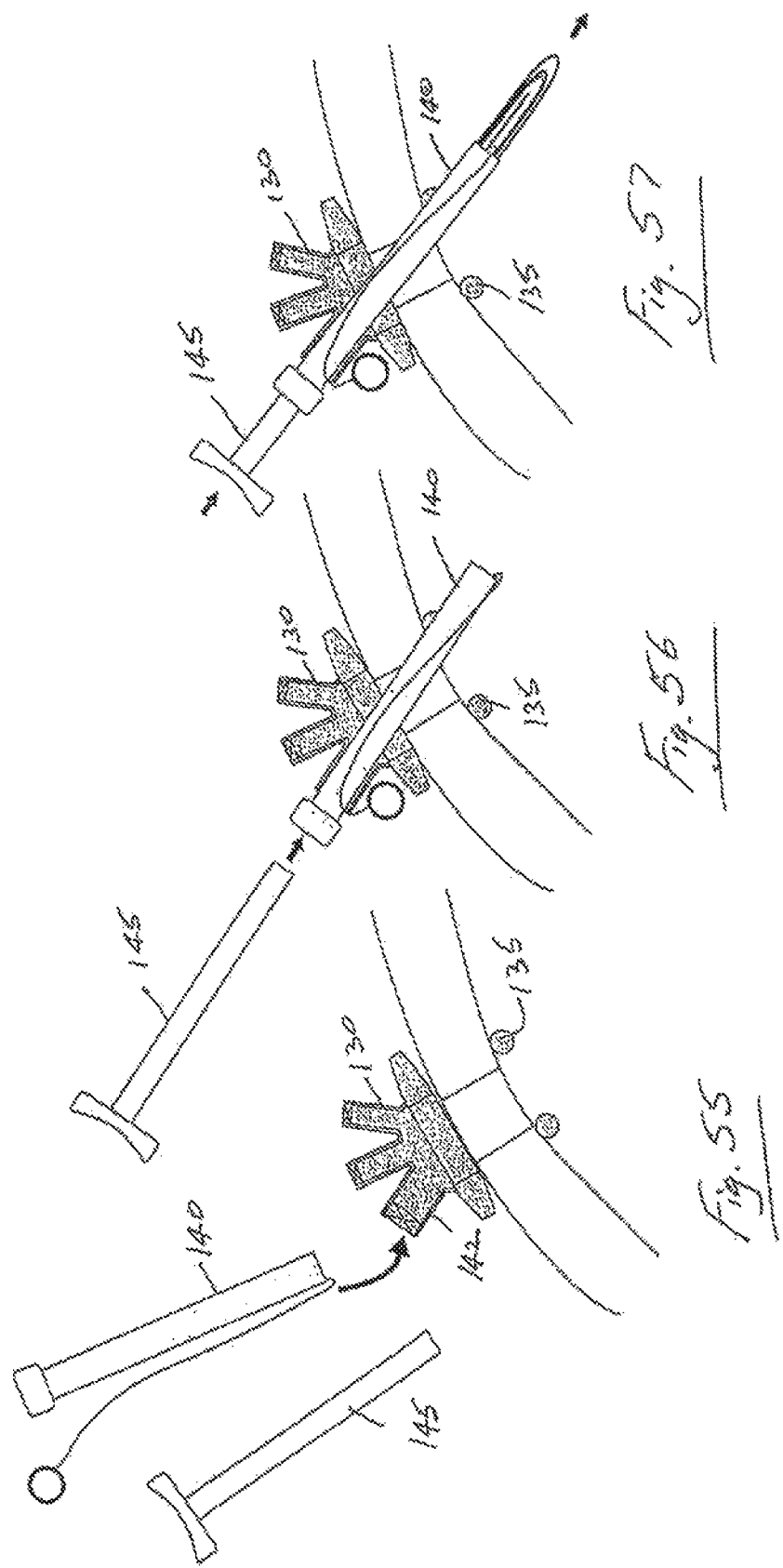

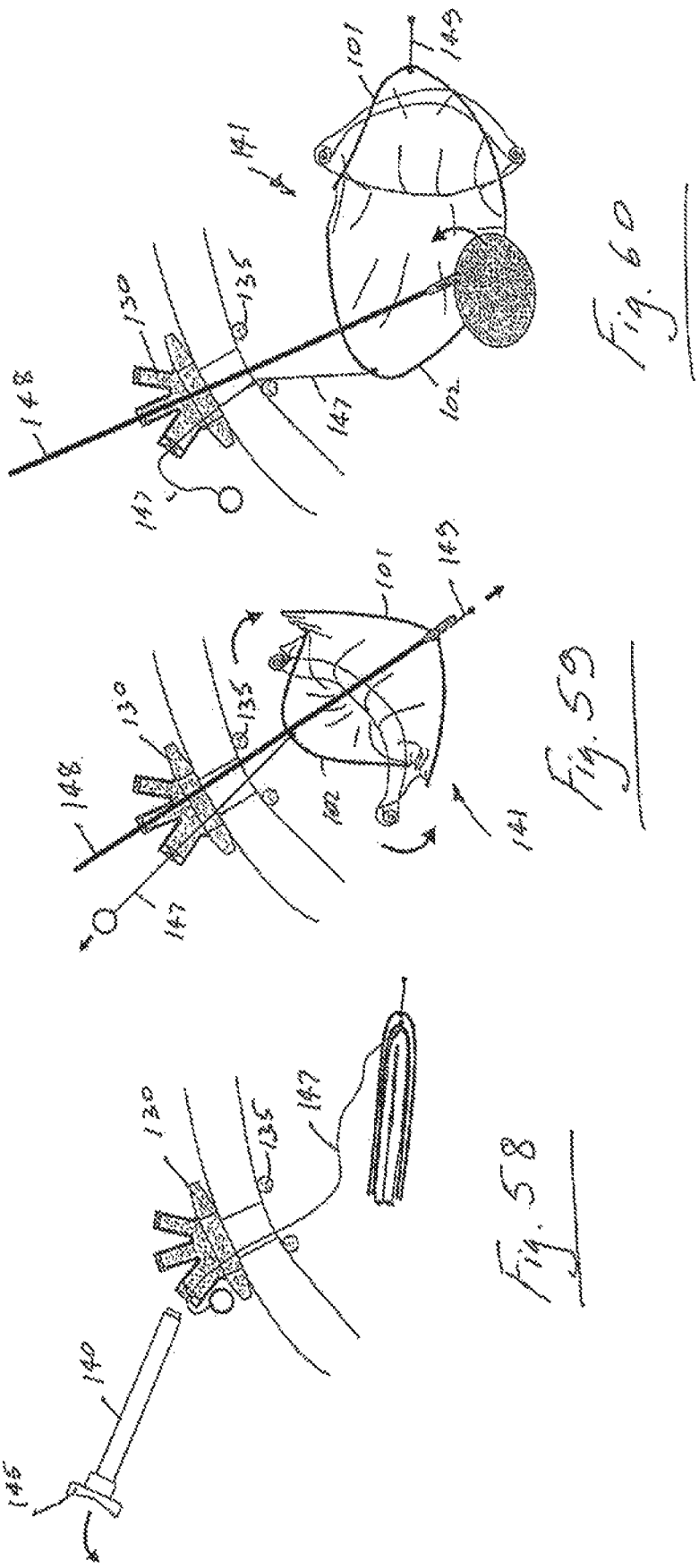

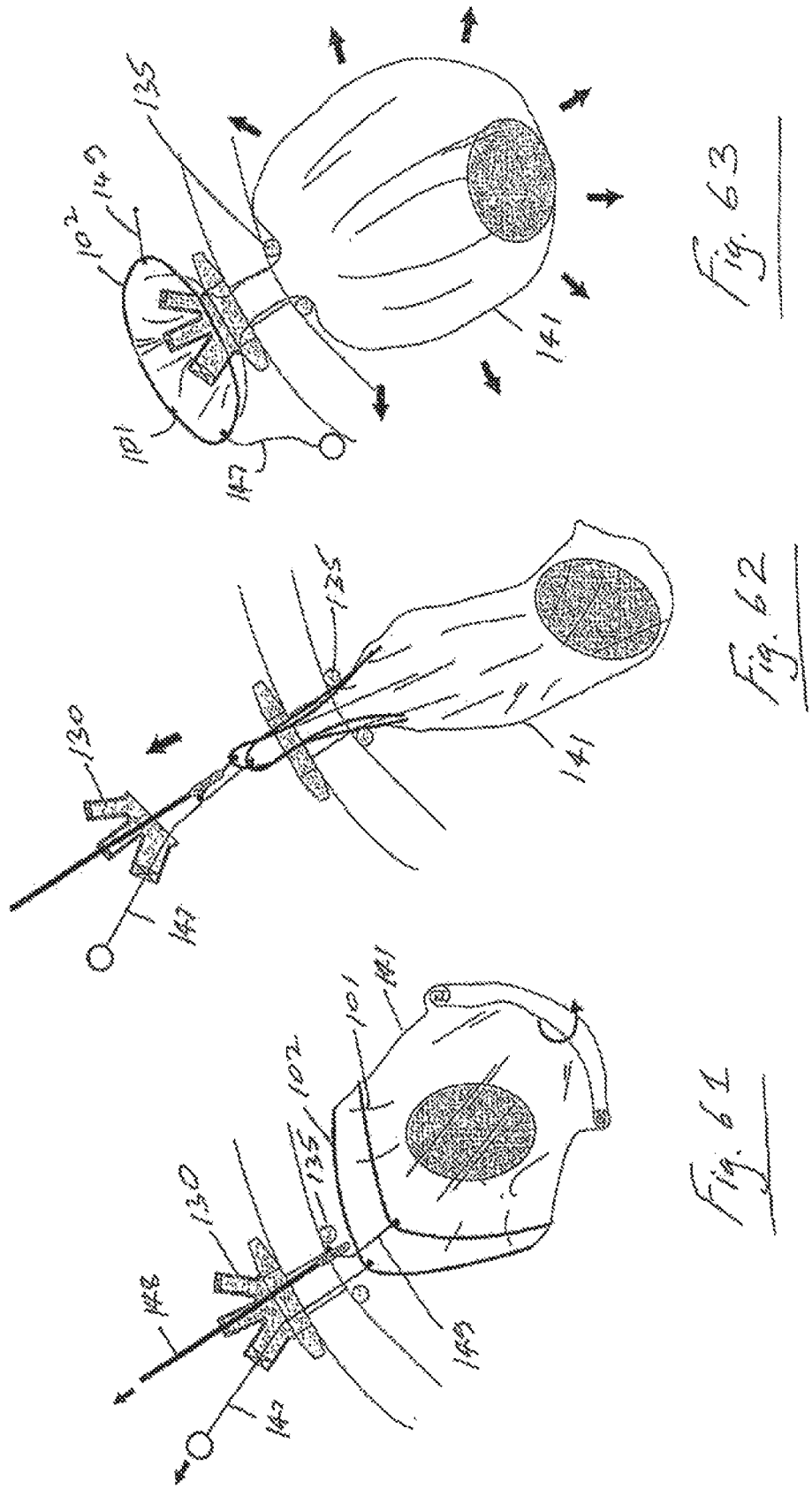

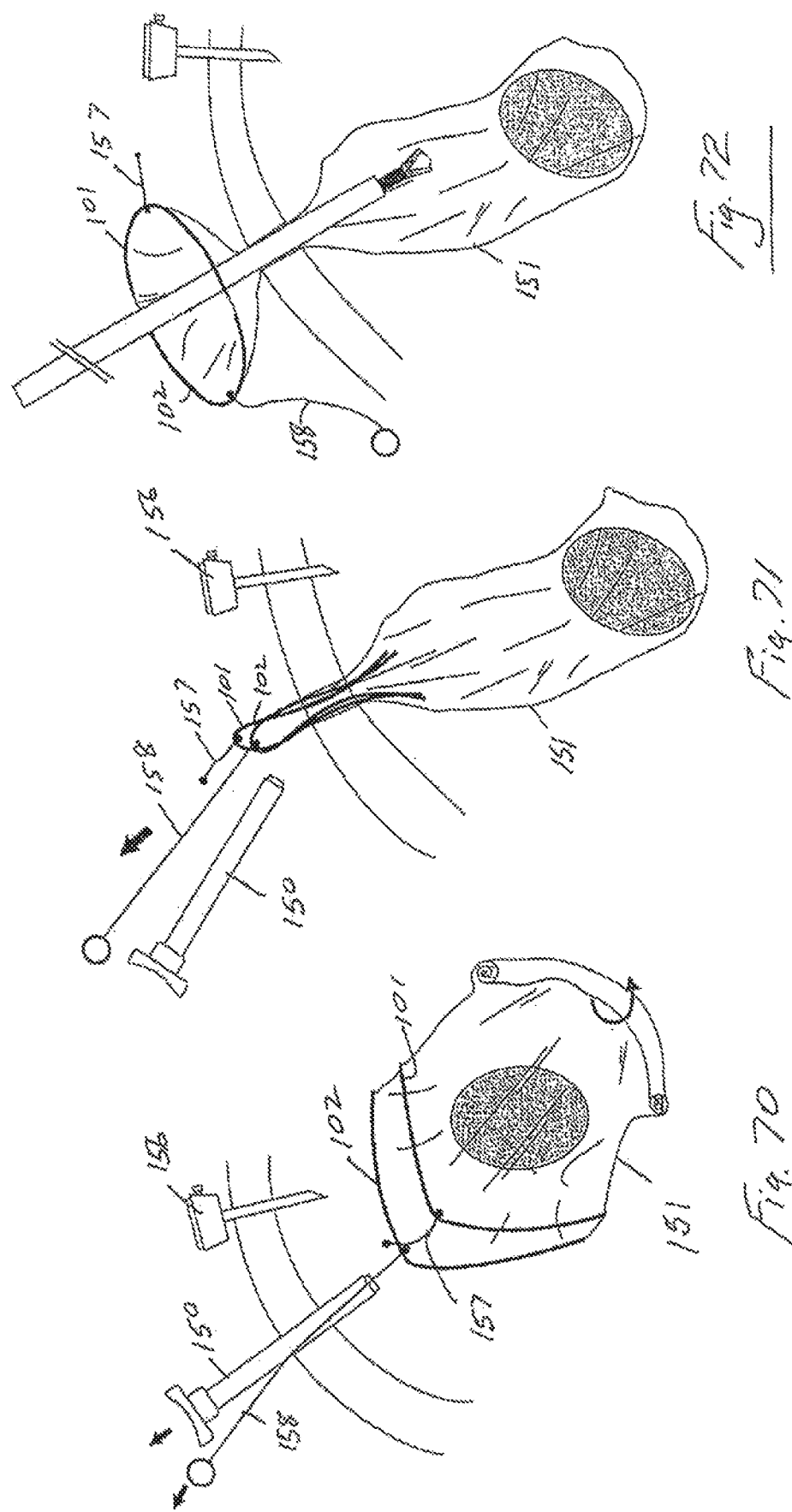

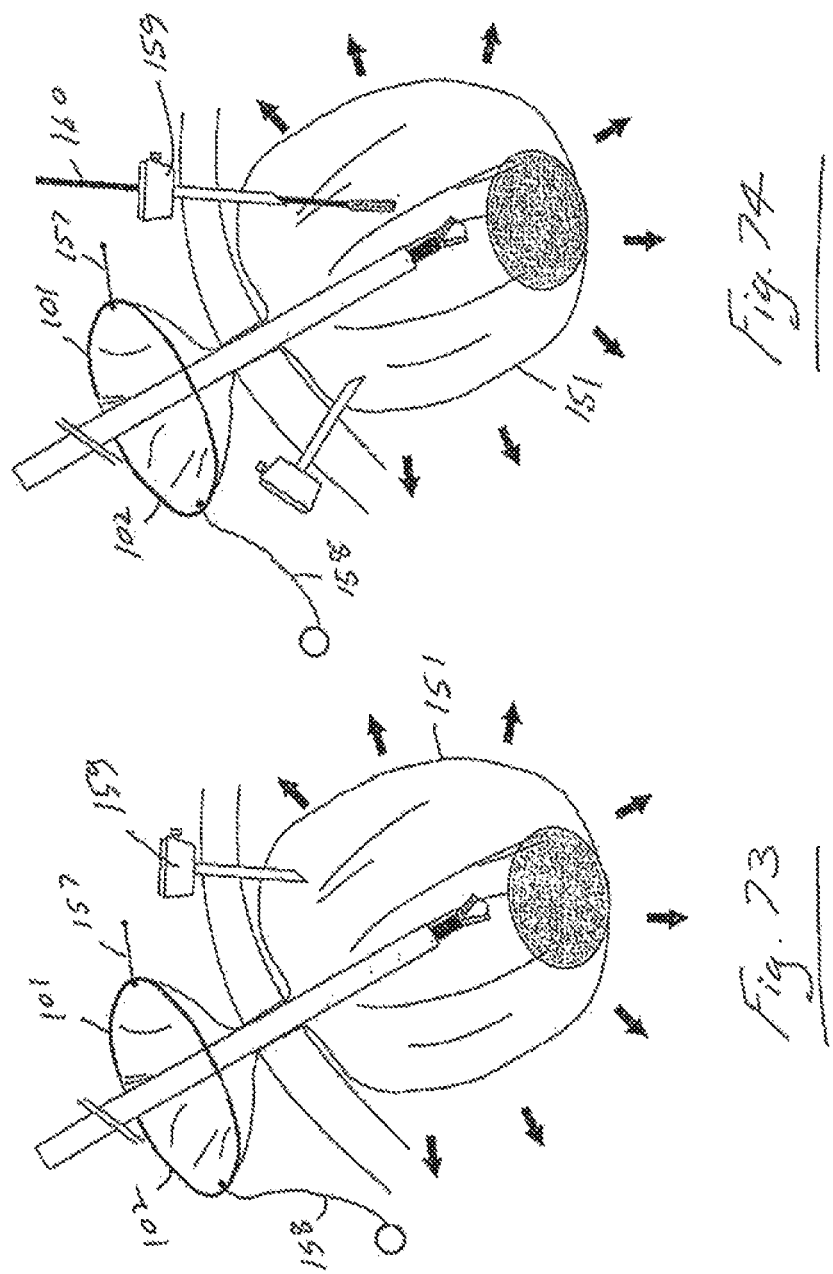

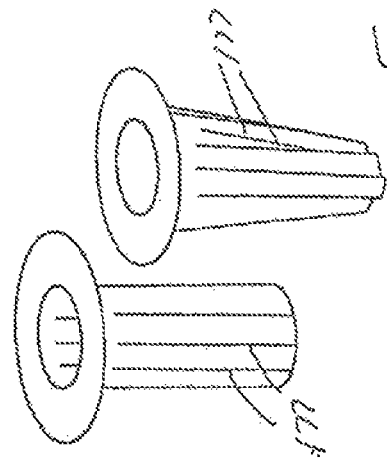
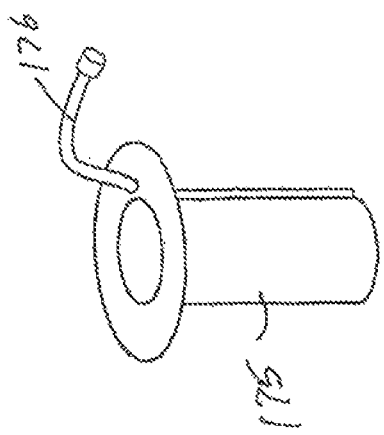
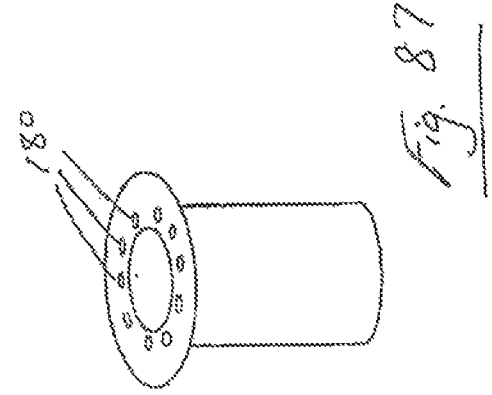
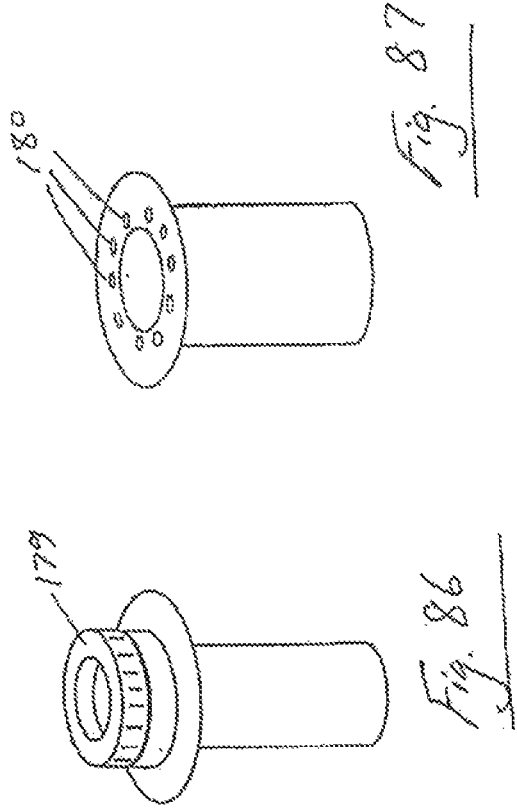
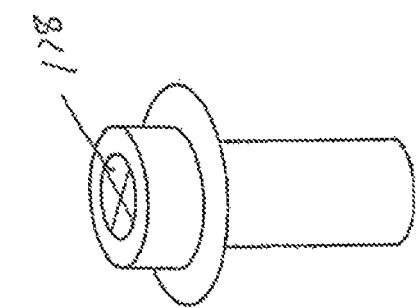

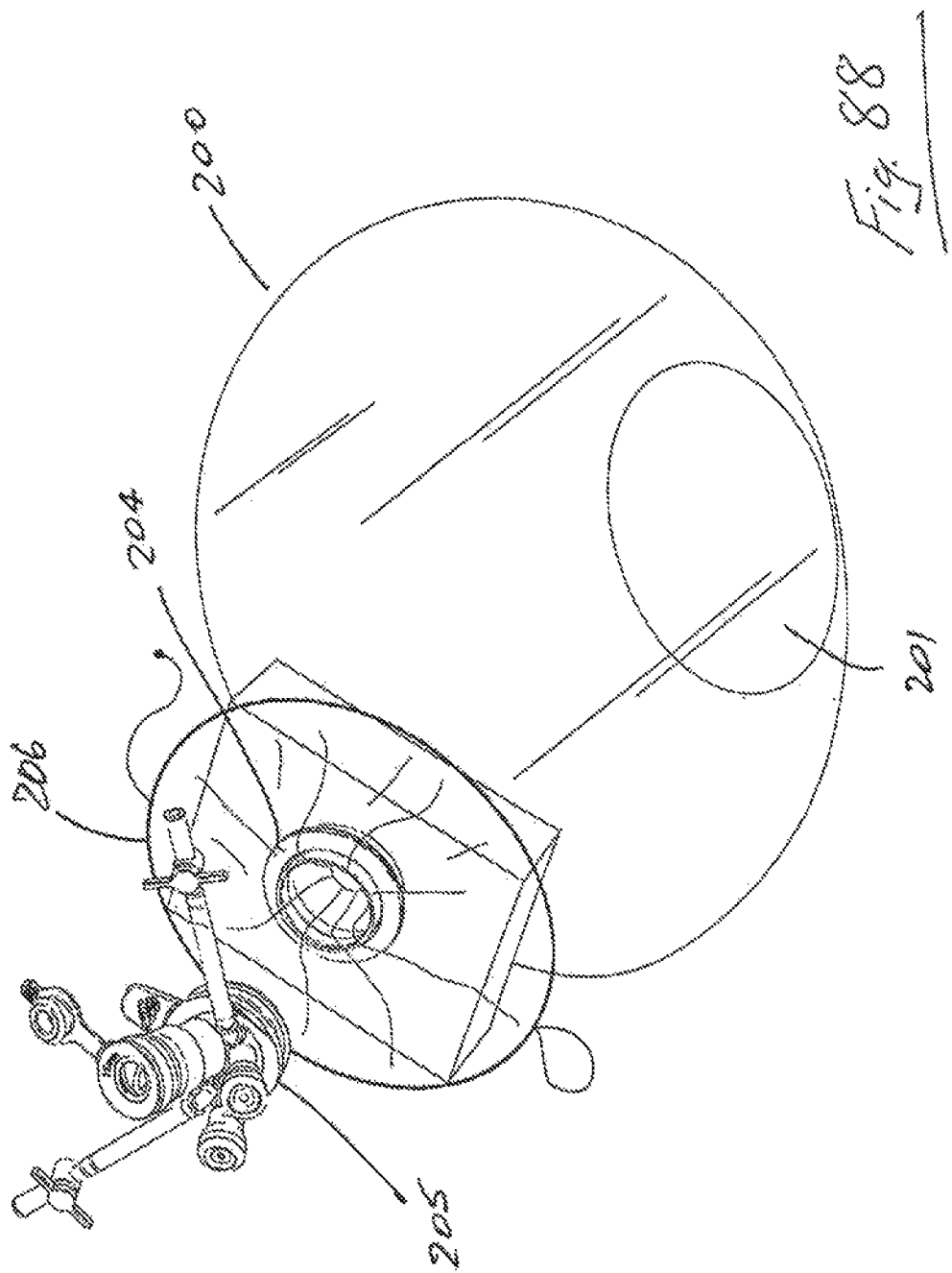

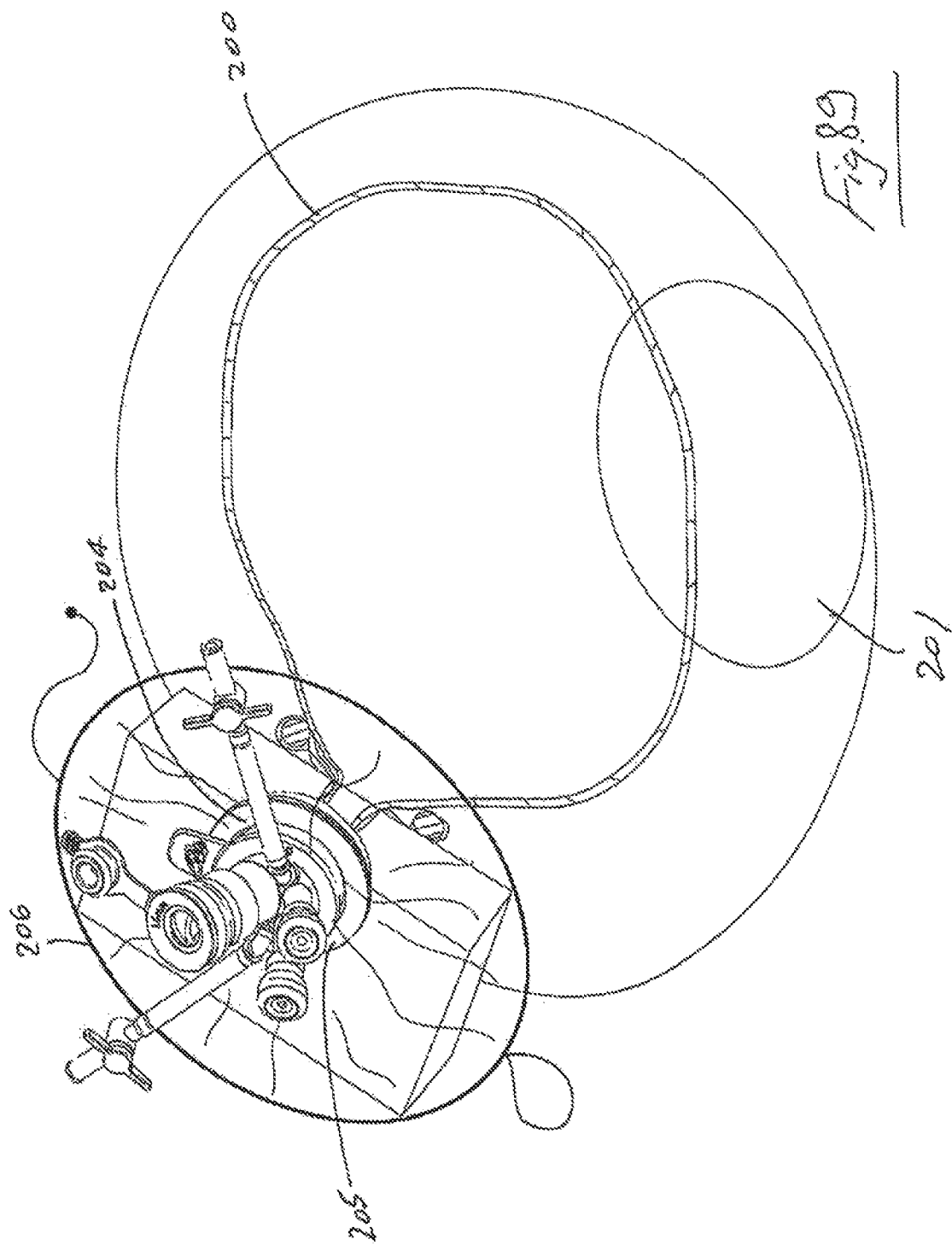

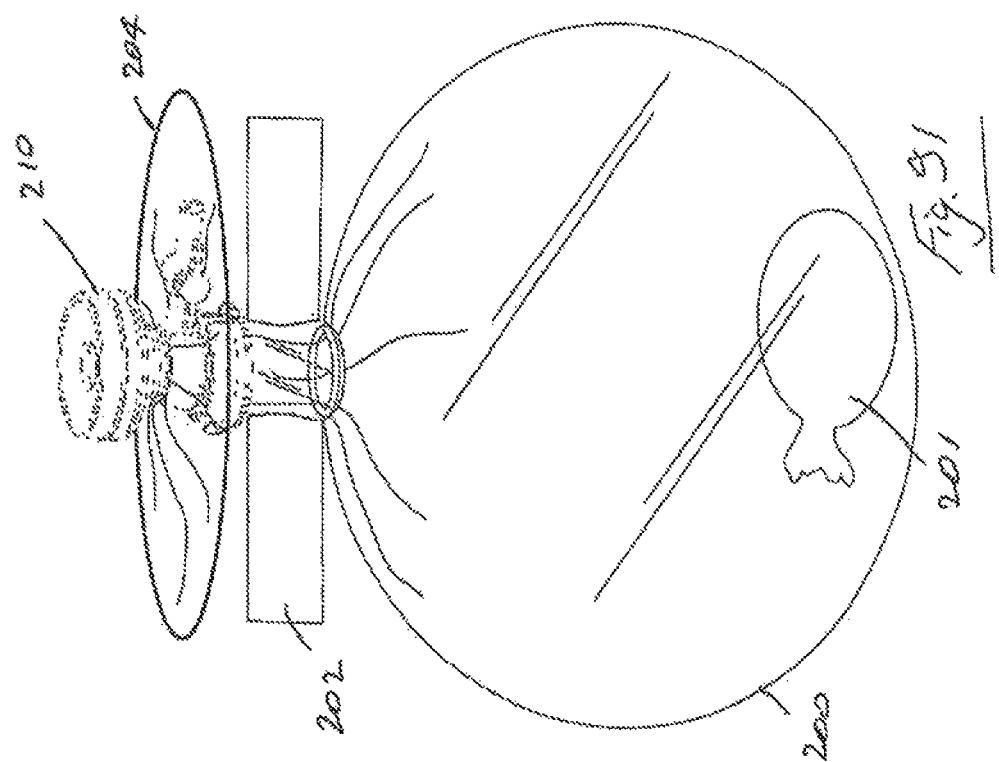
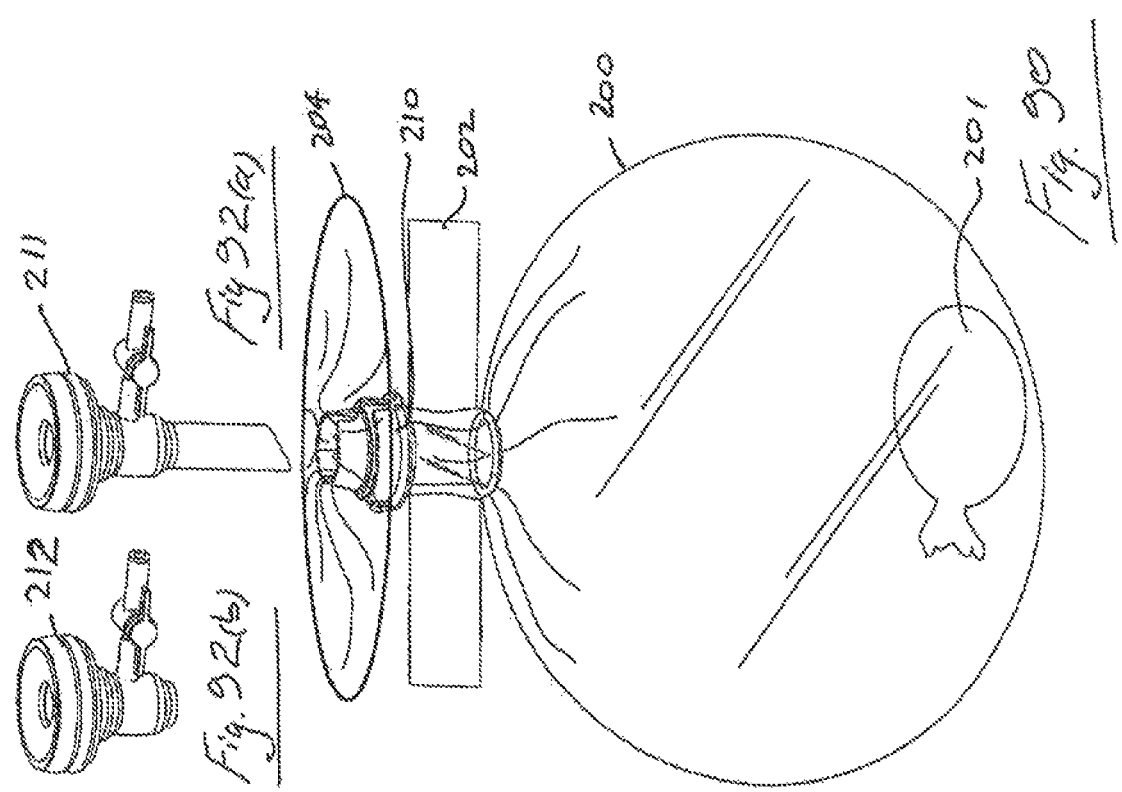

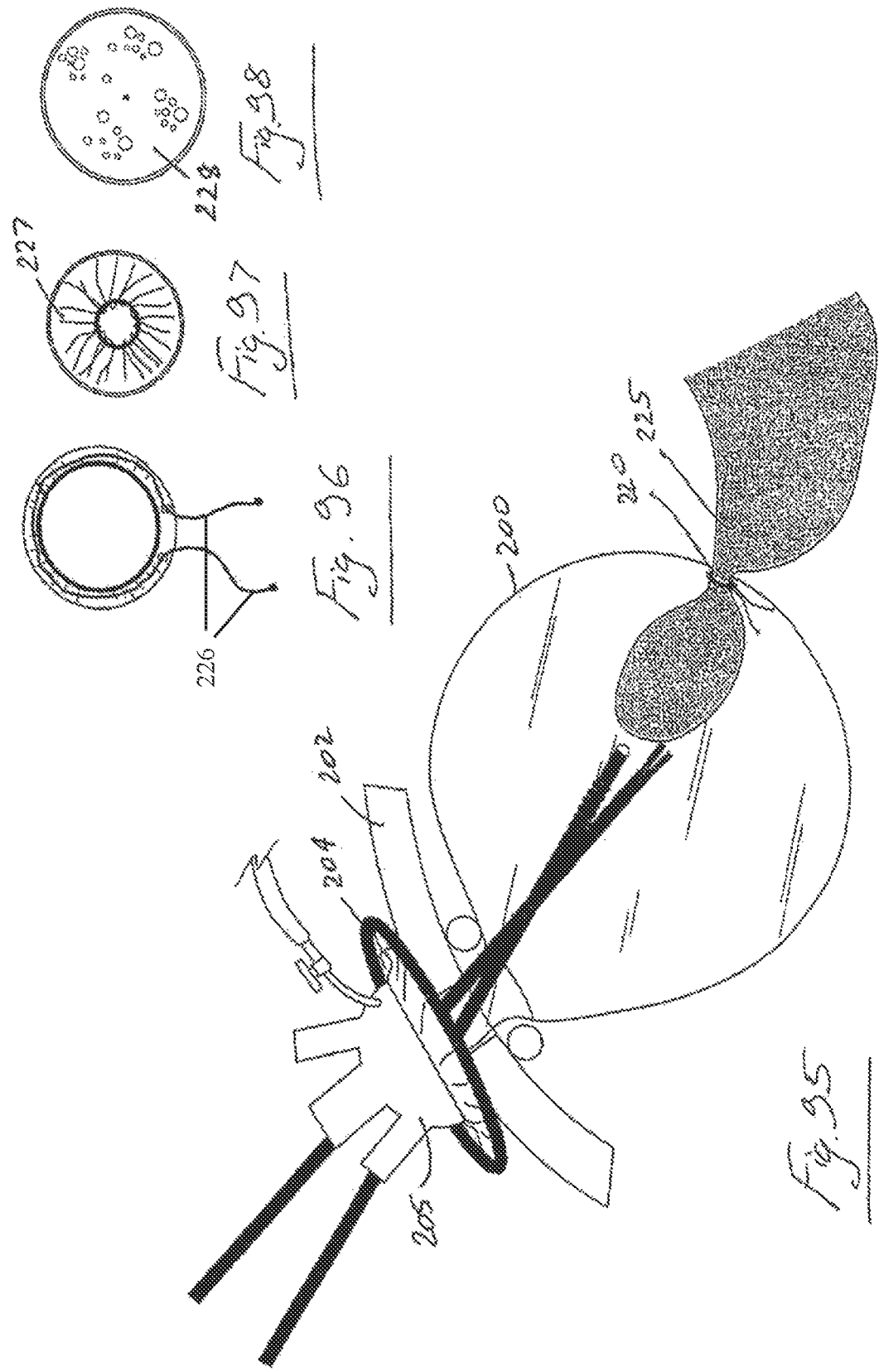

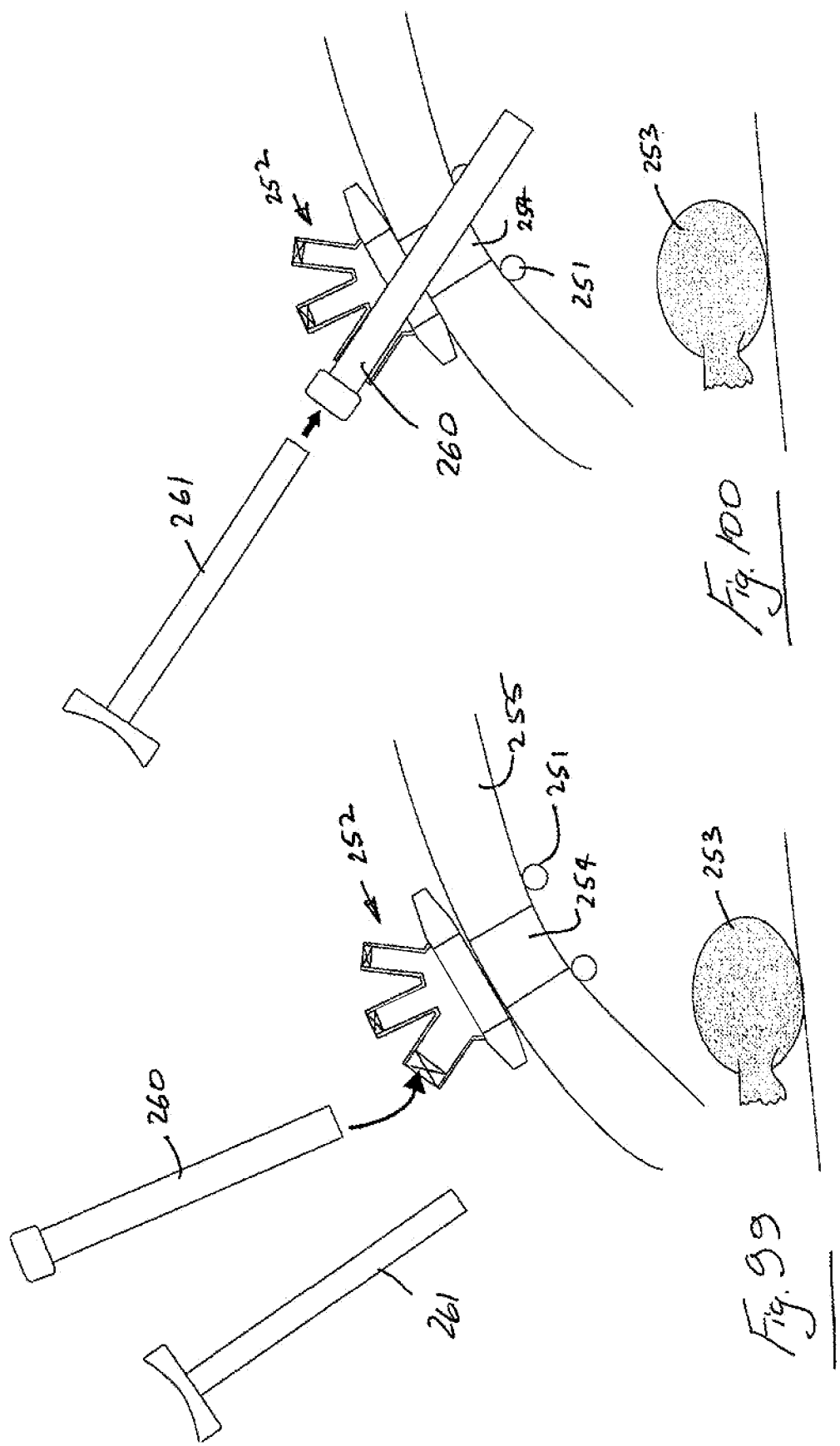

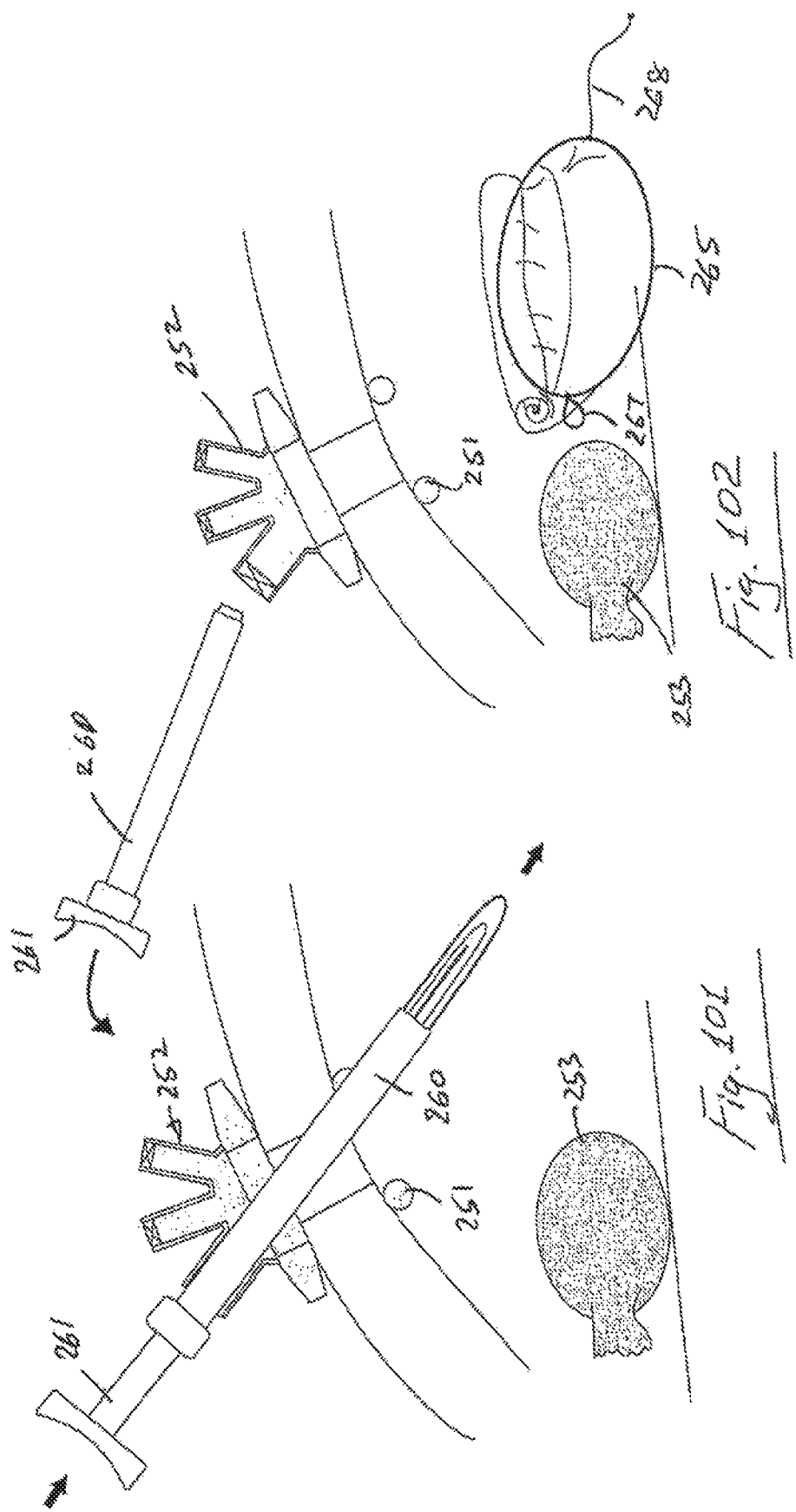

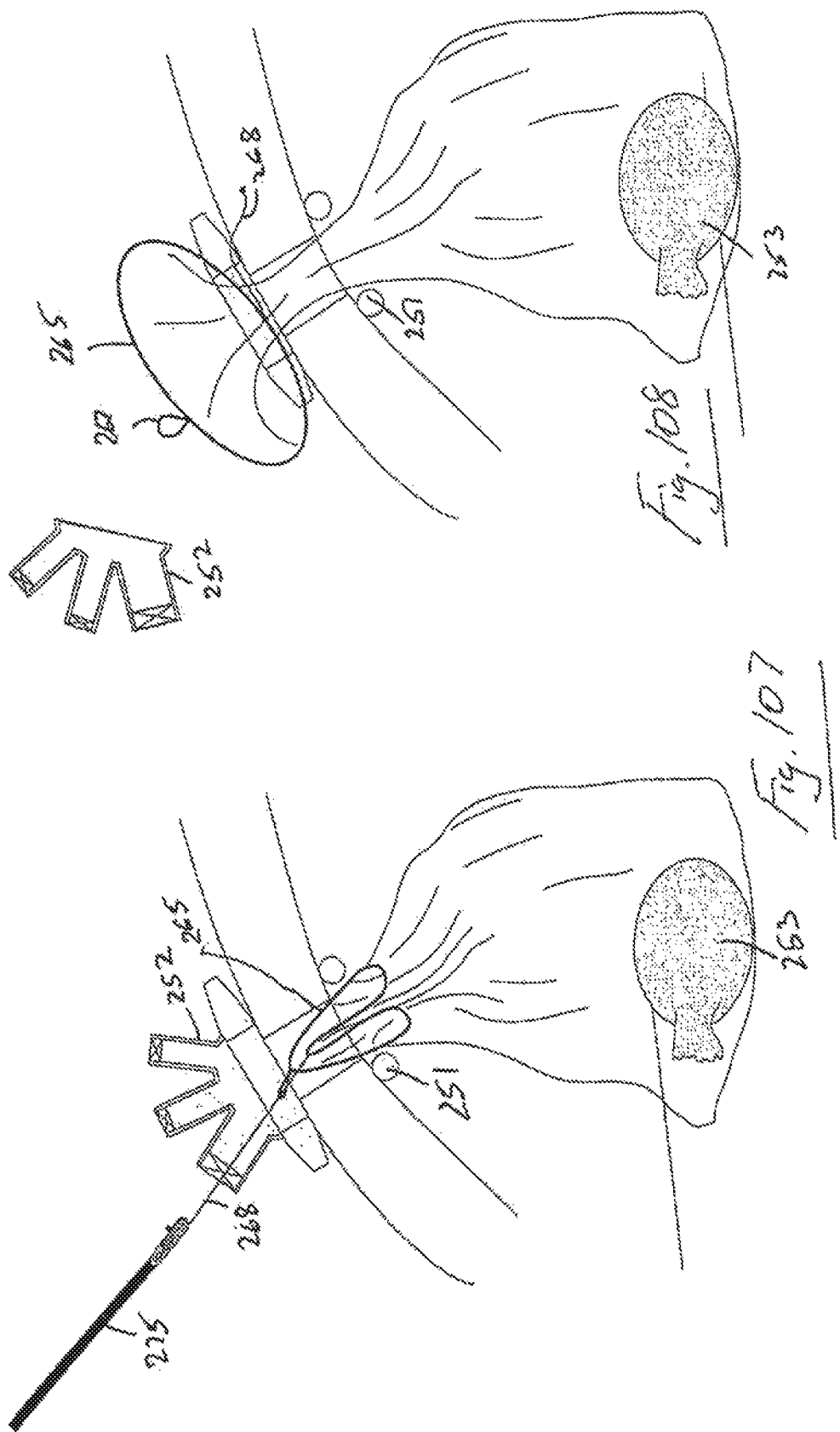

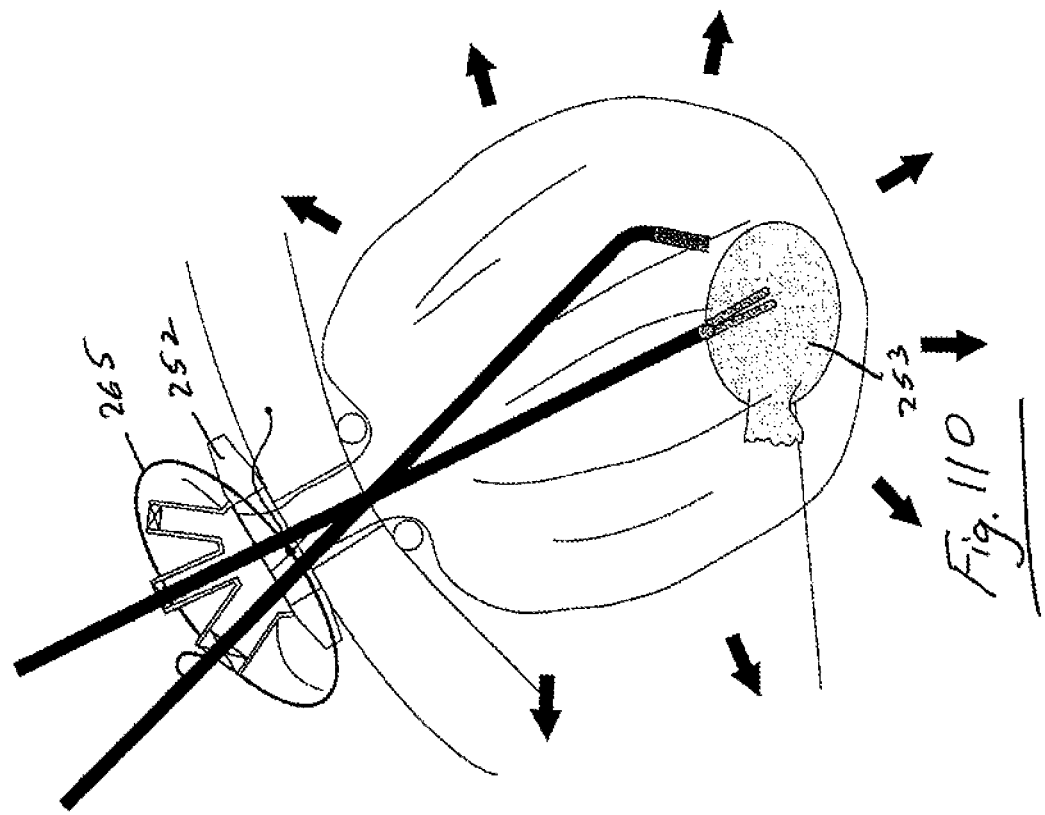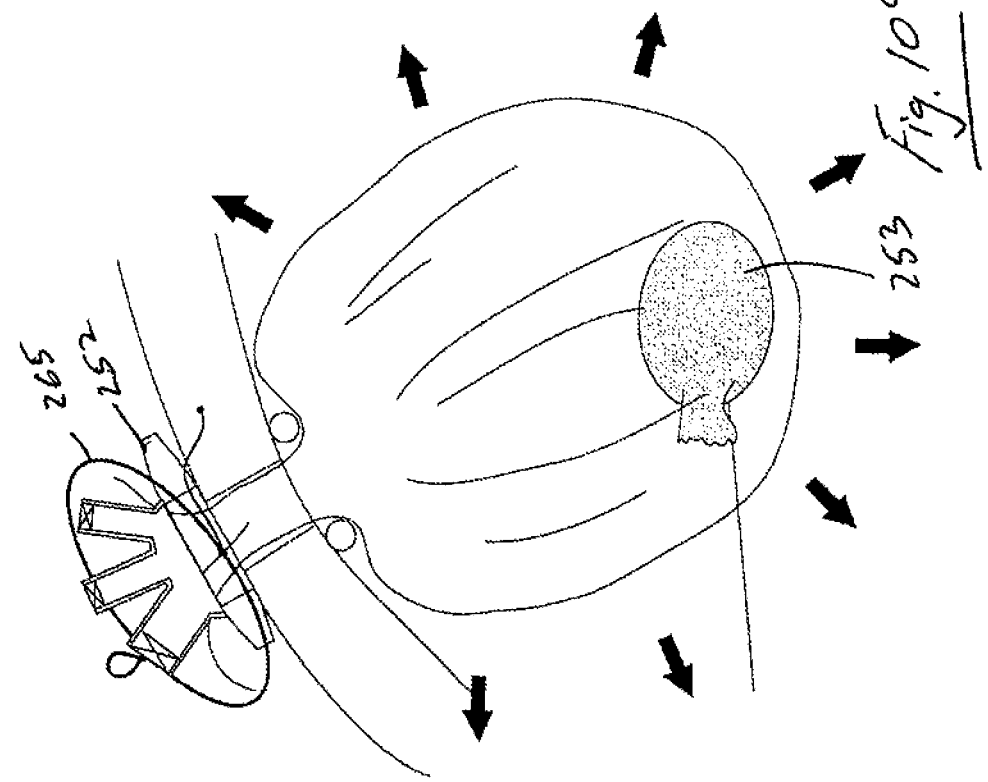

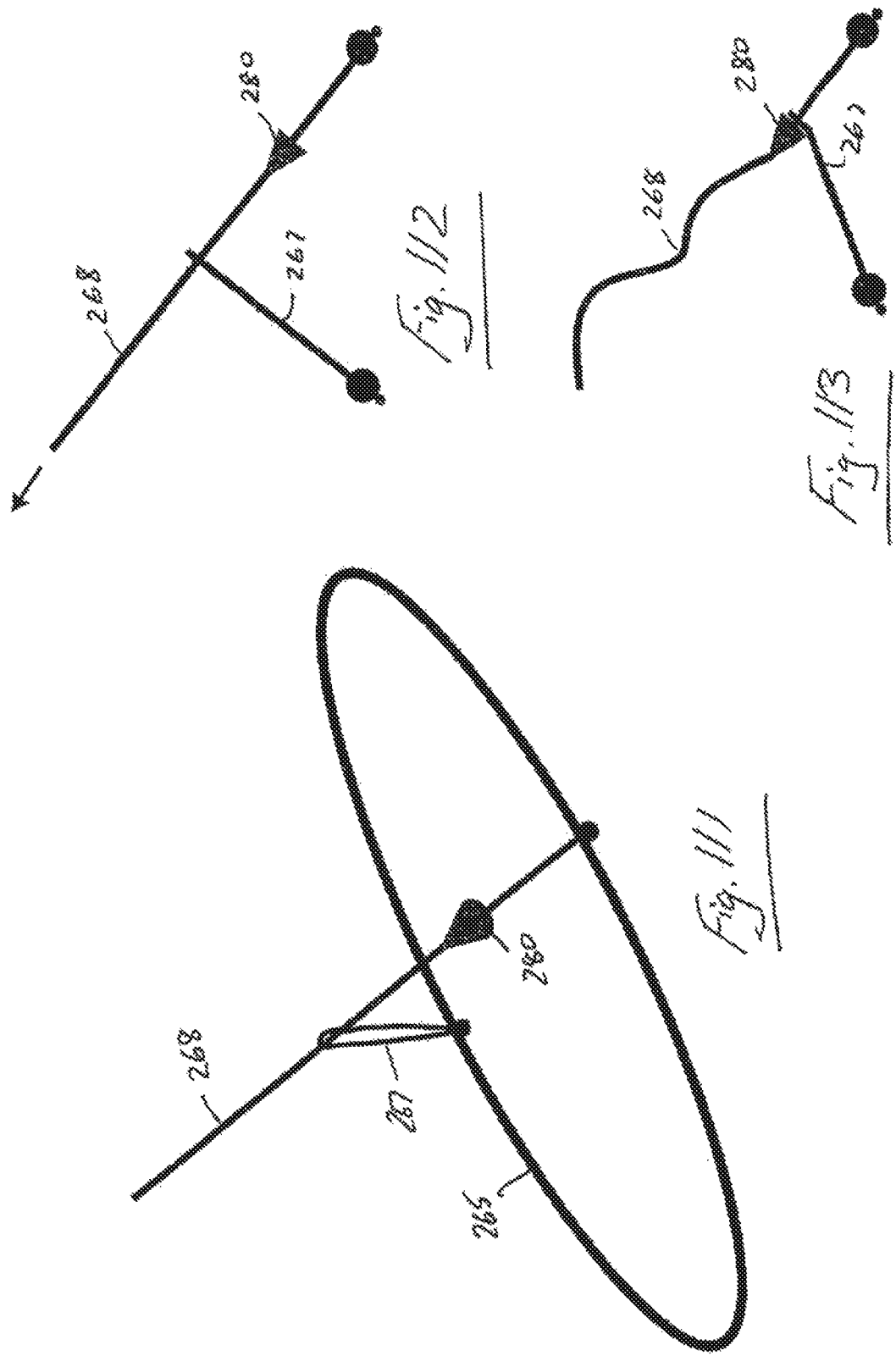

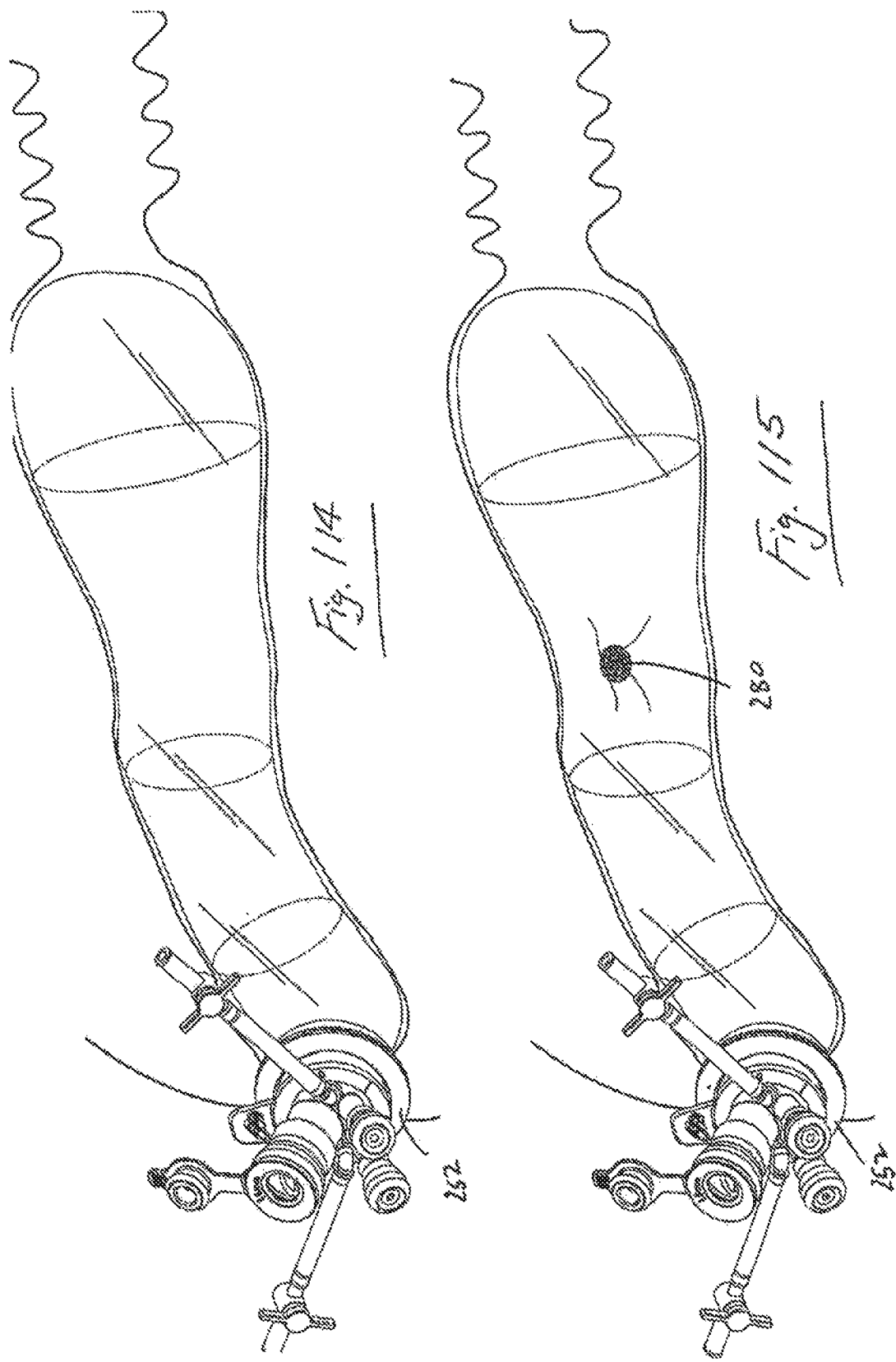

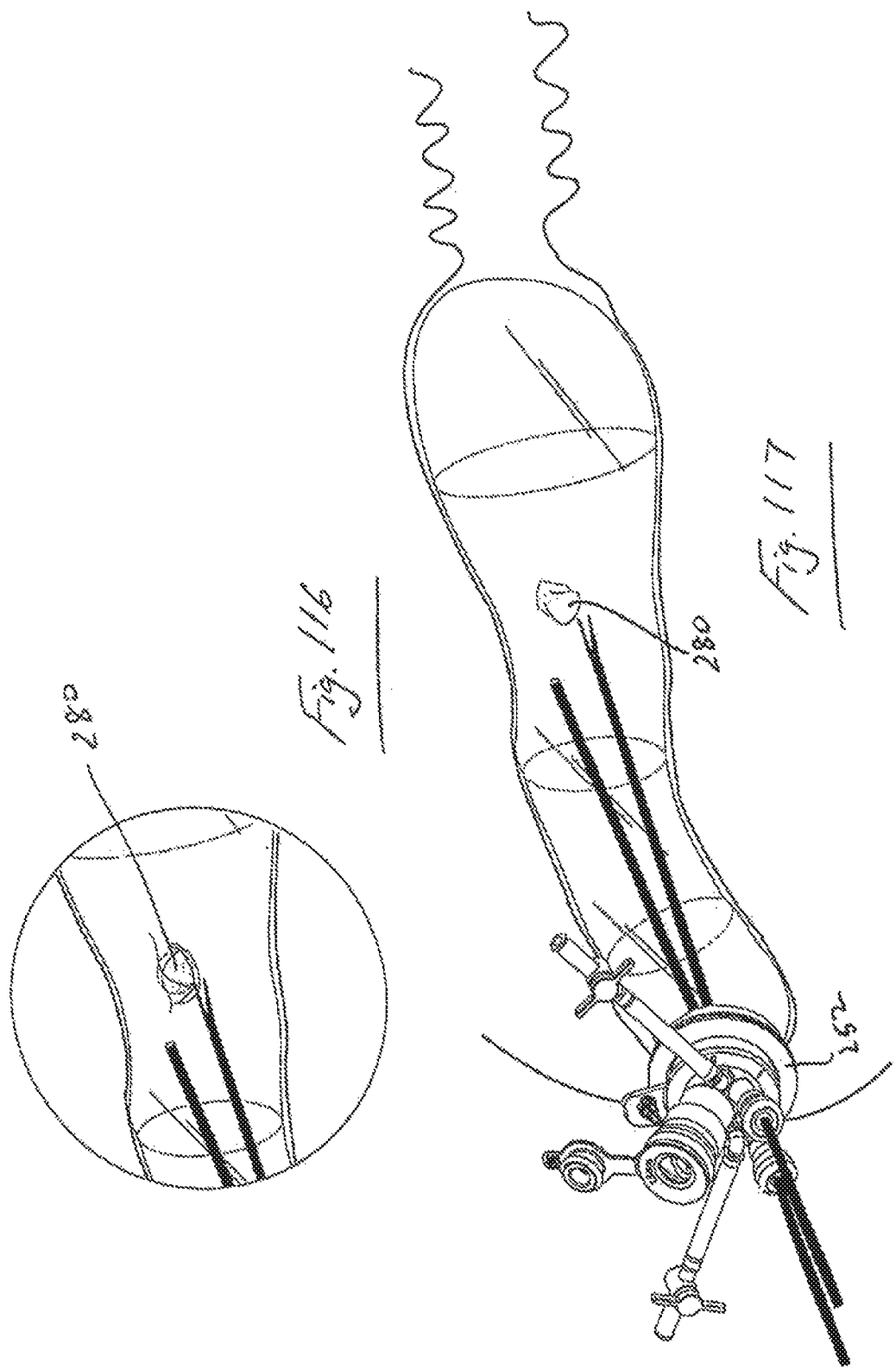

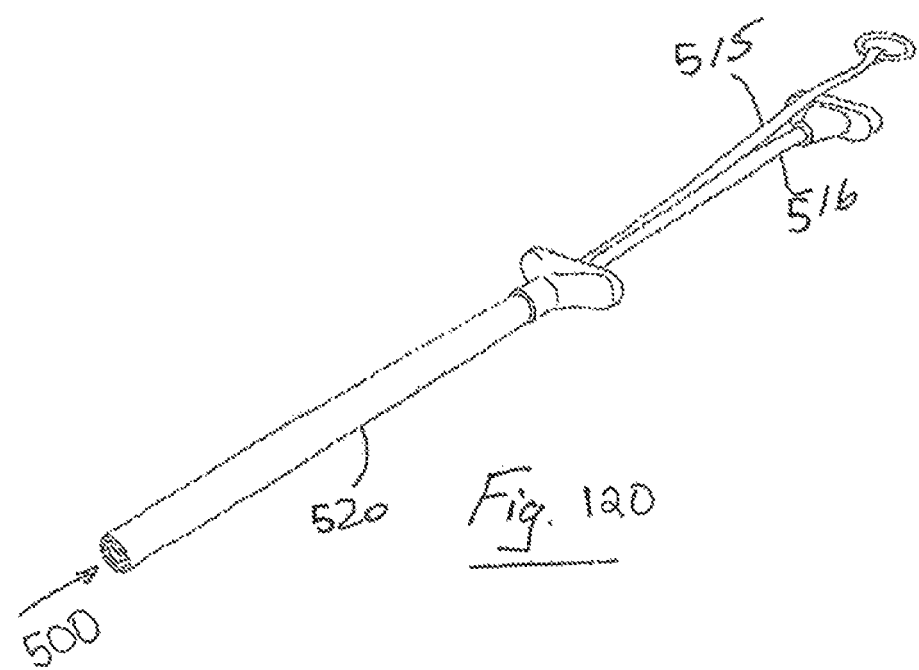
Fig. 120
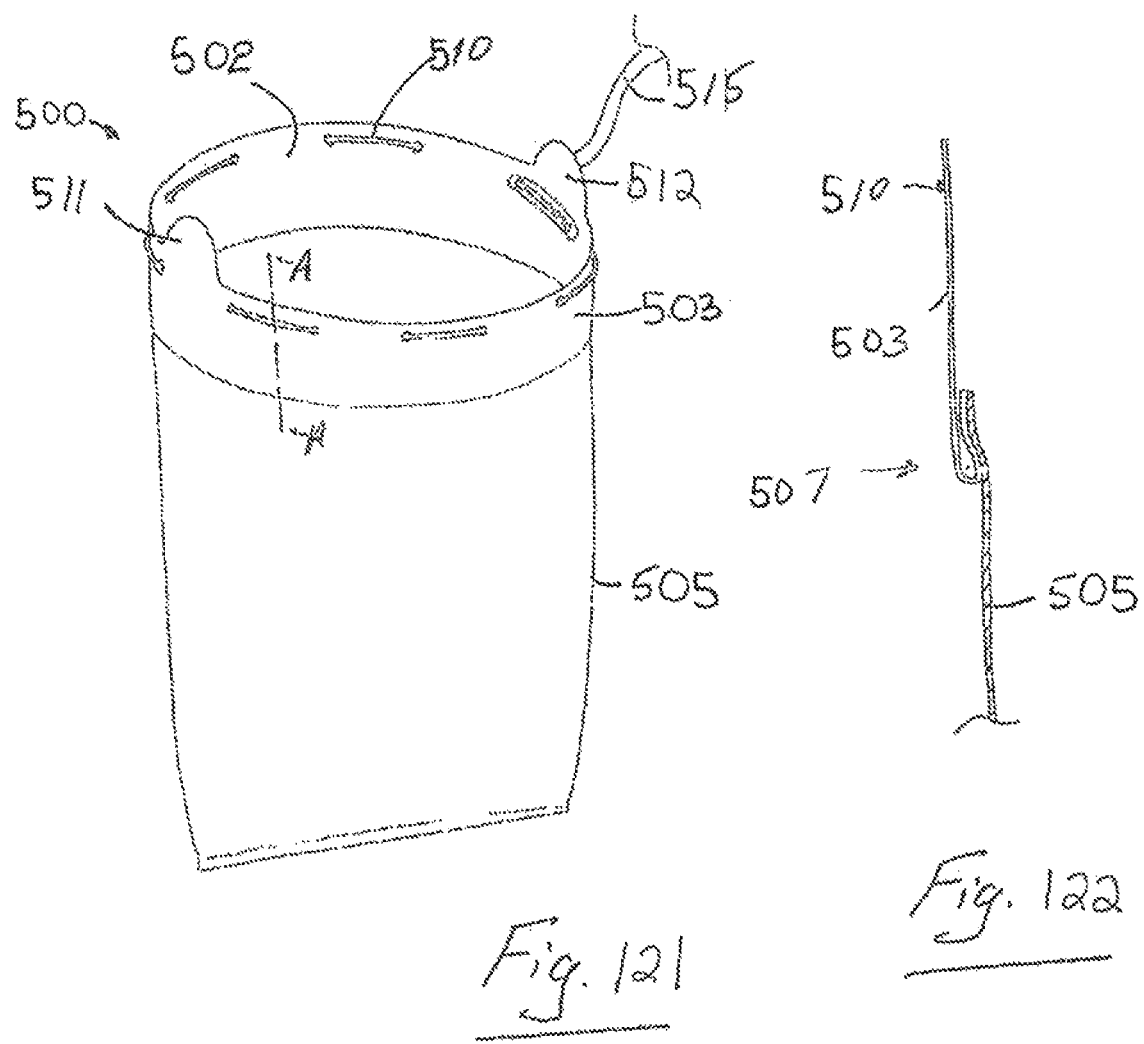
Fig. 121
Fig. 122

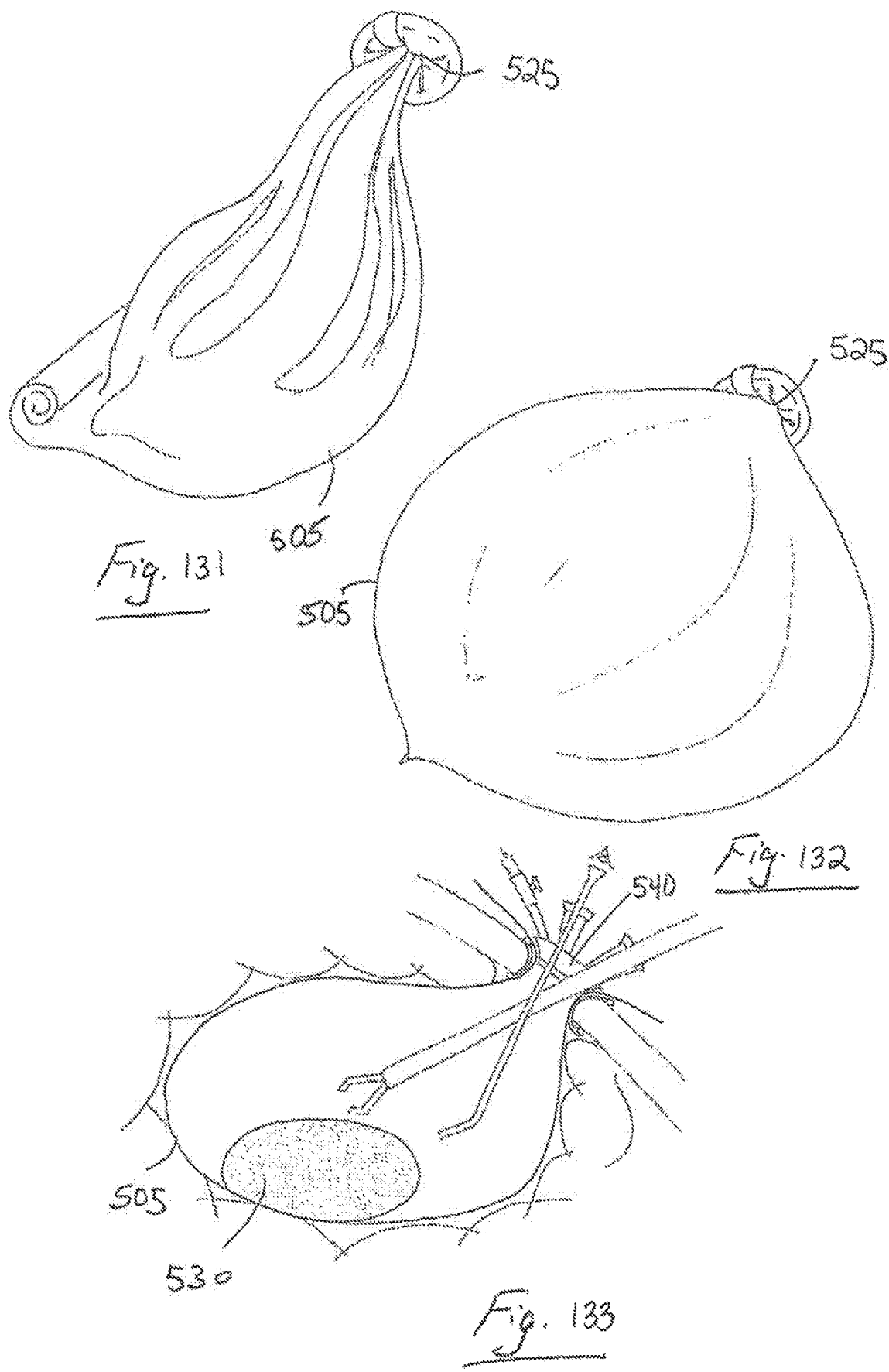

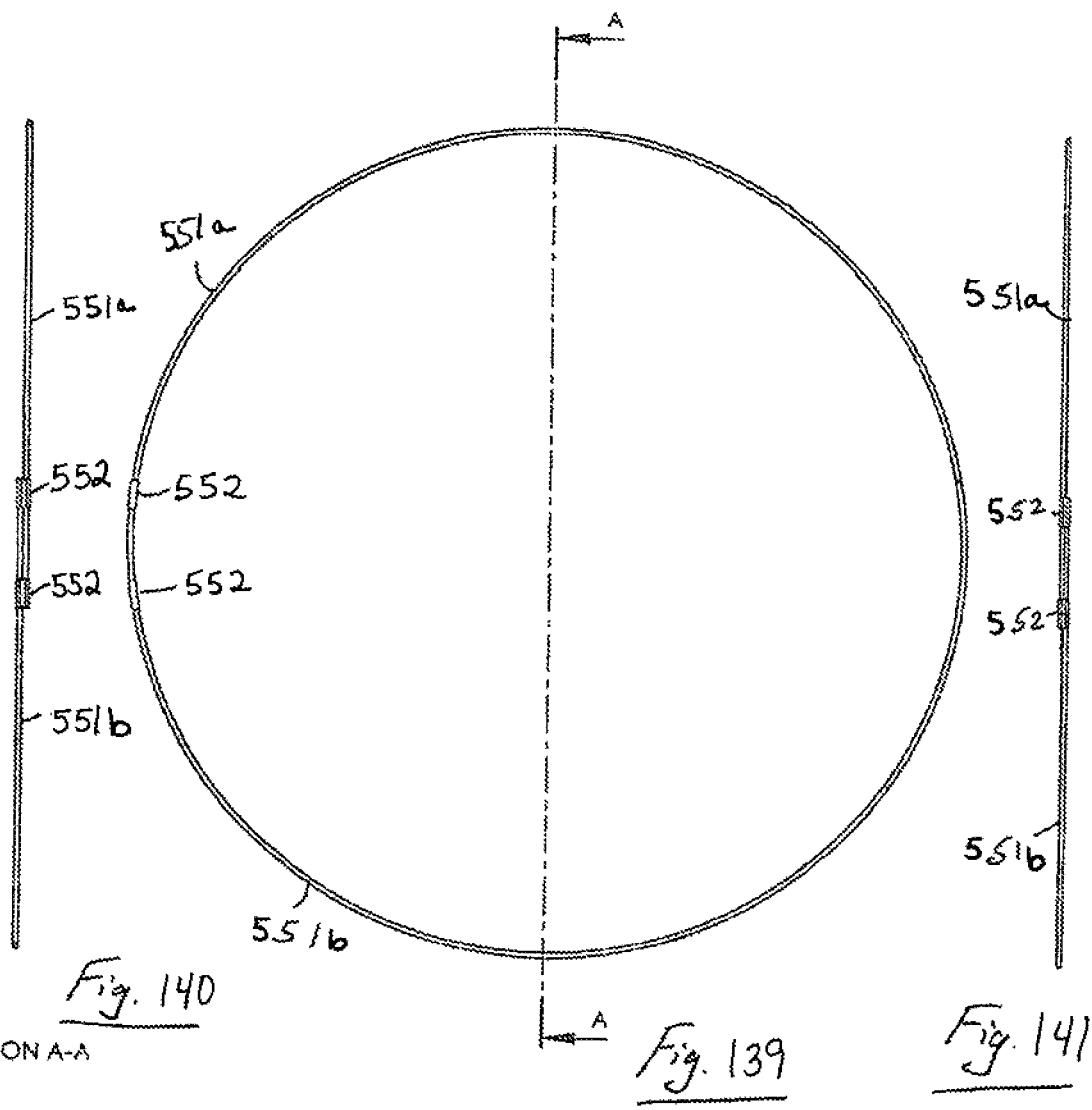
Fig. 140
SECTION A-A
Fig. 139
Fig. 141
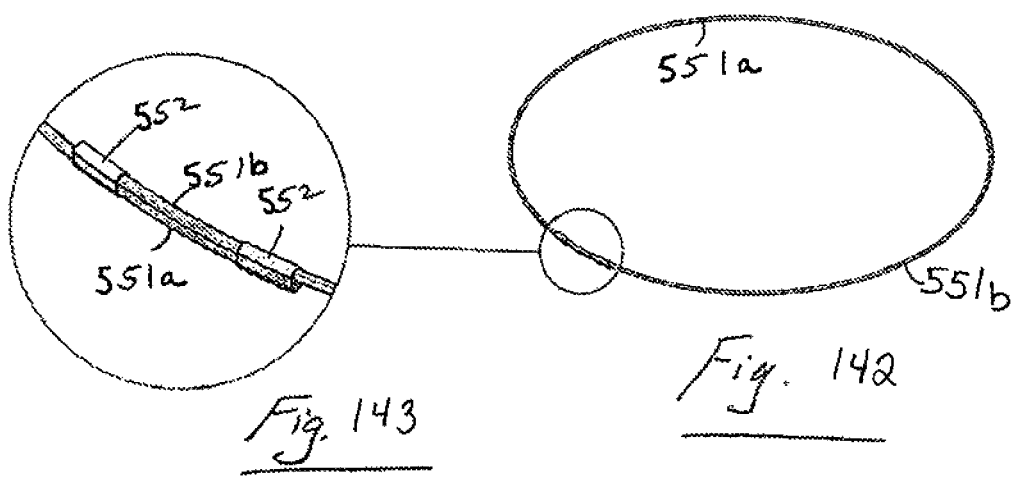
Fig. 143
Fig. 142

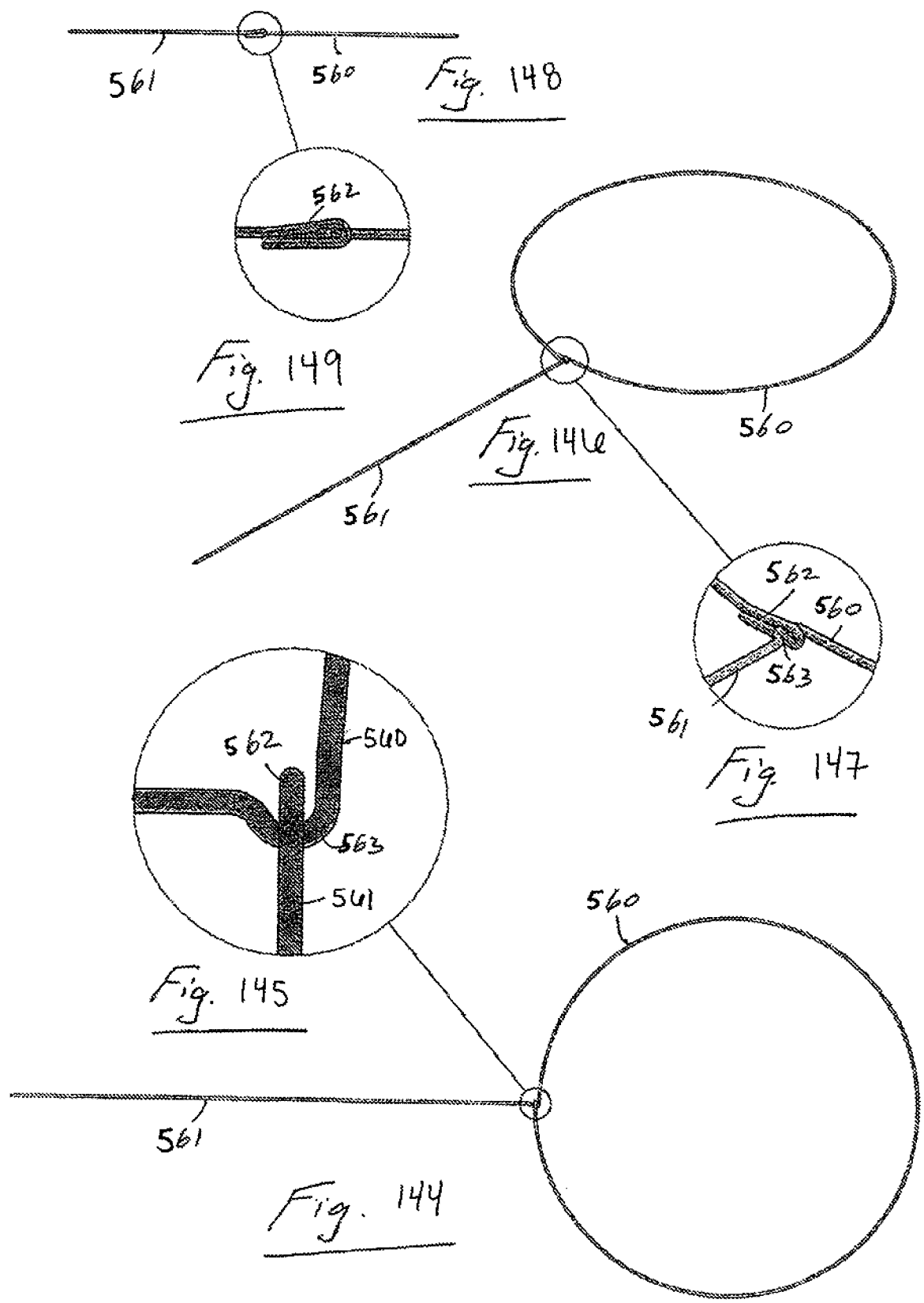

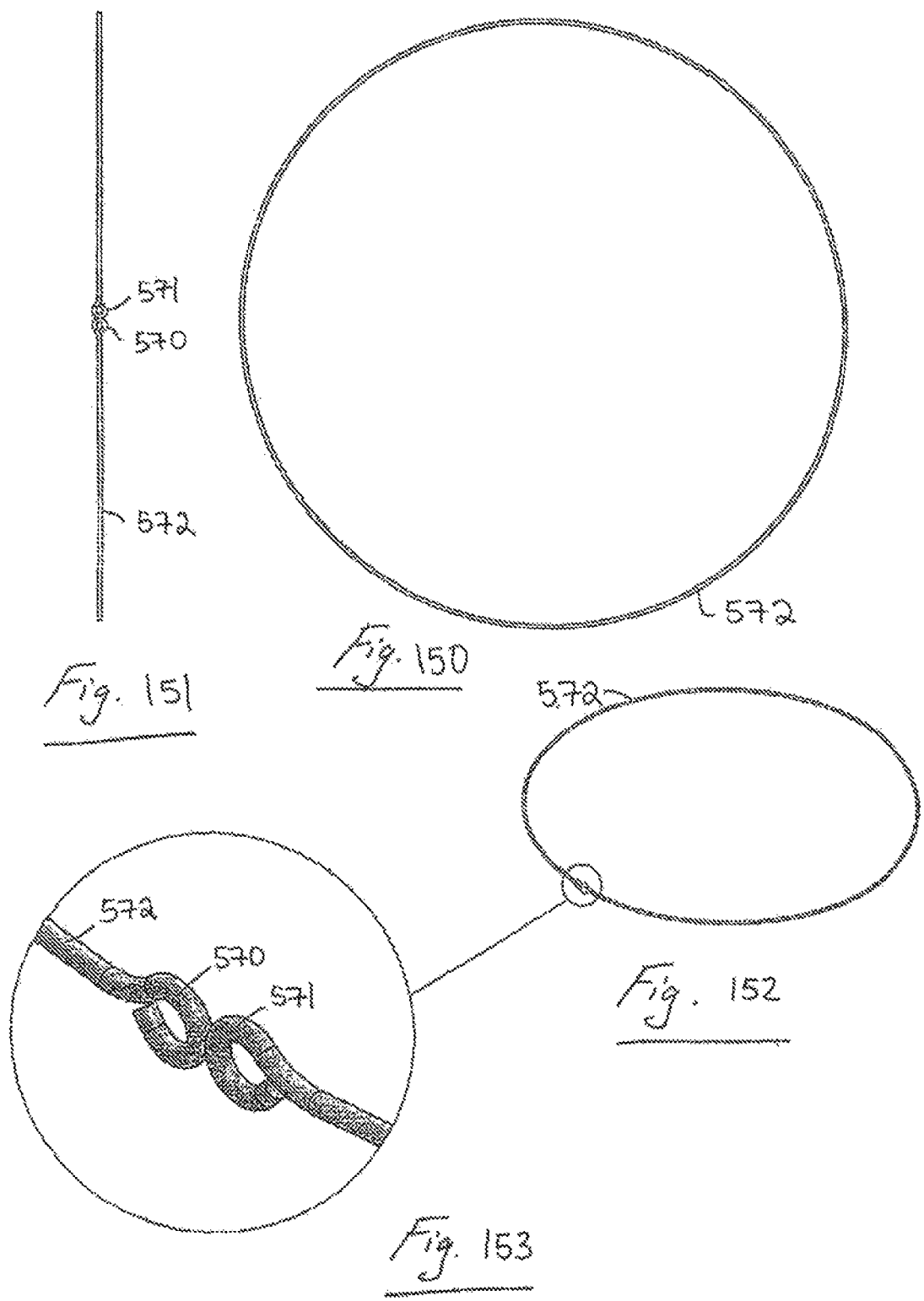

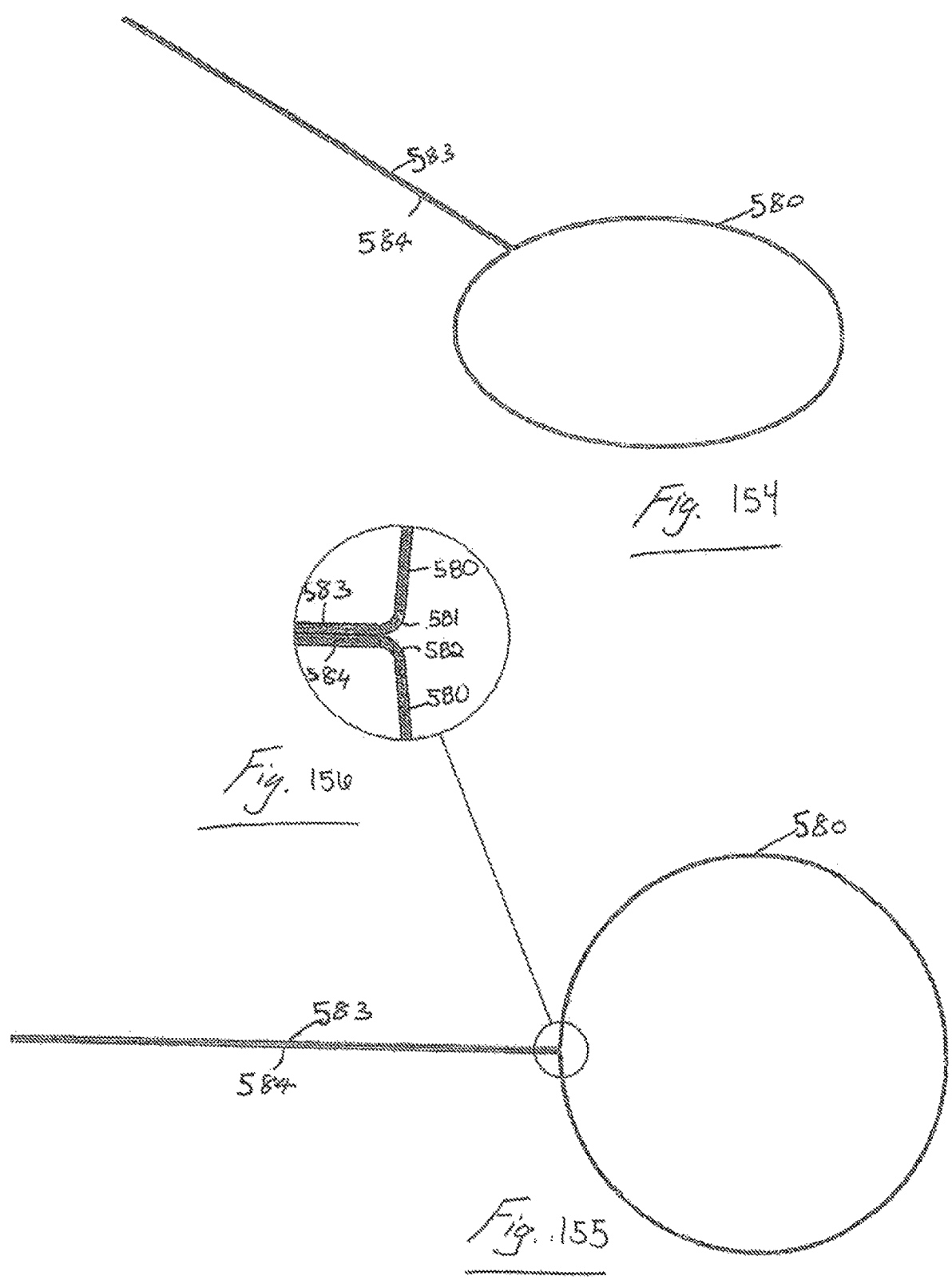

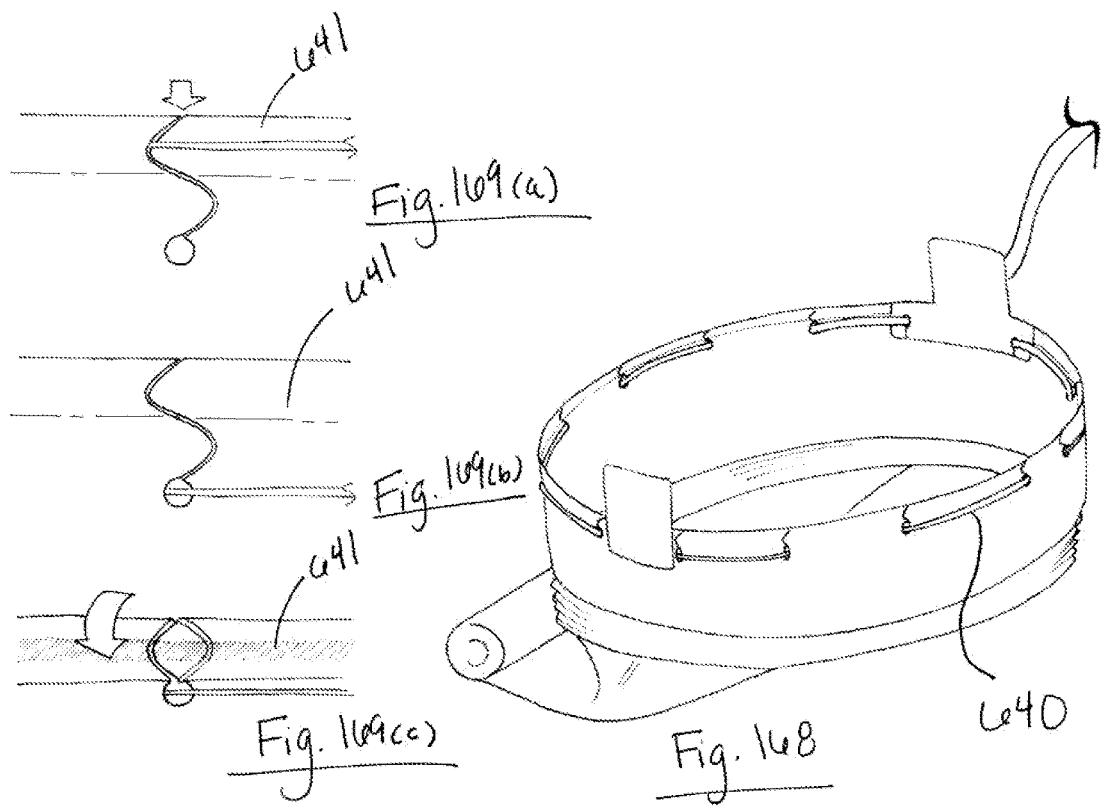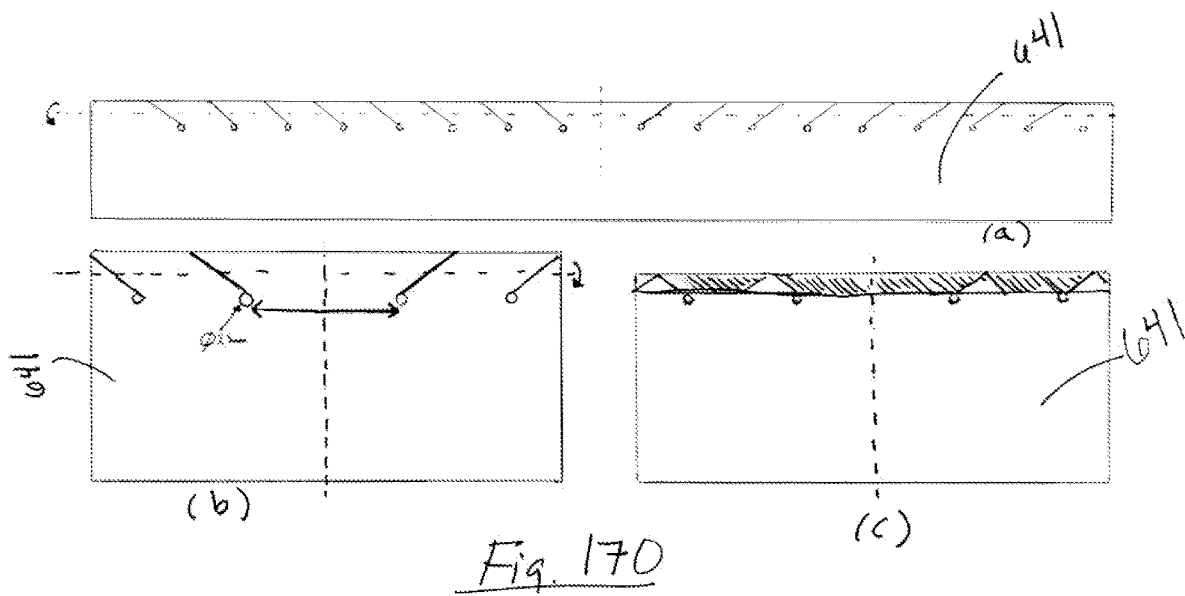

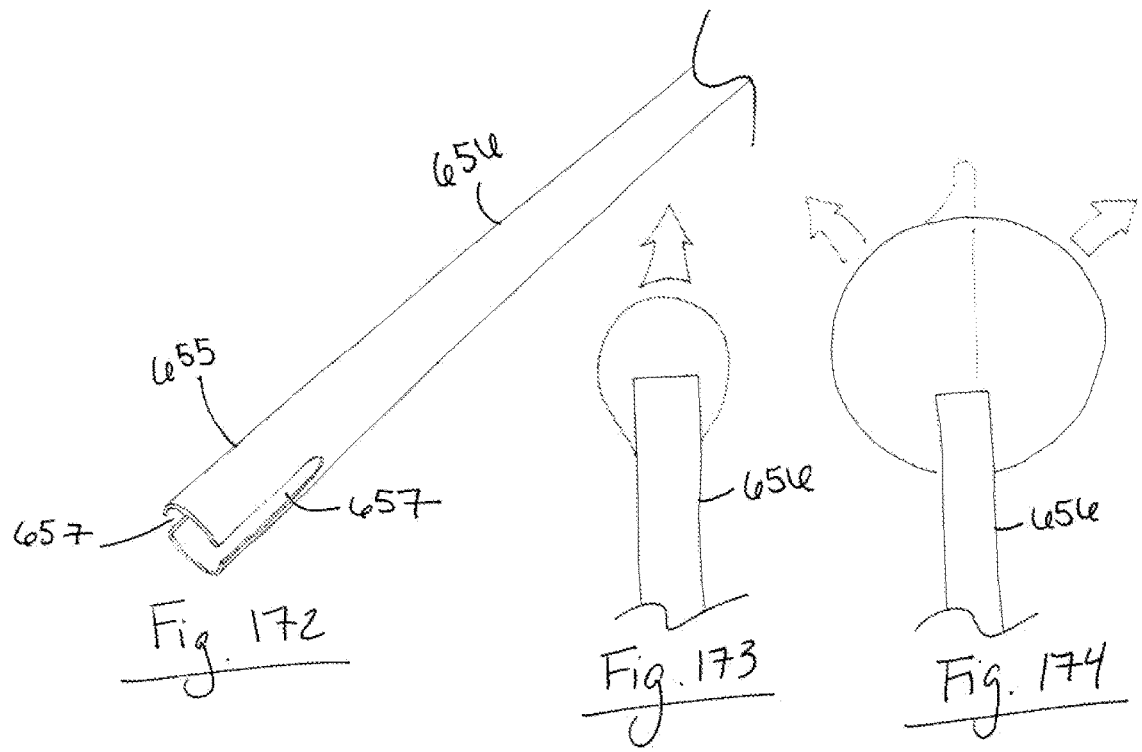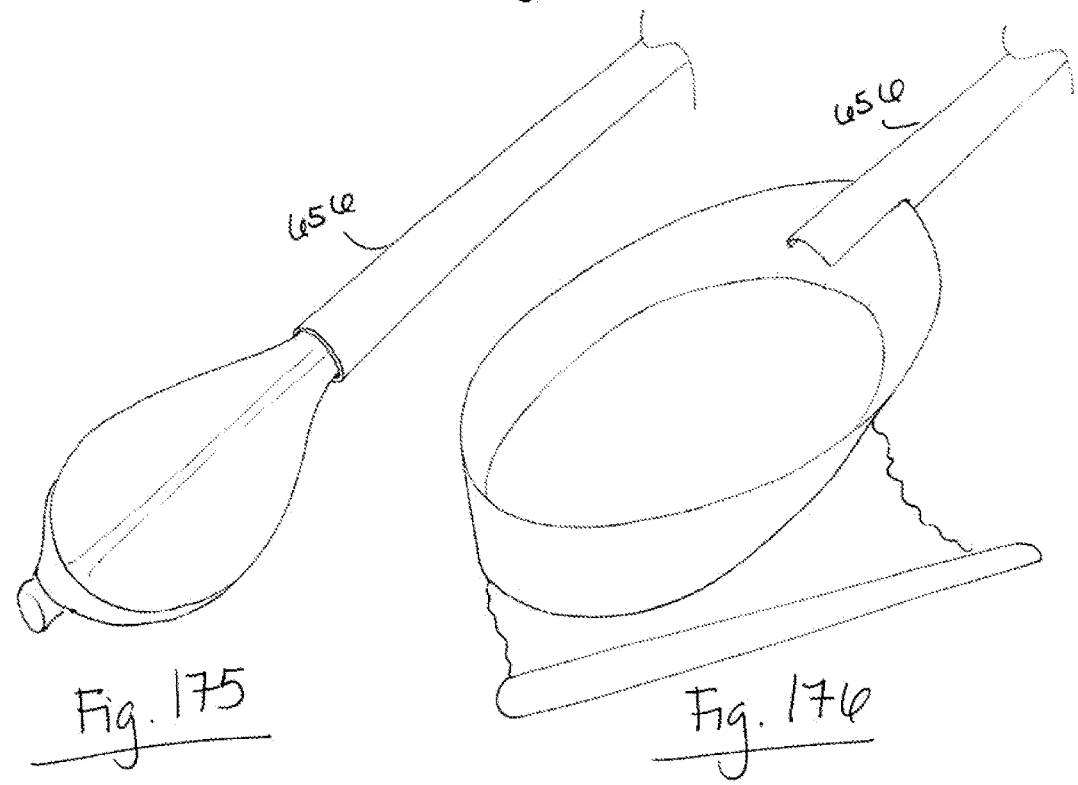

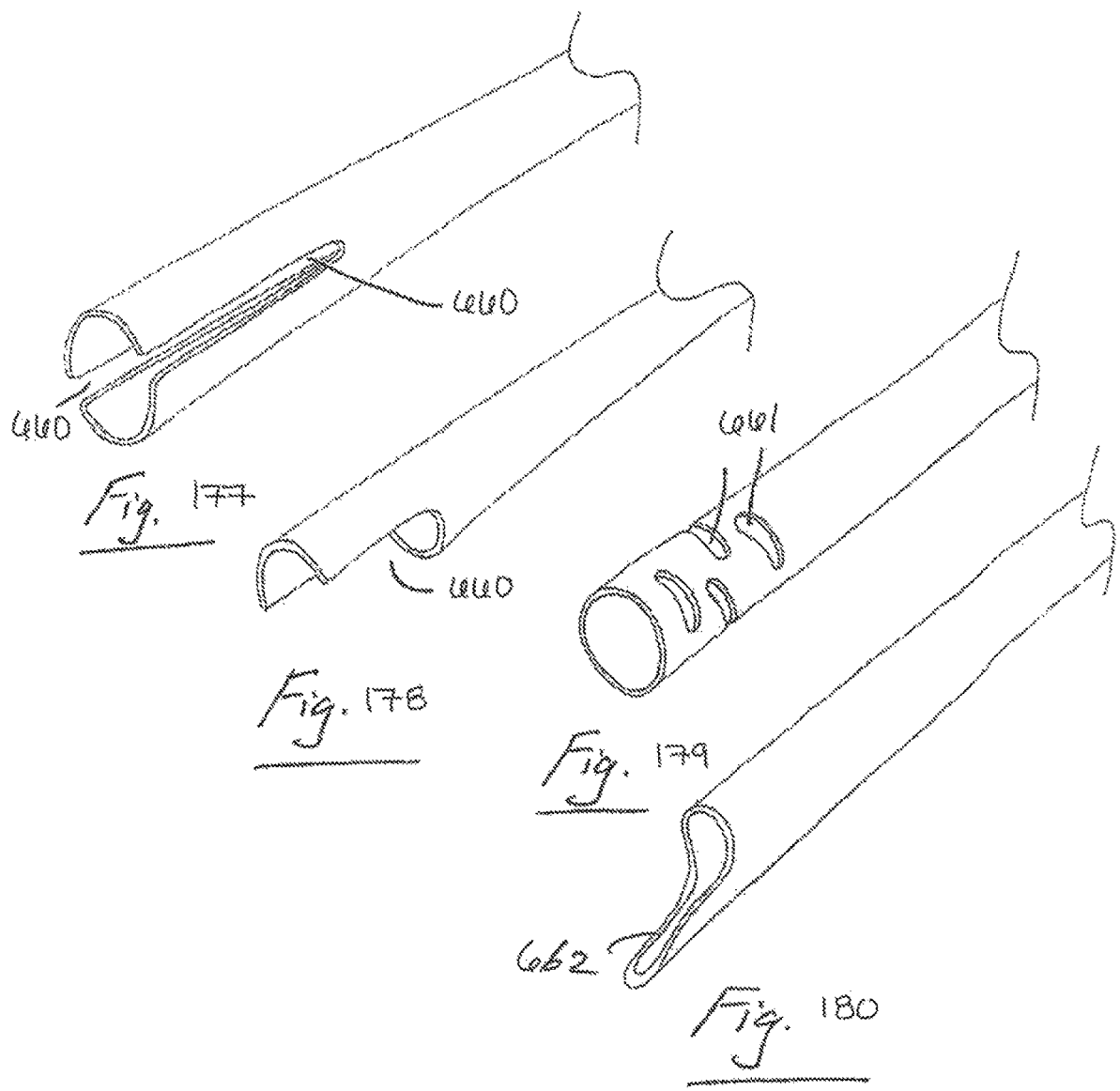

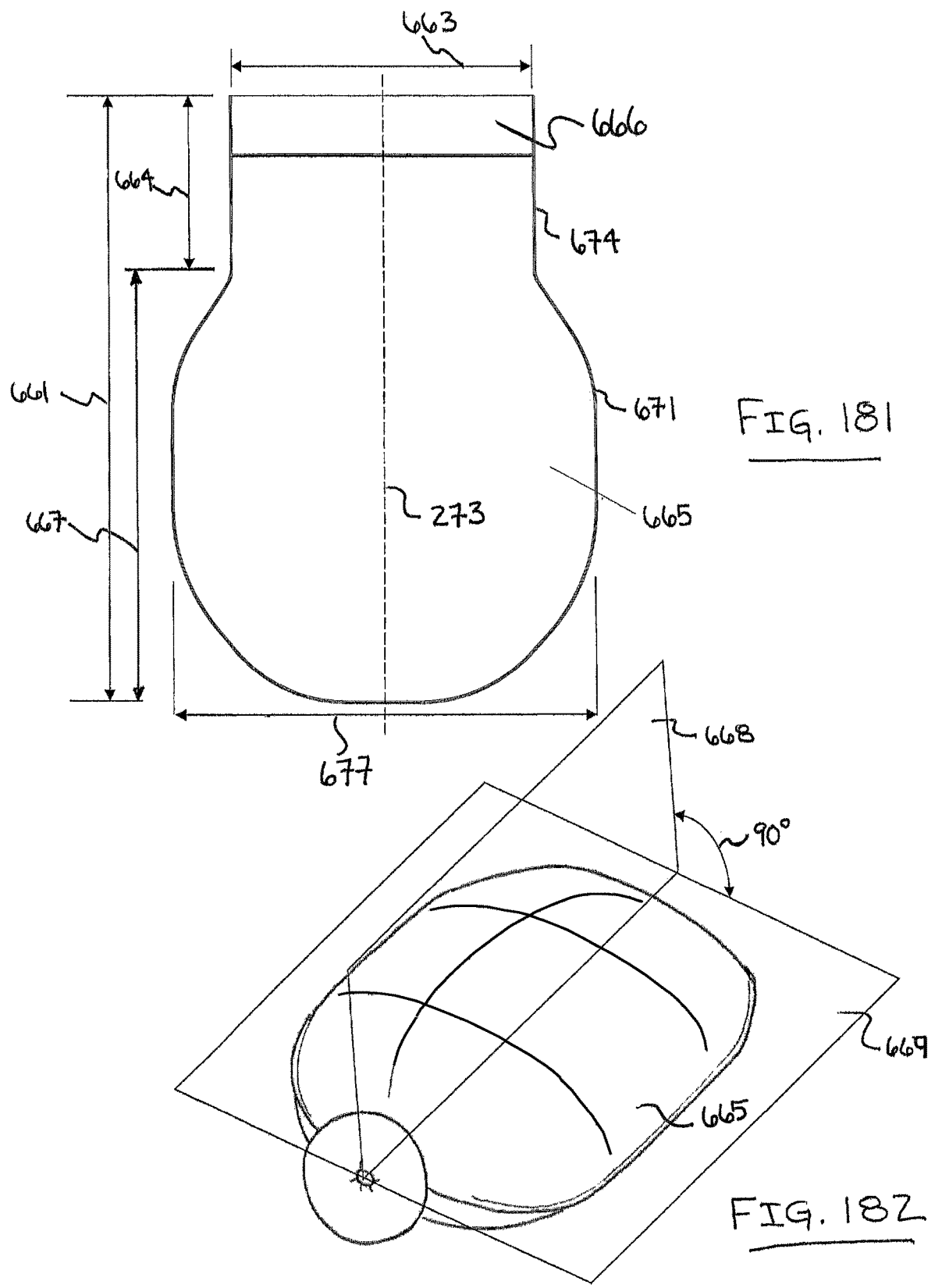

PNEUMOPERITONEUM DEVICE

CROSS-REFERENCE TO RELATED APPLICATIONS

This application is a Continuation of U.S. application Ser. No. 14/996,610, filed Jan. 15, 2016, which is a Continuation of U.S. application Ser. No. 14/584,865, filed Dec. 29, 2014, now U.S. Pat. No. 9,265,492, which is a Continuation of U.S. application Ser. No. 14/251,362, filed Apr. 11, 2014, now U.S. Pat. No. 8,920,431, which is a Continuation-in-Part of U.S. application Ser. No. 13/725,148, filed Dec. 21, 2012, which claims the benefit of U.S. Provisional Patent Application Nos. 61/580,088 filed on Dec. 23, 2011, and 61/742,125 filed on Aug. 3, 2012, the entire contents of all of which are incorporated herein by reference. Additionally, U.S. application Ser. No. 14/251,362 claims the benefit of U.S. Provisional Patent Application Nos. 61/839,461, filed on Jun. 26, 2013, 61/940,681, filed on Feb. 17, 2014, and 61/968,770, filed on Mar. 21, 2014, the entire contents of all of which are incorporated herein by reference.

INTRODUCTION

This invention relates to a pneumoperitoneum device. The invention also relates to a method of performing a surgical procedure.

STATEMENTS OF INVENTION

According to the invention there is provided an artificial pneumoperitoneum device (e.g., a bag) for receiving tissue, tissue isolation, and/or extraction in a laparoscopic procedure.

In one aspect the invention provides an apparatus for use in during laparoscopic surgery comprising an inflatable bag having a tissue-receiving opening at a proximal end thereof and a cuff at the proximal opening, the cuff having a closed configuration for delivery and retrieval of the bag and an open configuration to receive tissue, the cuff being biased into the open configuration.

In one embodiment the bag has a main body which extends from the cuff and the main body of the bag is more flexible than the cuff. The cuff may be of a different material than that of the main body of the bag. The cuff may be of a stiffer material than that of the main body of the bag.

In some embodiments the cuff extends for a distance of between 2 and 20 cm, between 2 and 10 cm, or about 5 cm.

In one embodiment the bag comprises a biasing element (e.g., a ring) that extends at least partially around the opening. The biasing element (e.g., ring) is preferably flexible to facilitate entry through an incision and/or an instrument access port. That is, the biasing element (e.g., ring) may bias the cuff into the open configuration.

In one case the biasing element (e.g., ring) comprises a loop (e.g., an O-ring) extending around the cuff. The loop may be of a shape memory material such as Nitinol. The loop may comprise a single loop element which is open or closed.

In one case the loop comprises a plurality of loop parts.

In some embodiments at least one of the loop parts is movable relative to another of the loop parts. At least one of the loop parts may be movable circumferentially relative to another ring element.

In one case the apparatus comprises a retainer for opening the bag.

The retainer may comprise at least one ring element which extends at least partially around the opening. The ring element may be flexible to facilitate entry through an incision and/or an instrument access port. In one case the ring element comprises an O-ring.

In one embodiment the retainer comprises ring parts. There may be two separate ring parts.

In one embodiment the apparatus (e.g., bag) comprises a tether for each of the ring parts.

In some embodiments, the bag may comprise a tether extending proximally from the cuff. The cuff may comprise a tab for use in grasping the bag.

In one aspect the retainer has an insertion configuration and an expanded deployed configuration. The retainer may be biased into the deployed configuration.

In one case the bag is foldable for insertion.

The invention also provides an apparatus comprising an introducer sheath or pouch for containing the bag in an insertion configuration. The introducer sheath or pouch may be at least partially insertable through an opening and/or an incision and/or an access port.

In one case the apparatus comprises an activator for delivering the bag from the pouch, on insertion. The activator may comprise a tab. In one case the activator comprises a plunger.

In one embodiment the apparatus comprises a user tether attached to the bag.

In one case the bag comprises a neck region. The neck region may be adjacent to the retainer.

In one embodiment the bag itself comprises a port. The port may be an exit port and/or an entrance port. The bag may comprise a plurality of ports.

In some embodiments the port comprises a valve. The valve may comprise a choke valve or a cuff valve. In one case the valve comprises an elastomeric material such as a gel.

In some embodiments the apparatus comprises a proximal tether and a distal tether. The distal tether may be movable relative to the proximal tether.

In one case the proximal tether comprises a loop through which the distal tether is movable.

There may be a lock to restrict movement of the distal tether. In one case the lock is provided by or on the proximal and/or the distal tether. The lock may comprises a projection on the distal tether which is engagable by the proximal tether.

In one embodiment the apparatus further comprises an access port to which the bag is mounted or mountable. The access port may comprise a retractor having a distal anchoring element for location within a wound interior, a proximal member for location externally of a wound opening and a retractor member extending proximally from the distal anchoring element to retract laterally the sides of an incision.

The bag may be mountable to the proximal member of the retractor.

In one embodiment the apparatus further comprises a cap for closing the proximal side of the retractor. The cap may comprise an access device for an instrument or a surgeons hand/arm. The access device may be mountable to the proximal member of the retractor.

The invention also provides apparatus for use in laparoscopic surgery comprising a bag of the invention and a retractor. The apparatus may further comprise an access port.

The invention also provides a viscera retainer comprising an apparatus of the invention.

In another aspect the invention provides a method for performing a laparoscopic procedure comprising the steps of:—
　　inserting a bag according to the invention through an opening;
　　inflating the bag;
　　delivering tissue into the bag before or after inflating the bag; and
　　carrying out a procedure on the tissue located in the inflated bag.

In one embodiment the opening is an opening into a body cavity.

The opening may be provided, at least in part, by an incision.

In one embodiment the method comprises providing a trocar and inserting the bag through the trocar.

The method may comprise providing a retractor in the opening and inserting the bag through the retracted opening.

The tissue may be delivered into the bag before inflating the bag.

The method may comprise the step, either before or after delivery of the tissue into the bag, of mounting the bag to the retractor.

In one embodiment the method comprises passing an instrument into the inflated bag to carry out a procedure.

In one case the method comprises inserting a trocar into the bag.

The method may comprise the steps of providing an access port in the bag and passing an instrument and/or tissue through the access port.

In one embodiment the method comprises sealing the access port prior to and/or subsequent to passage of an instrument and/or tissue through the access port.

The device of the invention comprises at least one instrument seal to effect a seal around at least one instrument extended through the device, the instrument seal being configured to be arranged in sealing relationship to a body of a patient. The device preferably has a distal anchoring member for location within a wound interior. The device preferably also has a retractor member extending proximally from the distal anchoring member to retract laterally the sides of a wound opening. Preferably the device comprises a first instrument seal to effect a seal around a first instrument extended through the device, and a second instrument seal to effect a seal around a second instrument extended through the device. By providing the two seal arrangement, this ensures that insertion or manipulation or removal of the second instrument does not adversely effect the seal around the first instrument. The device may comprise a third instrument seal to effect a seal around a third instrument extended through the device. The first instrument seal may be spaced apart from the second instrument seal. The first instrument seal may be formed separately from the second instrument seal. The first instrument seal may have a larger radial dimension than the second instrument seal. The instrument seal may be a valve. Alternatively, the seal is of a gelatinous elastomeric material.

In one case the device comprises a proximal member for location externally of a wound opening. The retractor member may extend at least between the distal anchoring member and the proximal member. The retractor member may extend in two layers between the distal anchoring member and the proximal member. A first end portion of the retractor member may be fixed to the proximal member. The retractor member may be movable relative to the distal anchoring member. A second end portion of the retractor member may be movable relative to the proximal member. The retractor member may extend distally from the proximal member to the distal anchoring member, may be looped around the distal anchoring member, and may extend proximally from the distal anchoring member to the proximal member. The proximal member may comprise an inner part and an outer part. The retractor member may extend between the inner part and the outer part.

In another embodiment the instrument seal is spaced proximally of the proximal member. The device may comprise at least one connector member to connect the proximal member to the at least one instrument seal. The connector member facilitates a degree of lateral movement of the instrument while maintaining the seal. The connector member may comprise a sleeve. The connector member may be of a laterally flexible material. The connector member may be of a longitudinally rigid material. The connector member may be of a rubber-like material. The connector member may be of a longitudinally flexible material.

In another case the instrument seal is mounted to the connector member. The instrument seal may be releasably mounted to the connector member. The instrument seal may comprise a mounting part to mount the instrument seal to the connector member. The mounting part may be of a rigid material. The instrument seal may comprise a sealing part to effect a seal around an instrument extended through the device, the sealing part being overmoulded over at least part of the mounting part.

In one embodiment, a method for performing a laparoscopic procedure may include inserting a bag through a patient opening, delivering tissue into a bag opening of the bag, withdrawing the bag opening back through the patient opening, sealing the bag, inflating the bag to create an artificial pneumoperitoneum that extends the abdomen, conforms to the peritoneal cavity, and provides additional working and viewing space; and carrying out a procedure on the tissue located in the inflated bag.

In another embodiment, a method for performing a laparoscopic procedure includes inserting a bag through a patient opening and into a peritoneal cavity, delivering tissue into the bag in an insufflated peritoneal cavity, sealing the bag, inflating the bag to apply a retracting force to the materials outside the bag thereby enlarging the peritoneal cavity, carrying out a procedure on the tissue located in the inflated bag; and allowing the peritoneal cavity to uninsufflate so that the inflated bag is located in an uninsufflated peritoneal cavity.

In yet another embodiment, a method for performing a laparoscopic procedure includes inserting a bag through a patient opening and into a peritoneal cavity, delivering tissue into the bag, sealing the bag, inflating the bag to retract surrounding structures and organs and urge the bag against the abdominal wall, piercing the bag by one or more trocars at a location where the bag is urged against the abdominal wall, carrying out a procedure on the tissue located in the inflated bag, and communicating the peritoneal cavity with the atmosphere prior to carrying out a procedure on the tissue located in the inflated bag.

In a further embodiment, a method for performing a laparoscopic procedure includes insufflating the peritoneal cavity to provide a working and viewing space, excising tissue within the working and viewing space, inserting a bag into the working and viewing space, delivering the excised tissue into the bag, sealing the bag, inflating the bag to replace the working and viewing space of the insufflated peritoneal cavity with a working and viewing space within the bag, and carrying out a procedure on the tissue located in the inflated bag.

The methods for performing a laprascopic procedure may further include one or more of the following features: the opening may be a naked incision in the abdominal wall; the opening may be one of an opening through a retractor device coupled to an incision, or an opening through a trocar coupled to an incision; the inserting of a bag through an opening may include inserting the bag through a valve; the extending of the abdomen includes the bag contacting both the anterior abdominal wall and the abdominal visecera; the opening may be an opening through the retractor device, and the sealing of the bag may include sealing the bag to a proximal end of the retractor device with a cap; the delivering of tissue into the bag may be performed in an insufflated peritoneal cavity; the carrying out of a procedure in the inflated bag may be performed in an uninsufflated peritoneal cavity; the inflating of the bag may include inflating the bag to retract surrounding structures and organs and urge the bag against the abdominal wall; piercing the bag with one or more trocars at a location where the bag may be urged against the abdominal wall; the carrying out of a procedure may include sealably inserting a morcellator into the bag and morcellating the tissue; and retrieving the tissue by pulling the bag out through the opening.

In yet another embodiment, an inflatable artificial pneumoperitoneum bag includes a length and a width, an artificial pneumoperitoneum bag neck portion having a first end and a second end, the first end forming a bag opening, an artificial pneumoperitoneum bag body portion forming a closed cavity in fluid communication with the second end of the neck portion, the body portion having a length and width greater than a length and width of the neck portion, and a ring located at the bag opening, the ring configured to bias the bag opening toward an open condition.

In yet another embodiment, an inflatable artificial pneumoperitoneum bag, including a first planar sheet portion and a second planar sheet portion, the first and second planar sheet portions having joined edges to form the pneumpoeritoneum bag having a length and a width, a neck portion having a first end and a second end, the first end forming a bag opening, a body portion forming a closed cavity in fluid communication with the second end of the neck portion, the body portion having a length and width greater than a length and width of the neck portion, and a ring located at the bag opening, the ring configured to bias the bag opening toward an open condition.

The inflatable artificial pneumoperitoneum bag may further include one or more of the following features: a length of the bag is between 300 and 600 mm when the bag is uninflated, and a maximum width of the bag is between 200 and 500 mm when the bag is uninflated; the neck portion has a diameter of between 100 and 220 mm when in the open condition; the neck portion has a length of between 100 and 300 mm when the bag is uninflated; a width-extending cross-section of the body portion includes an oval shape when the bag is inflated; the bag includes sterilized polyester polyurethane planar sheet portions having joined edges; the bag is symmetric about two planes that are normal to one another; the neck portion includes edges that extend parallel to a lengthwise axis of the bag; and the ring is formed of a shape memory material and is received through loops in the neck portion.

In another embodiment, a method includes creating an artificial pneumoperitoneum in a patient using an artificial pneumoperitoneum bag, the artificial pneumoperitoneum bag including a length and a width, a neck portion having a first end and a second end, the first end forming a bag opening, a body portion forming a closed cavity in fluid communication with the second end of the neck portion, the body portion having a length and width greater than a length and width of the neck portion, and a ring located at the bag opening, the ring configured to bias the bag opening toward an open condition.

In another embodiment, a method includes creating an artificial pneumoperitoneum in a patient using an artificial pneumoperitoneum bag, the artificial pneumoperitoneum bag including a first planar sheet portion and a second planar sheet portion, the first and second planar sheet portions having joined edges to form the pneumpoeritoneum bag having a length and a width, a neck portion having a first end and a second end, the first end forming a bag opening, a body portion forming a closed cavity in fluid communication with the second end of the neck portion, the body portion having a length and width greater than a length and width of the neck portion, and a ring located at the bag opening, the ring configured to bias the bag opening toward an open condition, and the creating of the artificial pneumoperitoneum includes positioning the joined edges in alignment with the lateral walls of the abdomen.

The methods for performing a laprascopic procedure may further include one or more of the following features: the length of the bag is between 300 and 600 mm when the bag is uninflated, and a maximum width of the bag is between 200 and 500 mm when the bag is uninflated; the neck portion has a diameter of between 100 and 220 mm when in the open condition; the neck portion has a length of between 100 and 300 mm when the bag is uninflated; a width-extending cross-section of the body portion includes an oval shape when the bag is inflated; the bag is formed of sterilized polyester polyurethane planar sheet portions having joined edges; the bag is symmetric about two planes that are normal to one another; the neck portion includes edges that extend parallel to a lengthwise axis of the bag; the ring is formed of a shape memory material and is received through loops in the neck portion.

BRIEF DESCRIPTION OF THE DRAWINGS

The invention will be more clearly understood from the following description of some embodiments thereof, given by way of example only, with reference to the accompanying drawings, in which: —

FIG. 1 is an isometric view of a pneumoperitoneum device according to the invention;

FIG. 2 is another isometric view of the device of FIG. 1;

FIGS. 3 to 5 are views of another pneumoperitoneum device according to the invention;

FIGS. 6 to 18 are diagrams illustrating the use of the device of FIGS. 1 to 5;

FIGS. 19 to 22 are diagrams illustrating another use of the device of FIGS. 1 to 5;

FIGS. 23 to 24 are diagrams illustrating a further use of the device of FIGS. 1 to 5;

FIGS. 25 to 30 are diagrams illustrating various ways in which a device according to the invention may be introduced;

FIGS. 31 to 35 are diagrams illustrating the device, in use;

FIG. 36 is a diagram of another device according to the invention;

FIGS. 37 to 45 are diagrams illustrating the device of FIG. 36, in use;

FIG. 46 is a diagram of another device according to the invention;

FIGS. 47 to 54 are diagrams illustrating the device of FIG. 46, in use;

FIG. 55 is a diagram of a further device according to the invention;

FIGS. 56 to 63 are diagrams illustrating the device of FIG. 55, in use;

FIGS. 65 to 74 are diagrams illustrating the device of FIG. 64, in use;

FIGS. 82 to 87 are isometric views of alternative grommets;

FIG. 88 is an isometric view of another device according to the invention with a multi-lumen access port removed;

FIG. 89 is an isometric, partially cut-away view of the device of FIG. 88 with an access port in position for use;

FIG. 90 is an isometric view of a device according to the invention.

FIG. 91 is another view of the device of FIG. 90 with an access port in position for use;

FIGS. 92(a) and 92(b) are isometric views of single lumen access ports for use with the devices of the invention;

FIG. 95 is an isometric view illustrating devices of the types of FIGS. 93 and 94, in use;

FIGS. 96 to 98 are views of various seals that may be used in association with the device;

FIGS. 99 to 110 illustrate one method of use of devices according to the invention;

FIGS. 111 to 113 are views illustrating a locking detail of the device of FIGS. 99 to 110;

FIGS. 114 to 117 are views of a device according to the invention, in use in the colon;

FIG. 118 is an isometric view of another device according to the invention;

FIG. 119 is an isometric view of a further device according to the invention;

FIG. 120 is an isometric view of a pneumoperitoneum device according to the invention loaded in an introducer;

FIG. 121 is an isometric view of a bag according to the invention;

FIG. 122 is a cross sectional view on the line A-A in FIG. 121;

FIGS. 131 to 133 are isometric views illustrating the presentation of the bag to the tissue opening, subsequent inflation of the bag, and procedures such as morcellation being carried out on tissue in the inflated bag;

FIGS. 134 to 138 are diagrams illustrating various alternative arrangements of trocar(s) and instrument(s) used in performing procedures on tissue in the inflated bag;

FIGS. 139 to 143 are various views of a biasing loop comprising loop sections which are movable relative to one another;

FIGS. 144 to 149 are various views of another biasing loop;

FIGS. 150 to 153 are various views of a further biasing loop;

FIGS. 154 to 156 are various views of another biasing loop;

FIGS. 166 to 168 are isometric views of further bag devices according to the invention with a retaining ring in place in a cuff of the bags;

FIGS. 169(a)-169(c) and 170 illustrate the mounting of a ring to the cuff of the bag of FIG. 168;

FIGS. 172 to 176 illustrate an introducer for use in deploying and manipulating a bag device;

FIGS. 177 to 180 are views of further introducers with various pressure dissipating features;

FIGS. 181 to 184 illustrate another bag device having a generally ovoid shape;

DETAILED DESCRIPTION

Figure 33:
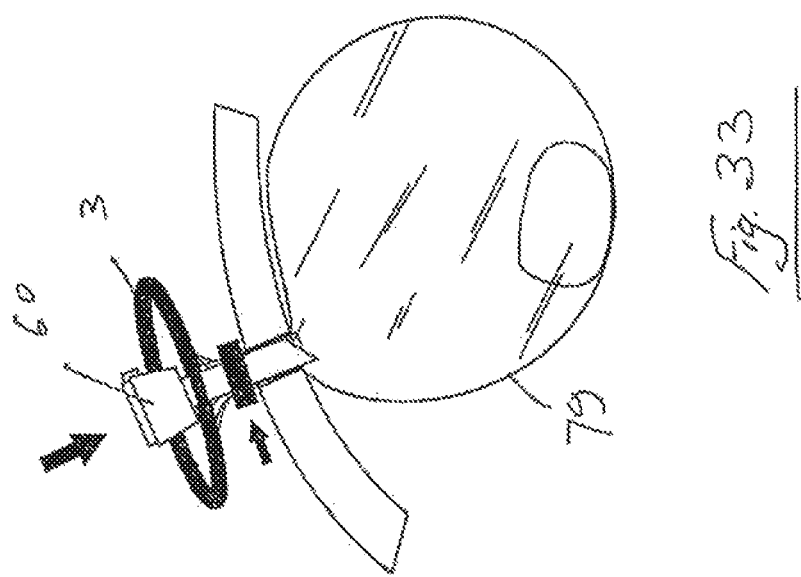

The invention provides an artificial pneumoperitoneum device for tissue isolation and/or extraction in a laparoscopic procedure The device is used to safely reduce and remove resected tissue from within the abdomen via small laparoscopic incisions. The bag creates an artificial pneumoperitoneum containing the specimen and eliminating the dissemination of tissue and cellular fluids within the peritoneal cavity. The device facilitates effective and safe isolation of tissue/organs within an artificial pneumoperitoneum for improved surgical procedures and subsequent safe tissue extraction.

A tissue bag is inserted within the peritoneal cavity through an incision in the abdominal wall or vagina.

In one case the bag with one or more openings is placed within the abdomen. Excised tissue is placed within the opening of a deflated bag. One or more openings of the bag are withdrawn outside the abdomen and the bag is inflated. Instruments including laparoscopic visualization are placed within the inflated bag that remains within the peritoneal cavity.

Visualisation tools may also be provided external of the bag. The tissue retained within the bag is morcellated/crushed/reduced and removed. The bag is deflated and removed with residual tissue/blood/fluids inside. A major advantage is that the tissue to be removed is retained in the bag which prevents potentially harmful material such as cancerous cells from being released in the body cavity.

Referring to the drawings, and initially to FIGS. 1 and 2 thereof, there is illustrated an apparatus for use in laparoscopic surgery comprising a bag 1 having an opening 2 to receive tissue and a ring element 3 extending around the opening 2. The bag is inflatable.

Referring to FIGS. 3 to 5, there is illustrated another bag device according to the invention which is similar to the bag device of FIGS. 1 and 2 and like parts are assigned the same reference numerals. In this case the bag 1 has a necked region 5 to reduce the amount of material near the ring 3. This facilitates attachment of the bag 1 to an external element.

The bag device 1 is suitable for use during laparoscopic surgery to facilitate procedures on tissue in an insufflated cavity while maintaining pneumoperitoneum.

The bag device 1 may be mounted to a retractor. One such retractor comprises a distal anchoring ring 10, a retractor member such as a sleeve 11, and a proximal ring assembly 12.

One such retractor is described in US 2005-0090717 A, the entire contents of which are incorporated herein by reference. The distal anchoring ring 10 is located within a wound interior, in use. In this case the distal anchoring ring 10 is provided in the form of an O-ring. The proximal ring assembly 12 is located externally of a wound opening, in use. The retractor member 11 may be employed to retract laterally the sides of a wound opening. In this case, the retractor member is provided in the form of a sleeve.

The proximal end of the retractor 11 is closable by a cap which in this case comprises an instrument access device 30 which may have a number of instrument ports 31 to effect a seal around an instrument extended through the device 30. The instrument access device 30 may be releaseably mountable to the proximal ring assembly 12. At least some of the instrument ports may include a stalk 32 which is laterally flexible and longitudinally rigid.

FIG. 6 illustrates an instrument 51 being introduced under vision provided by a camera 52 through an instrument access port 31.

FIG. 7 shows an organ or tissue such as an uterus 35 which has, been severed from it's retaining structures.

FIG. 8 illustrates the bag device 1 being inserted into the abdominal cavity at the beginning of a procedure or as and when required. The bag 1 is inserted in a small flattened state for ease of insertion through a small opening such as an incision. As shown in FIG. 8, the bag device 1 is inserted through an opening that is open to the atmosphere, and thus the peritoneal cavity is uninsufflated in this embodiment. The bag may also be introduced through a valve without the need to remove the access cap 30. One such arrangement is illustrated in FIG. 10, and this allows the bag device to be inserted into an insufflated peritoneal cavity.

Figure 11A:
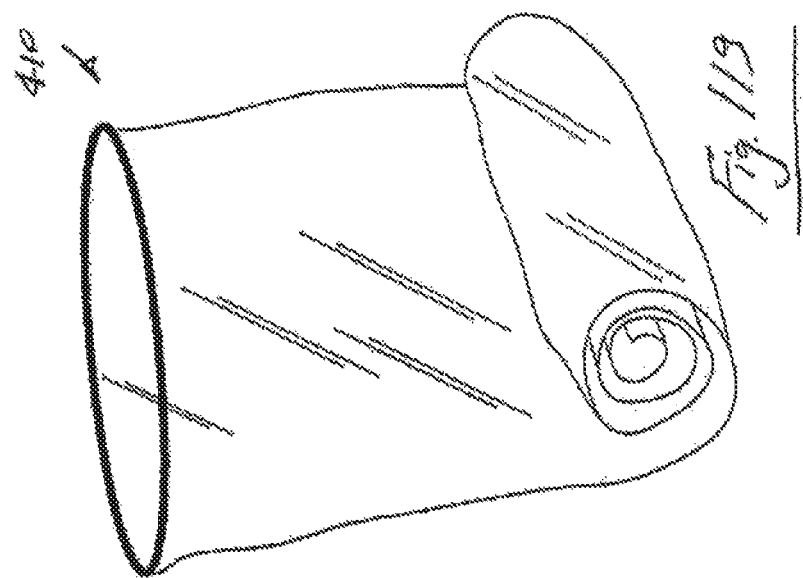
Figure 11B:
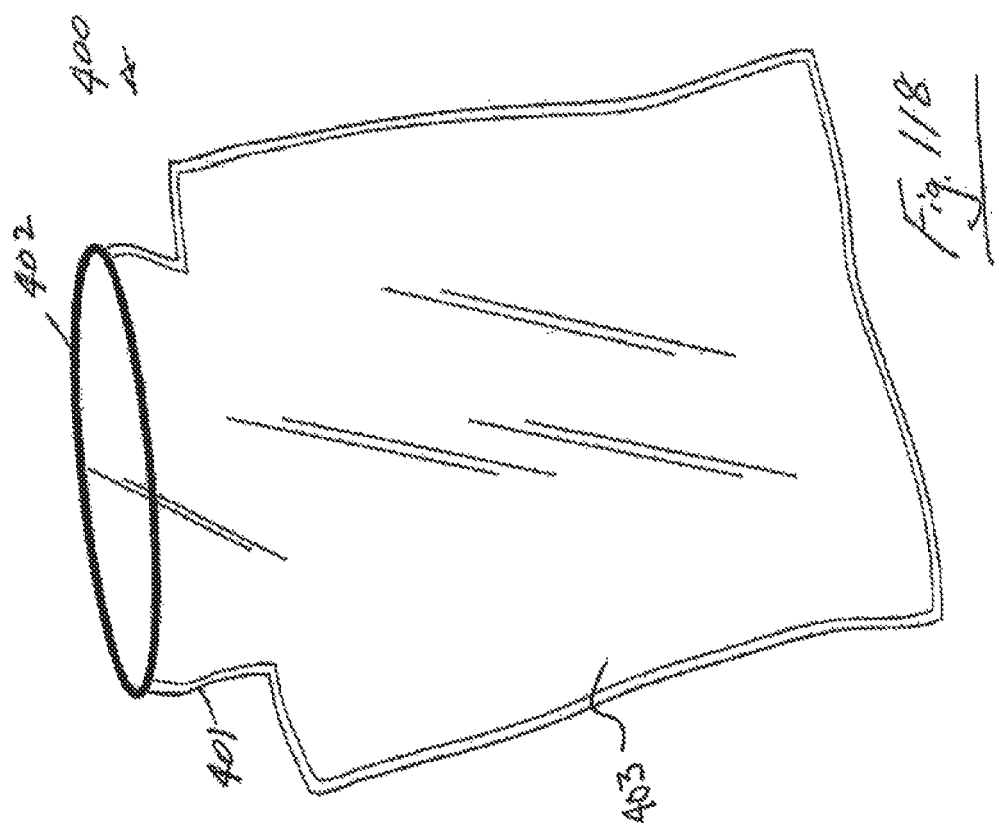
Figure 123:
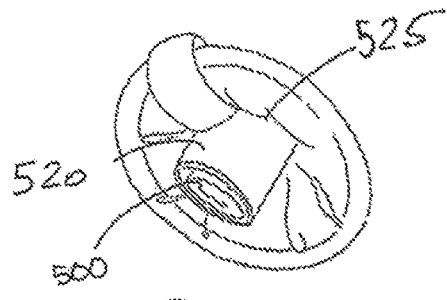
FIGS. 123 to 126 are isometric views illustrating the insertion of the bag through an opening.
Figure 124:
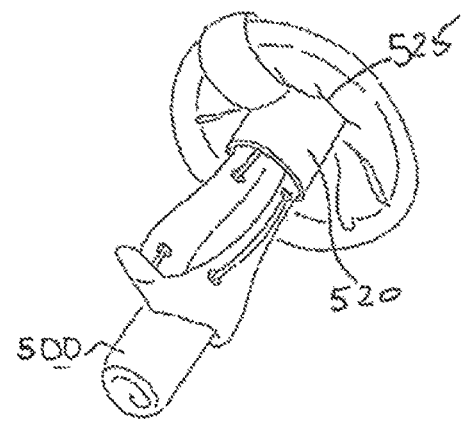
Figure 125:
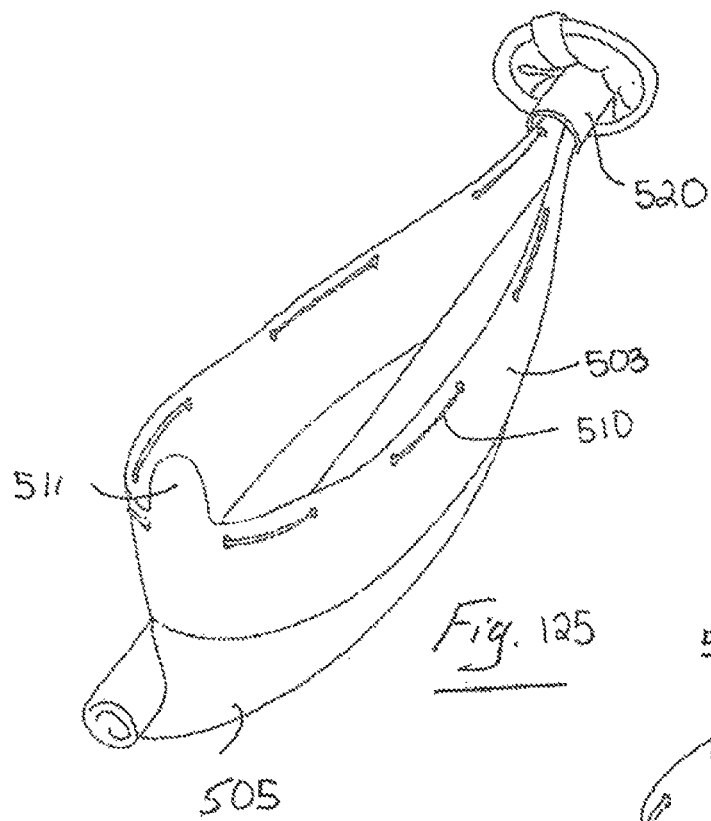
Figure 126:
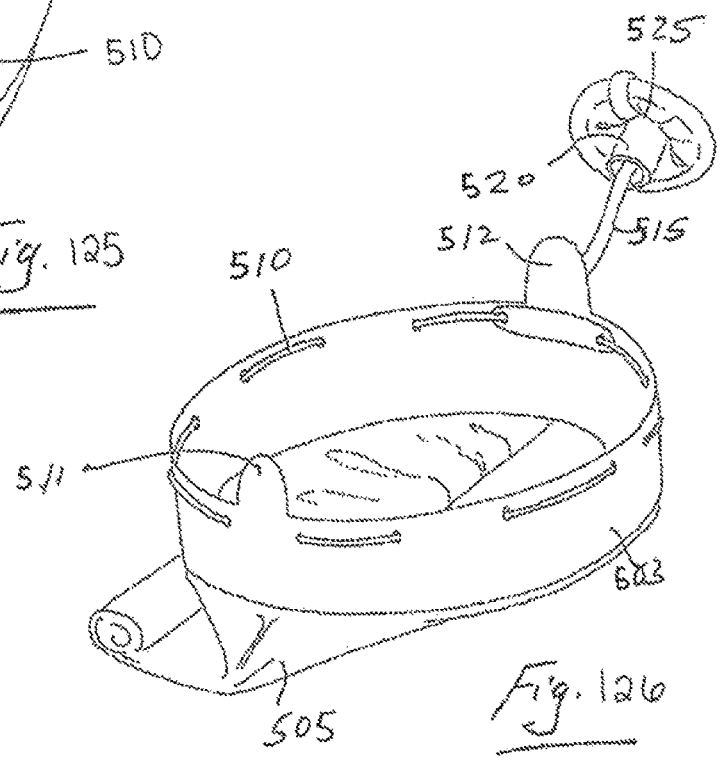

When the bag 1 is inserted in the insufflated or uninsufflated peritoneal cavity, it is opened up (FIG. 9). An organ is then readily manipulated for insertion into the bag 1 as illustrated in FIG. 11. The rigidity of the O-ring 3 keeps the bag open to facilitate insertion of an organ.

Figure 76:
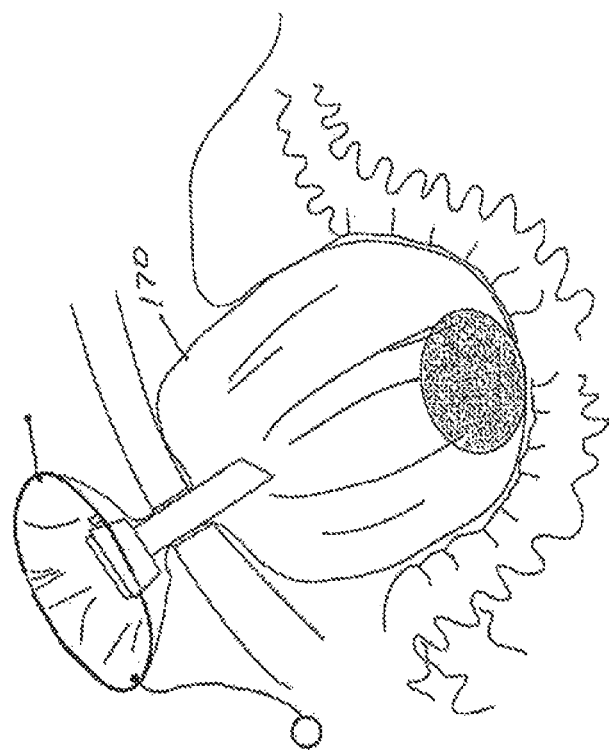
FIGS. 76 to 78 are diagrams illustrating the device of FIG. 75, in use.
Figure 13B:
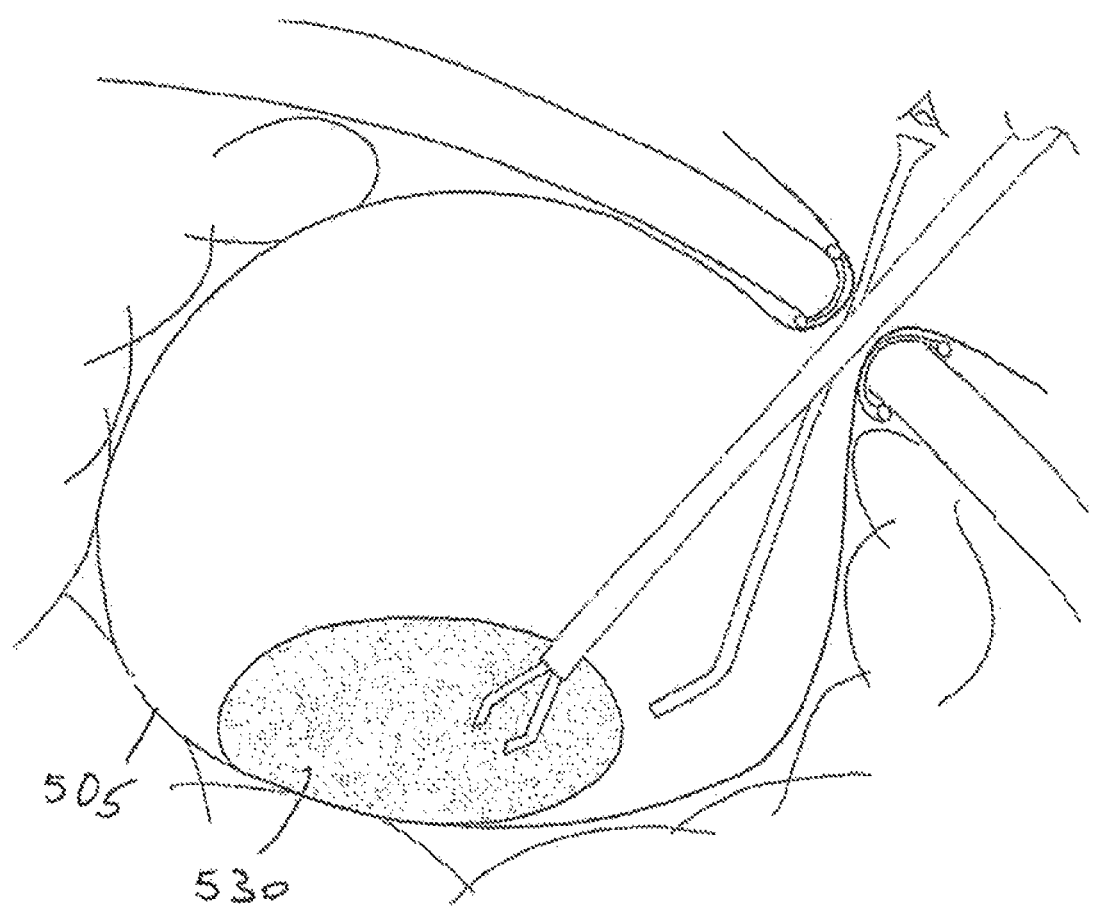
Figure 157:
FIGS. 157 to 160 are diagrams illustrating another bag device of the invention.
Figure 158:
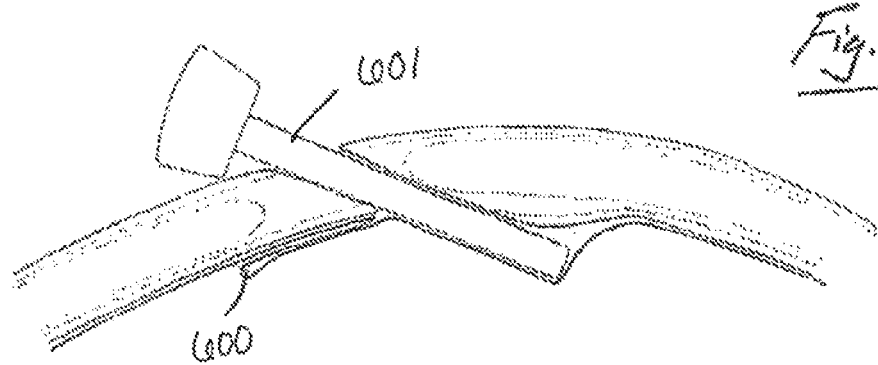
Figure 159:
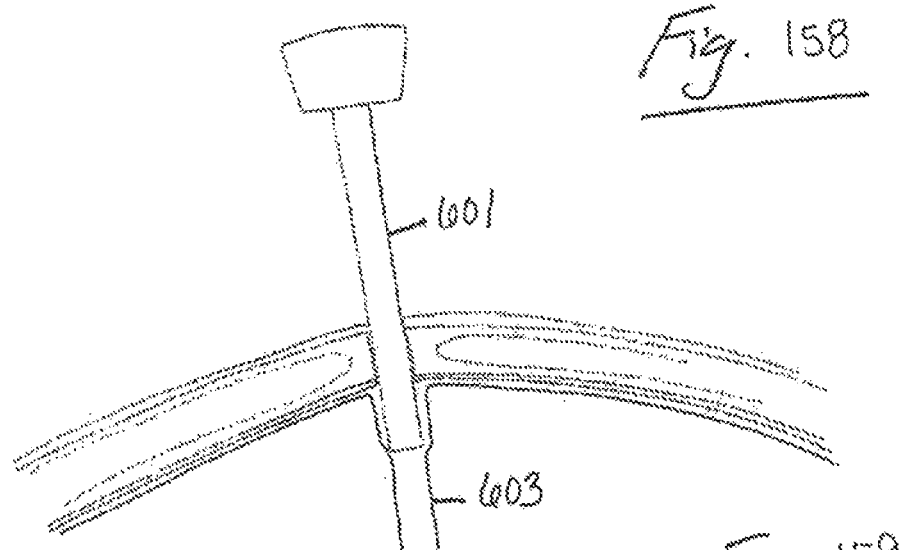
Figure 160:
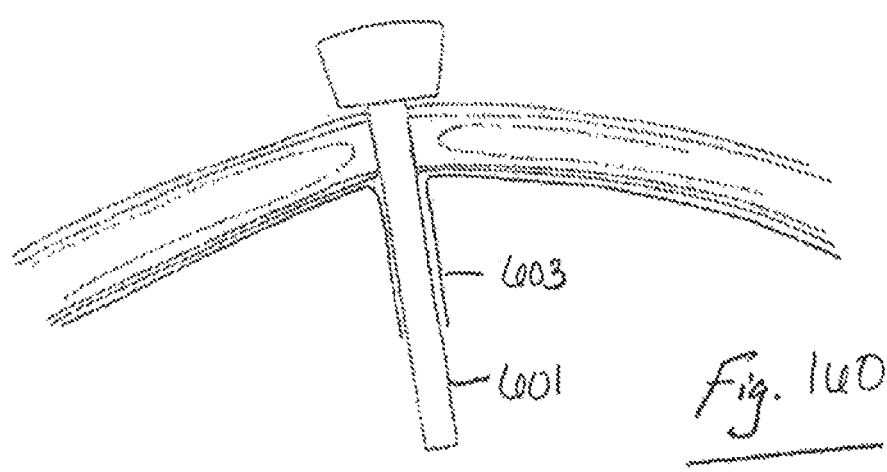

FIG. 12 shows the organ located in the bag 1 and the O-ring 3 being grasped to facilitate manipulation of the bag towards the opening. As shown in FIG. 12, removal of access cap 30 provides an uninsufflated peritoneal cavity prior to inflating the bag device 1. The uninsufflated nature of the peritoneal cavity helps the bag device 1 expand as shown in FIG. 16, and apply a retracting force to the materials outside the bag thereby creating additional space (FIG. 76). It is understood that the bag device 1 could be inflated while the peritoneal cavity is insufflated if there is one or more openings to the peritoneal cavity that allow the insufflation gas to escape to the cavity. One such opening could be provided through an open trocar device or trocar incision opening that was used to carry out the tissue excising explained above. The O-ring 3 is pulled out through the opening (FIG. 13) and the bag 1 is mounted to the proximal ring assembly 12 and the cap 30 is mounted to the proximal assembly 12 (FIG. 14). FIG. 15 illustrates the device in place with an organ enclosed within the bag 1.

The bag 1 is then inflated through an insufflation port 40. The inflation of the bag has the additional benefit of applying a retracting force to the materials outside the bag 1 thereby creating additional space (FIG. 16). Thus, the artificial pneumoperitoneum created in the uninsufflated peritoneal cavity, and within the inflated bag device 1, serves to extend the abdomen and provide additional working and viewing space within the bag device 1.

FIG. 17 shows an organ being worked on in the inflated bag 1. In this case the organ is morcellated. The material is all retained safely within the bag and is not released into the cavity which could cause major difficulties.

When the organ has been morcellated, the bag is readily removed through the original opening. All waste, blood, tissue and the like are safely removed and sealed within the bag 1.

FIG. 19 shows the bag device being inserted through a standard naked incision. Once the specimen has been inserted into the bag 1 (FIG. 20) the ring 3 is pulled back out through the incision (FIG. 21) and a trocar 60 is inserted to create a gas seal (FIG. 22). It may also be possible to insert the bag device 1 directly through a trocar.

In all cases there may be one or more access trocars used in addition to the primary port. Thus, the invention includes procedures which involve two or more incision laparoscopy.

For example, FIGS. 23 and 24 show one arrangement in which an additional trocar 70 is inserted. In some cases, the additional trocar 70 may be extended through the bag whilst maintaining a seal.

A bag 1 is illustrated which has some depth which is preferred. However, a flat material can be used to form a holder in situ and the edges of the material pulled out through an incision and sealed outside, for example by an access device 30.

The invention provides a method of inserting a large bag into the abdominal cavity to allow the insertion of a specimen into the bag. The bag is then sealed and inflated and procedure carried out within the bag.

FIGS. 25 to 30 show various ways a bag 79 may be introduced into the abdomen.

In FIG. 25 the device may be inserted directly through an incision 80.

Referring to FIG. 26, the device may be inserted through a trocar 81.

In FIG. 27 a device may be inserted through a base retractor 82.

Referring to FIG. 28 a device may be inserted through a low profile port 83.

As shown in FIG. 29 the device may be inserted through a Multi-port device 84. The multiport device may, for example, be of the type described in U.S. Pat. No. 8,187,178 or US 20110071389A, the entire contents of which are incorporated herein by reference.

Referring to FIG. 30 the device may be inserted through the base 85 of a multi-port device.

Figure 31:
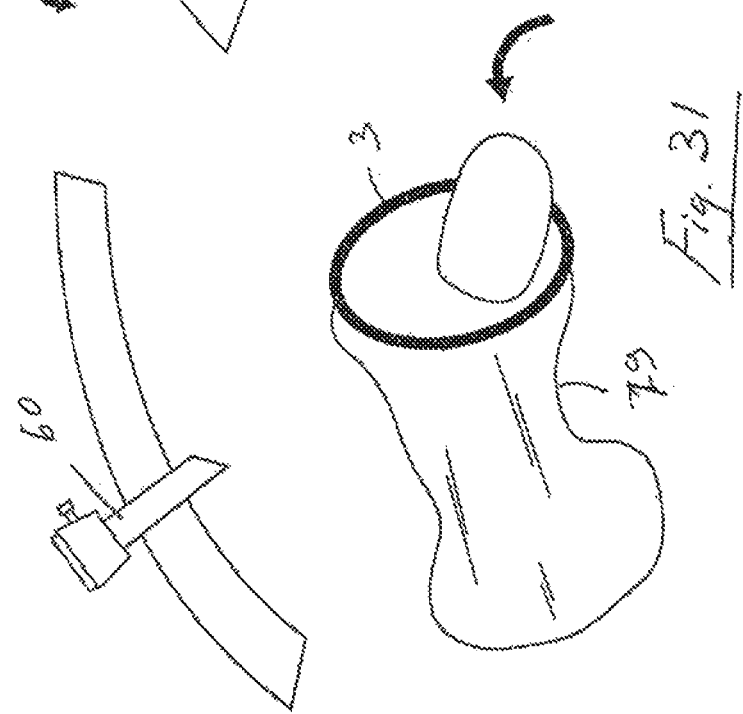

As illustrated in FIG. 31, once the bag 79 has been inserted the specimen is placed inside.

Figure 32:
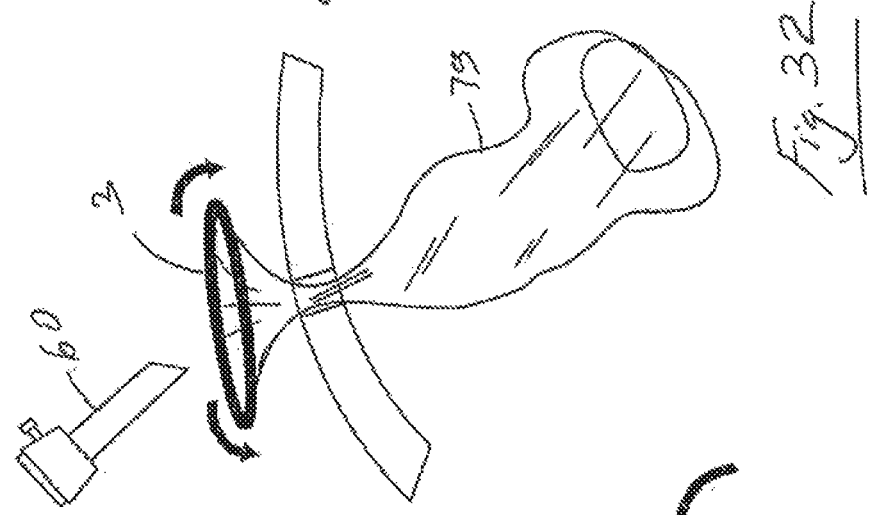

FIG. 32 the lip of the bag 79 is pulled out through the opening.

FIG. 33 the bag 79 is sealed by re-inserting the trocar 60, replacing the cap or inserting a morcallator 78. If necessary an extra seal may be applied to the neck of the bag 79.

As shown in, FIG. 34, once the bag 79 is inflated additional trocars may be inserted into the abdomen as normal and pierced through the bag 79. FIG. 34 also shows a morcallator 78 inserted through a trocar 60.

FIG. 35 shows the morcallator 78 being inserted without the need for a trocar. A sealing ring 77 may be applied around the shaft of the morcallator 78 if necessary to hold back gas.

Referring to FIGS. 36 to 45 a method of inserting a large bag 100 into an abdominal cavity which may automatically open to allow the insertion of a specimen is illustrated. The bag 100 is foldable and has a top opening 105 which may be biased into the open configuration by retaining elements which in this case comprise semi-circular ring parts 101, 102 which have attached tether elements 104, 103 respectively. A pouch 110 is used to house the bag 100 in a folded/retracted configuration. The pouch 110 has a grasping tab 111 and a pull string 115.

FIG. 36 illustrates the main components of the automatically opening bag device.

FIG. 37 illustrates a folded bag 100 inside the pouch 110. In FIG. 38 the pouch 110 is inserted into the abdominal cavity with the aid of the grasping tab 111. When the pouch is inside, the distal pull tether 104 is pulled forward and the bag 100 is released. A rear pull string 115 is pulled in the opposite direction to aid release.

Figure 40:
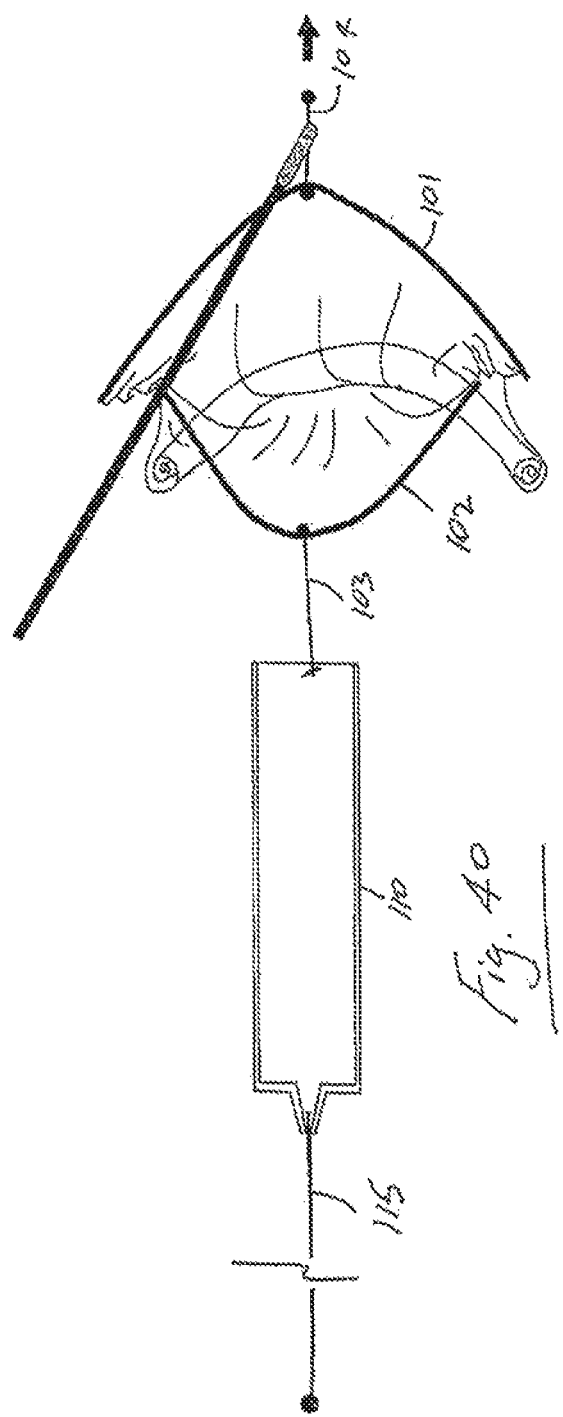

Referring to FIG. 40, it will be noted that as the distal end of the bag 100 is pulled forward the rear of the bag 100 is pulled in the opposite direction as it is attached to the pouch 110 with the connecting tether 103. This action opens the mouth of the bag 100 sufficient to ease the inserting of specimens.

Figure 41:
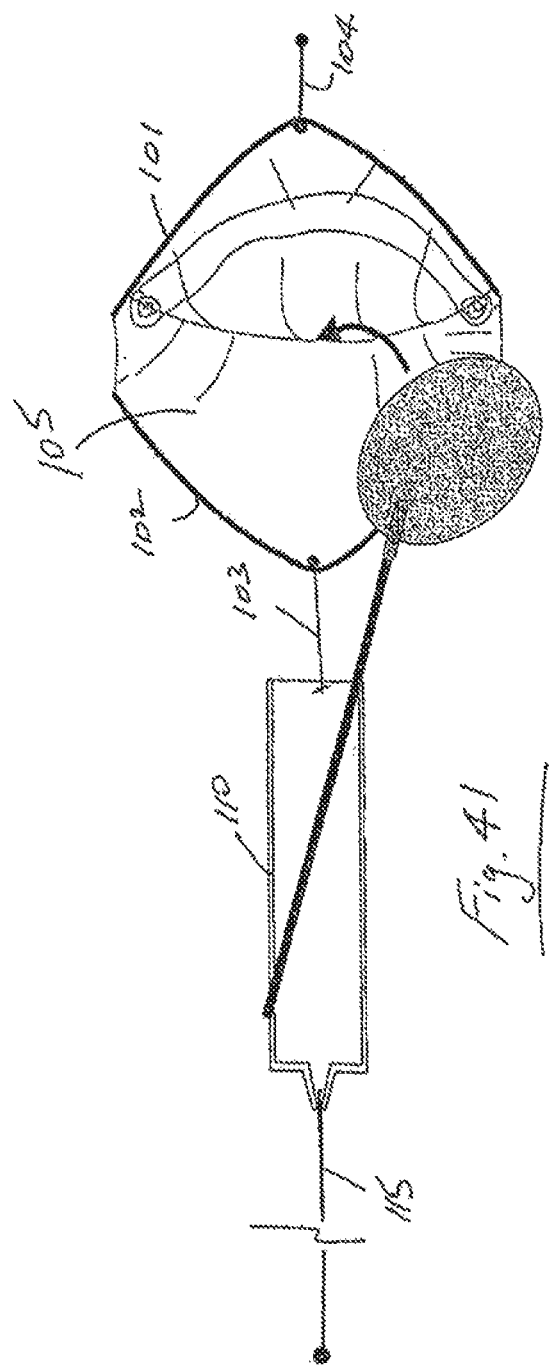

FIG. 41 shows specimens being placed on top of the bag opening 105.

Referring to FIG. 42, by pulling the distal pull tether 104 back and over the specimen, the bag 100 begins to unroll and the specimen travels deeper insider the bag 100. Referring to FIG. 43, as the front and back retaining elements 101, 102 of the bag opening are pulled outwards, the specimen travels further into the bag 100.

FIG. 44 shows the rim of the bag being opened up and the incision being cleared of excess bag material.

Referring to FIG. 45, the opening is re-sealed by attaching a cap, by inserting a trocar, or by inserting a morcallator through the opening.

Referring to FIGS. 46 to 54 there is illustrated another device according to the invention. The device is similar to that of FIGS. 36 to 45 and like parts are assigned the same reference numerals. In this case a bag 120 is housed within a cartridge 121 for delivery and automatically opens when it exits the cartridge 121 on insertion into the abdominal cavity. In this case the ring part 102 remains attached to the cartridge 121. A tether 125 extends between the distal end of the cartridge 121 and the ring element 102. The ring element 101 has a tether element 126 which is grasped by an instrument 127 to pull the bag 120 from the cartridge 121.

FIGS. 46 to 54 show the bag 120 housed in the cartridge 121 which can be inserted into a valve on an access port/trocar 130. The cartridge 121 remains in place during the procedure.

Referring to FIG. 46, the loaded cartridge 121 is placed through a valve on the port 130. FIG. 47 shows the distal pull tether 126 that is positioned so that it is easily grasped with an instrument 127. In FIG. 48 an instrument 127 is inserted and the pull tether 126 is grasped.

Referring to FIG. 49, as the instrument/grasper 127 is pushed forward the bag 120 is released from the cartridge 121. As shown in FIG. 50, once the bag is in far enough, the tether 125 which connects the back side of the bag 120 to the cartridge 121 begins to open the bag 120 up.

Referring to FIG. 51, when the mouth of the bag 120 is sufficiently open a specimen may be placed inside. When the distal pull tether 126 is pulled back as illustrated in FIG. 52 this forces the bag 120 to unroll and the specimen to travel deeper into the bag 120.

Referring to FIG. 53, the cap/trocar 130 is then removed and the rim of the bag 120 is pulled out through the incision and mounted to the retractor 135. FIG. 54 shows the cap, trocar, or morcallator reconnected. The bag 120 is then inflated.

Referring to FIGS. 55 to 63, there is illustrated a removable cartridge 140 with a manually opened bag 141 for insertion through a single port 142. These drawings illustrate a method of inserting a large bag 141 which will be manually opened by the user when inserted into the abdominal cavity. FIGS. 55 to 63 show a bag 141 housed in a cartridge 140 which plugs into a valve 142 on an access port/trocar 130. The bag 141 is ejected from cartridge 140 using a plunger 145 and the cartridge 140 is removed. As shown, for example, in FIG. 54, inflating the bag device 1 creates the artificial pneumoperitoneum and urges the bag against the abdominal wall. This arrangement allows one or more additional trocars 70 to extend through the abdominal wall and directly and sealingly pierce the inflated bag device 1 where the bag device is urged against the abdominal wall. See, for example, FIGS. 24, 34, and 35. Further facilitating this sealing of the additional trocars 70 to the inflated bag device 1 is the fact that the inflated bag device 1 is applying a retracting force to the materials outside the bag device and is thus secured in place against the abdominal wall.

Referring to FIG. 55, the bag 141 is loaded into a cartridge 140 which is then inserted through a valve 142 on the port/trocar 130. When the cartridge 140 is in place of the plunger 145 is inserted through the proximal end of the cartridge 140 as illustrated in FIG. 56. Pushing the plunger 145 down as illustrated in FIG. 57 forces the bag 141 to eject into the abdominal cavity.

Referring to FIG. 58, when the bag 141 has been ejected, the cartridge 140 may be removed, leaving an activation tether 147 in place. An instrument 148 is inserted as illustrated in FIG. 59 and the instrument 148 is used to grasp the distal pull tether 149 which is attached to the front band or ring part/element 101 on the bag 141.

Referring to FIG. 60, the specimen is then lifted into the open mouth of the bag 141. The surgeon can control the mouth of the bag 141 using the activation tether 147. When both the front and the back ring elements 101, 102 of the bag 141 are grasped as illustrated in FIG. 61, the bag 141 can be pulled towards the incision, forcing the specimen to travel deeper into the bag 141.

FIG. 62 shows the valve/trocar 130 being removed and the rim of the bag being pulled out through the incision. In FIG. 63, the rim of the bag 141 is opened up, and the valve/trocar 130 are replaced to seal the bag 141. The bag 141 is then inflated and the procedure carried out within.

Referring to FIGS. 64 to 74 there is illustrated a removable cartridge 150 with a manually opened bag 151 (laparoscopic). These drawings show a method of inserting a large bag 151 which can be manually opened by the user when inserted into the abdominal cavity.

Figure 64:
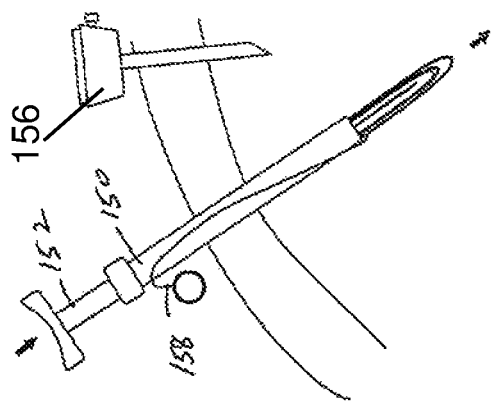
FIG. 64 is a diagram of another device according to the invention.
Figure 65:
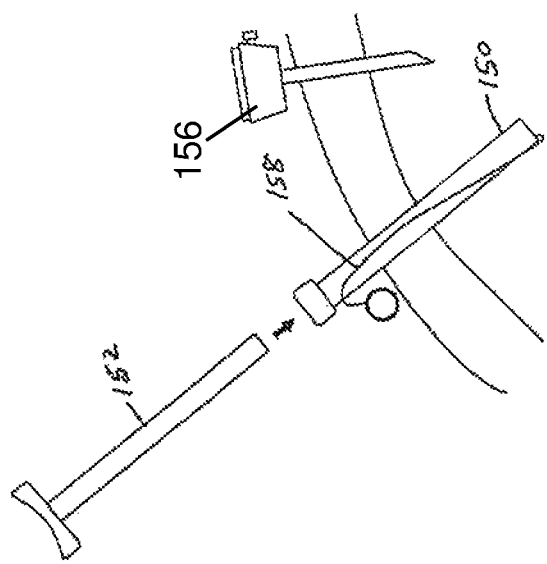
Figure 66:
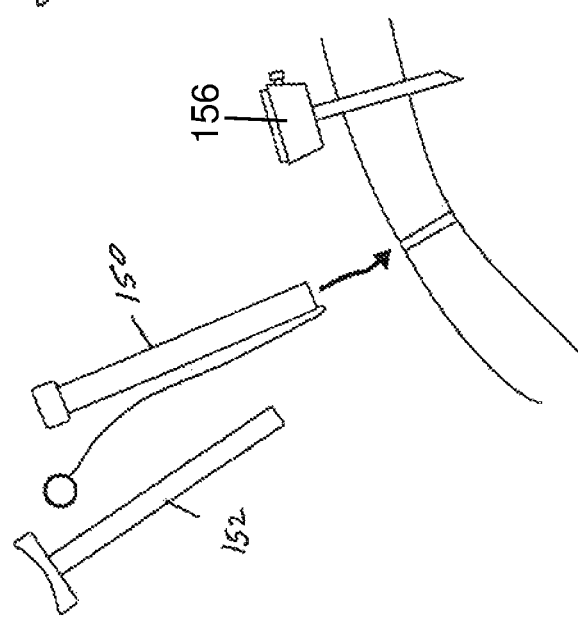
Figure 65:
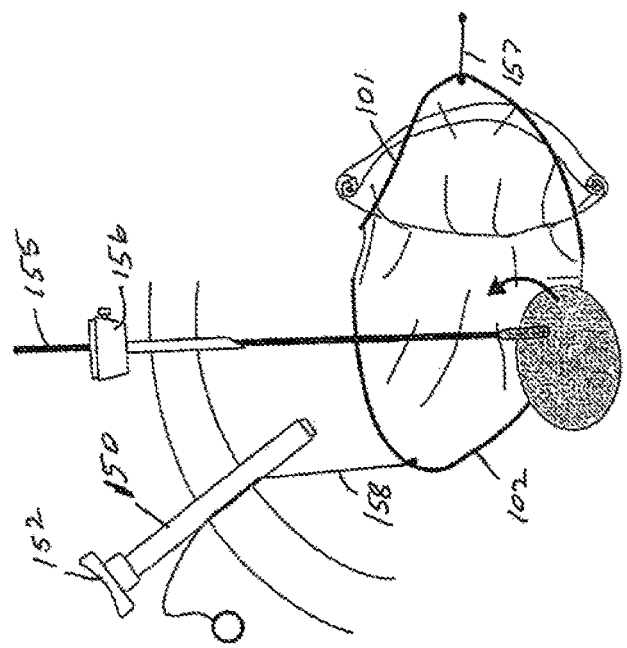
Figure 66:
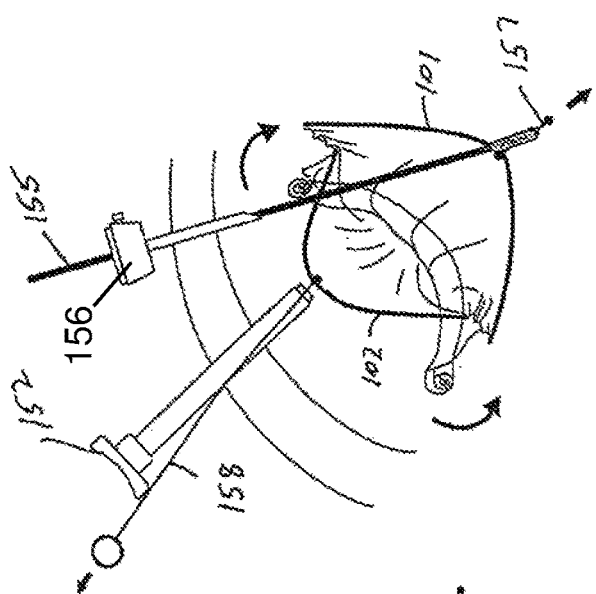
Figure 67:
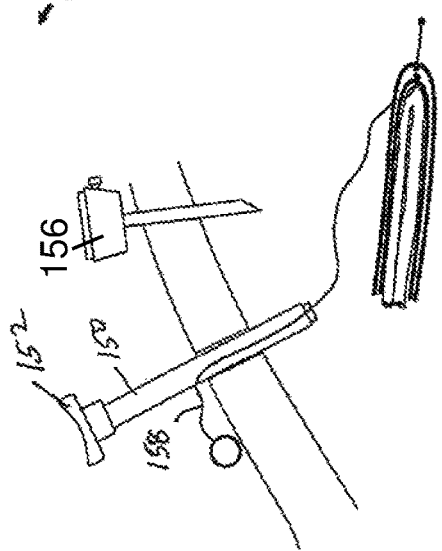

Referring to FIG. 64, the loaded cartridge 150 is inserted through a pre-made incision. When the cartridge 150 is in place a plunger 152 is inserted as illustrated in FIG. 65. The plunger 152 is pushed all the way down and the bag 151 is ejected as shown in FIGS. 66 and 67.

Referring to FIG. 68 an instrument 155 is inserted through a trocar/access port 156 and is used to grasp a distal pull tether 157 which is attached to the front band on the bag. Once the distal tether 157 is held, pulling on the activation tether 158 opens the mouth of the bag 151 and forces the excess material to unroll. The specimen may now be lifted into the open mouth of the bag as shown in FIG. 69. The surgeon can control the mouth of the bag 151 to some degree with an activation tether 158.

Referring to FIG. 70, with the back end of the bag 151 grasped, the bag 151 can be pulled towards the incision, forcing the specimen to travel deeper into the bag 151. The valve/trocar is removed and the rim of the bag is pulled out through the incision as illustrated in FIG. 71. The rim of the bag 151 is opened up, and the morcallator is inserted to seal the bag as shown in FIG. 72. The bag is then inflated and the procedure carried out within.

As illustrated in FIGS. 73 and 74, when the bag 151 is inflated trocars 159 can be pierced through to allow access for additional instruments 160.

Figure 75:
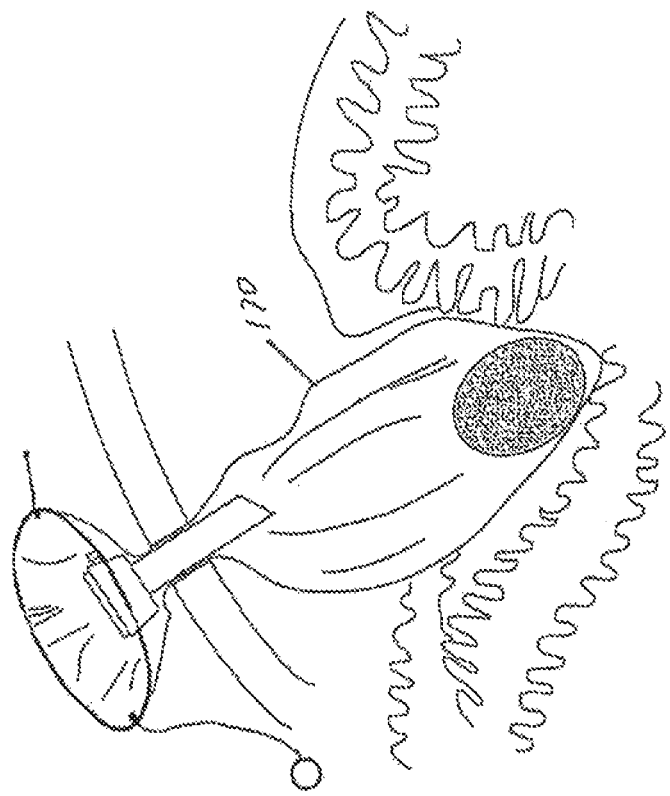
FIG. 75 is a diagram of a device according to the invention for use as a visceral retainer.

Referring to FIGS. 75 to 87 there is illustrated the use of a bag 170 as described above as a visceral retainer. The bag 170 is first inserted and positioned where required (FIG. 75). As the bag 170 is inflated, surrounding structures and organs (abdominal viscera) are retracted as shown in FIG. 76.

Figure 77:
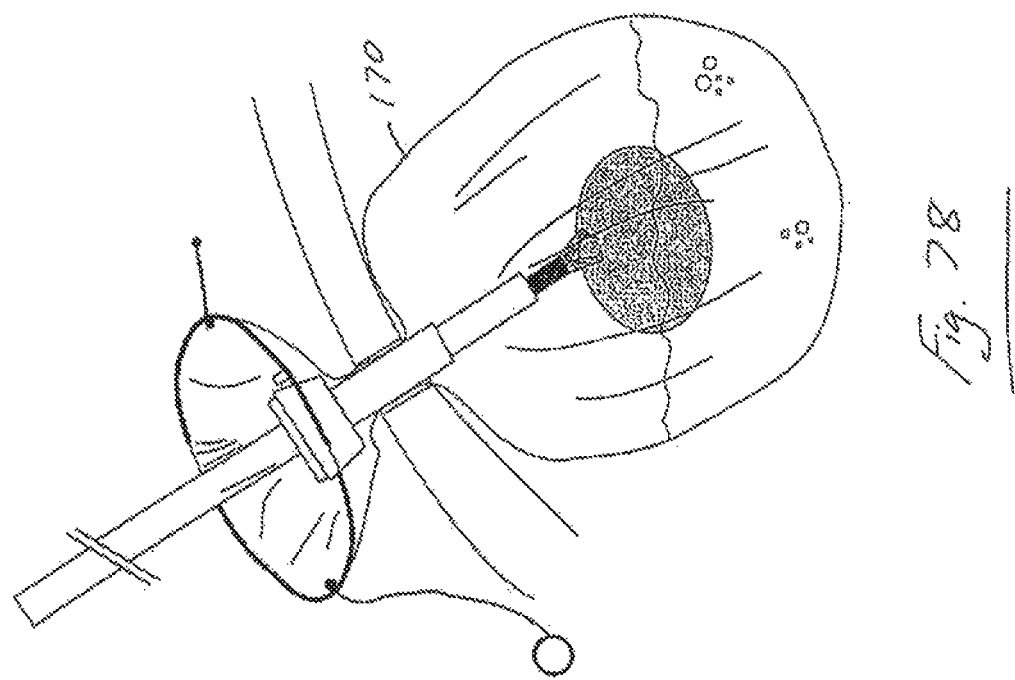
Figure 78:
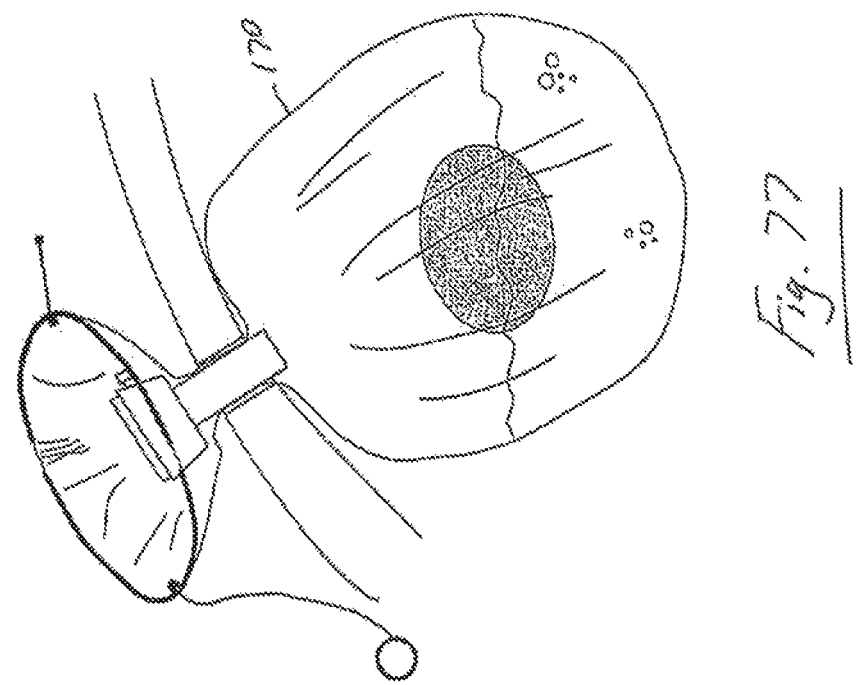

As shown in FIGS. 77 and 78, it may be of benefit to fill, or partially fill the bag 170 with a liquid. These benefits may include: 1) The specimen floats to the top of the bag and therefore the risk of bag damage at the base may be reduced. 2) Liquid may reduce smoke build up in the bag. 3) Blood will be diluted and may therefore allow for enhanced visibility.

Figure 80:
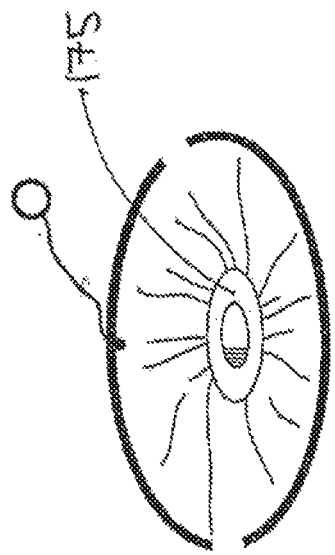
FIGS. 80 and 81 are diagrams illustrating the device of FIGS. 75 to 78 in use.
Figure 79:
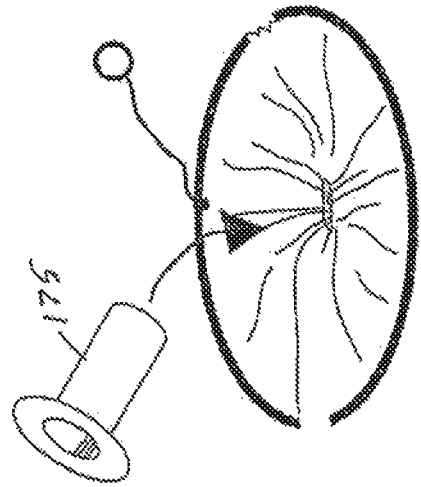
FIG. 79 is a diagram of the device of FIGS. 75 to 78 with an associated grommet.
Figure 81:
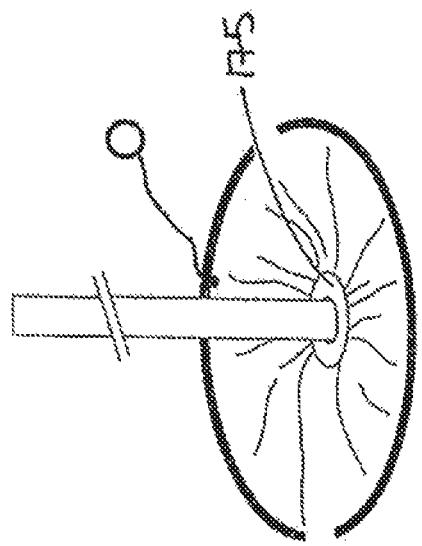

Referring to FIG. 79, when the bag 170 is in place and the neck has been pulled through the incision there is often a lot of excess material in the incision. A grommet 175 may be inserted through the bag/incision to keep excess material away from the incision as illustrated in FIG. 80. This will help prevent damage to the bag 170 and aid visibility and gas flow. With the grommet 175 in place instruments can be inserted with ease as shown in FIG. 81.

Figure 82:
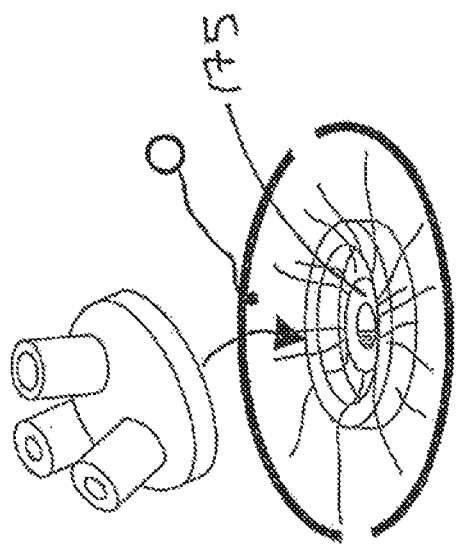

The grommet 175 may be used with multiport or single port access devices (FIG. 82).

In some cases the grommet 175 have an insufflation/desufflation line 176 built in (FIG. 83).

As illustrated in FIG. 84 the grommet may include a series of slits 177 which allow it to conform to various incision dimensions.

The grommet may include a valve system 178 as illustrated in FIG. 85.

An instrument locking mechanism 179 may also be included (FIG. 86).

In some cases, as illustrated in FIG. 87, the grommet may have a series of lumens 180 to aid with ventilation/insufflation.

Referring to FIGS. 88 and 89 there is illustrated a bag device 200 according to the invention.

In this case, the bag 200 is shown in the inflated configuration within a body cavity such as the abdomen. A tissue sample 201 is contained within the bag. An incision is made in the abdomen 202 and the incision is retracted using a retractor 203 as described above. In this case the retractor 203 has an outer proximal ring 204 and a multilumen access port 205 is releasable mounted to the ring 204. The bag 200 extends through the retracted incision and terminates in a retainer ring 206.

FIGS. 90 and 91 illustrate a bag device similar to that shown in FIGS. 88 and 89 but in this case a single instrument lumen access port 211 is mountable to a proximal part of the refractor assembly. The access port 211 may have a cannula section that extends through the refractor or may be an access port 212 with a short proximal leg.

The bag device may itself have an access port to facilitate passage of instruments into and out of the bag and/or to facilitate passage of a tissue sample into the bag.

Figure 94:
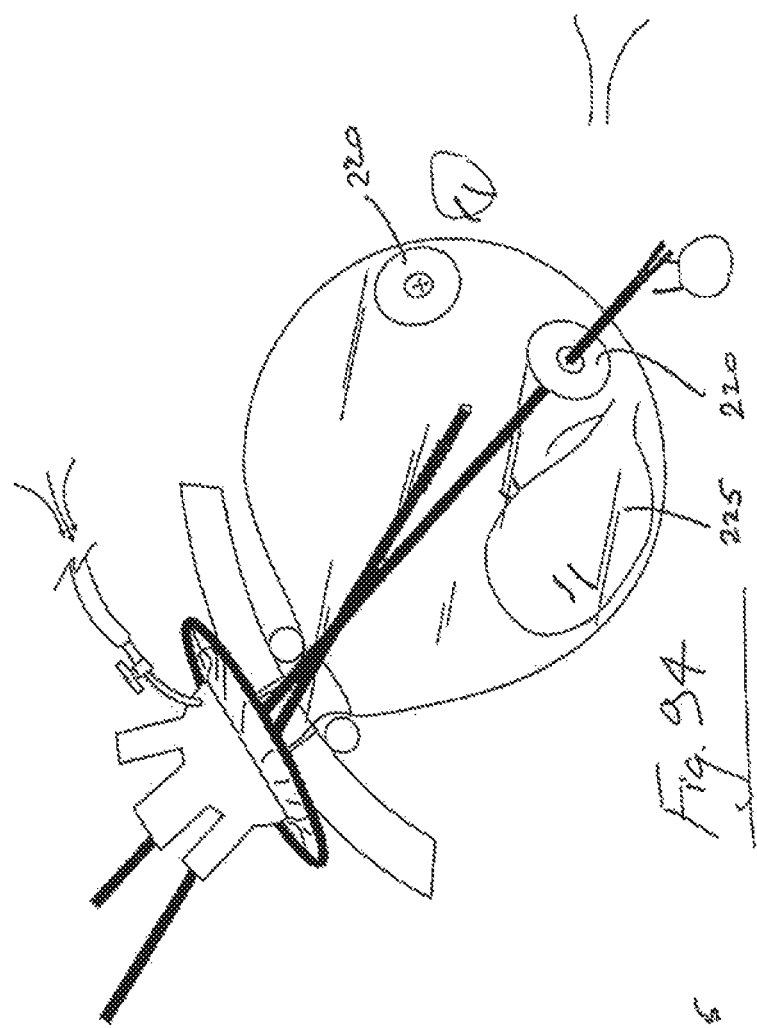
FIG. 94 is an isometric view of another device similar to FIG. 93 with a number of exit ports.
Figure 93:
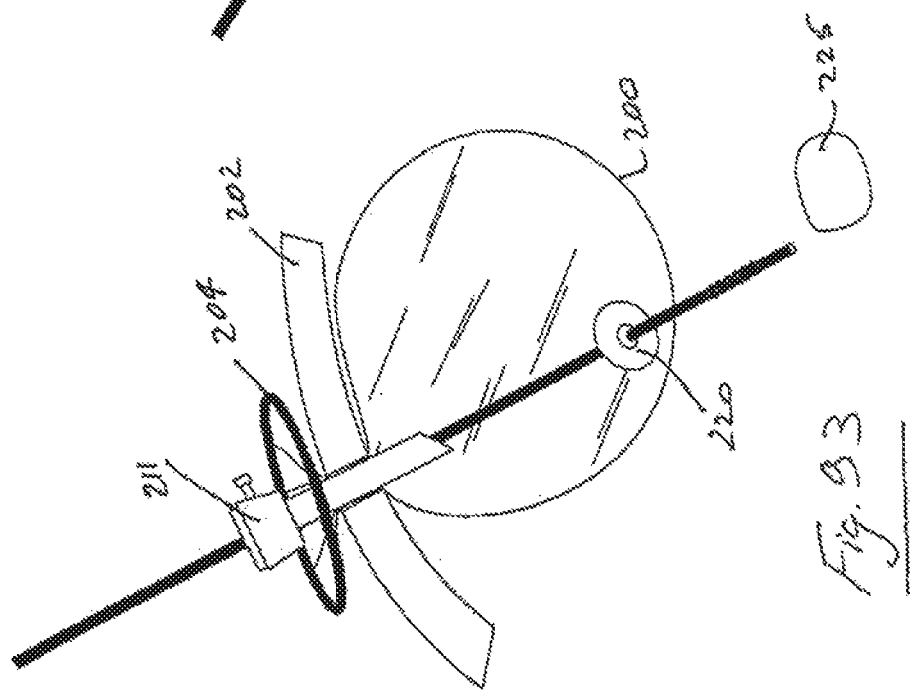
FIG. 93 is an isometric view of a pneumoperitoneum device according to another embodiment of the invention with an exit port from the device.

Referring to FIG. 93 the bag has a single access port 220. However, there may be a plurality of such access ports as illustrated in FIG. 94. Passage of a tissue sample 225 through an access port 220 is illustrated in FIG. 95. The access port 220 may be provided with any suitable valve such as a choke valve, for example, for example a drawstring 226 as illustrated in FIG. 96, a cuff valve 227 as illustrated in FIG. 97, or an elastomeric valve 228 as illustrated in FIG. 98. The valve 228 may be of any suitable plastics, rubber or gel material.

Referring to FIGS. 99 to 110 there is illustrated various steps in methods involving the use of the bag devices of the invention. In the example illustrated the device is of the type described above. The methods involve the use of a bag device 250, a retractor 251, an external access port system 252 and is used to access tissue 253 such as a specimen or an organ through an opening 254 in the body, in this particular case in the abdomen 255. The bag device has a delivery configuration in which it is housed in a retracted condition in a cartridge 260. A plunger 261 is used to deliver the retracted bag device out of the cartridge 260. The bag device 250 has an opening which is biased into an open configuration by a retainer ring 265. The ring 265 may be of a shape memory material as described above. A proximal tether which in this case is in the form of a ring or loop 267 is provided on one side of the ring 265 and a distal tether 268 extends from the side of the ring 265 generally opposite to the proximal tether 267.

Figure 104:
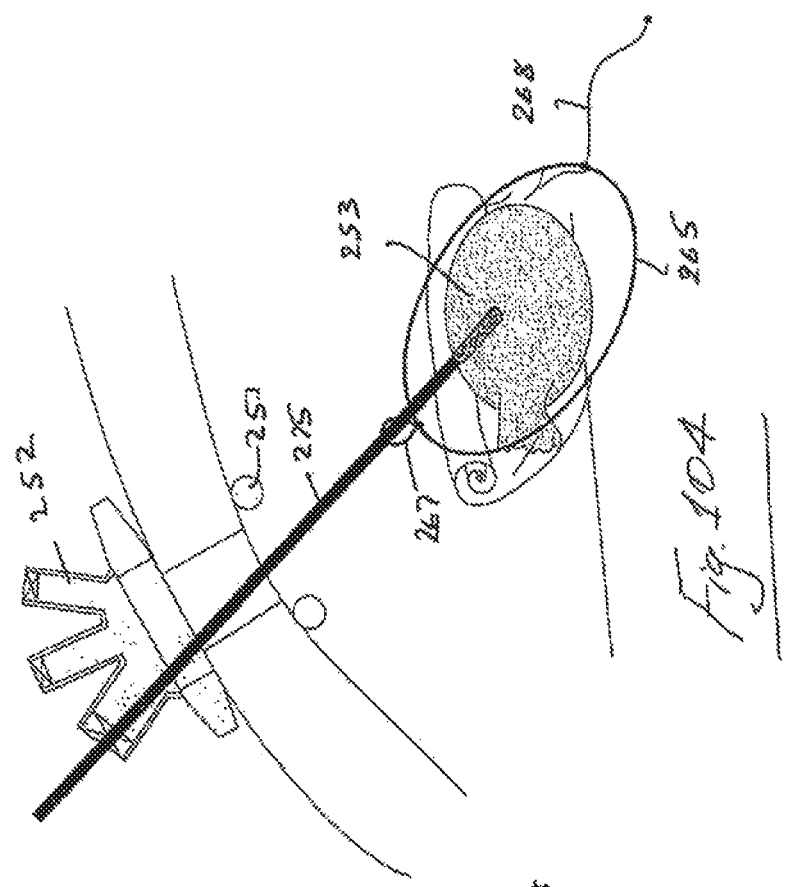
Figure 103:
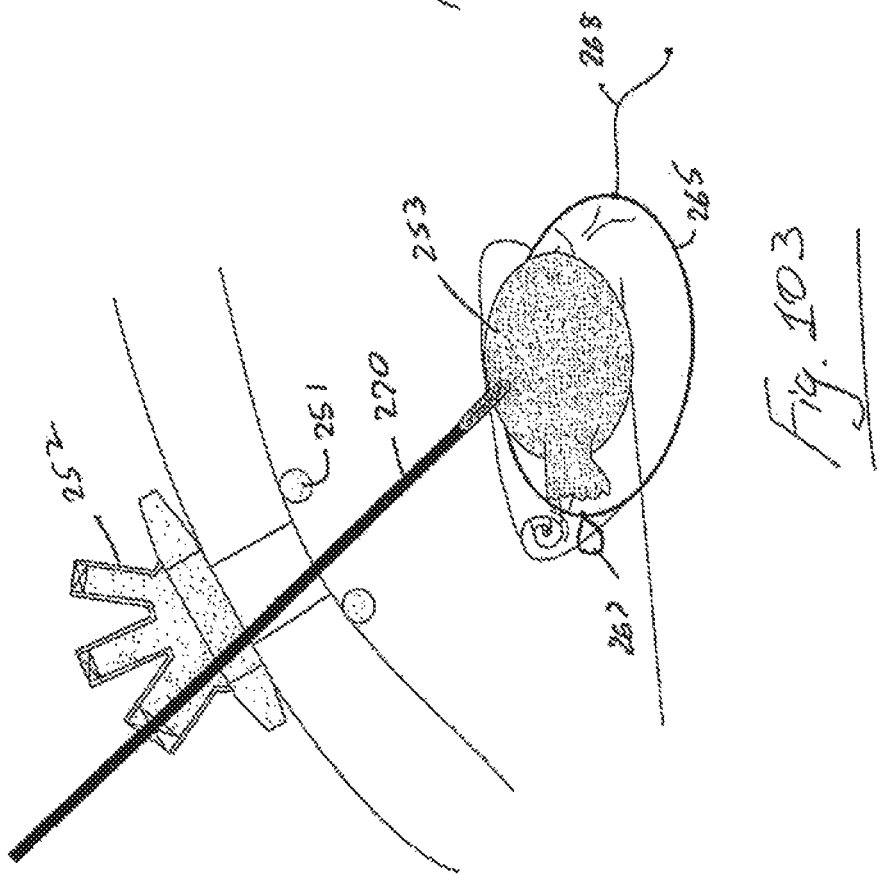
Figure 106:
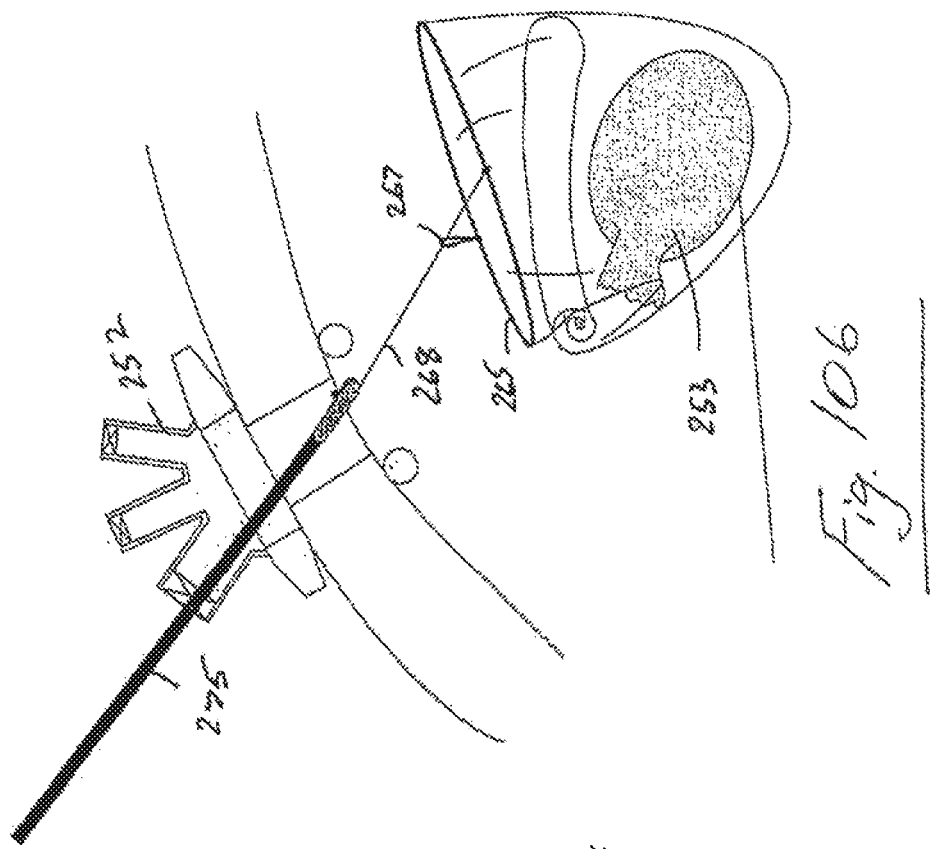
Figure 105:
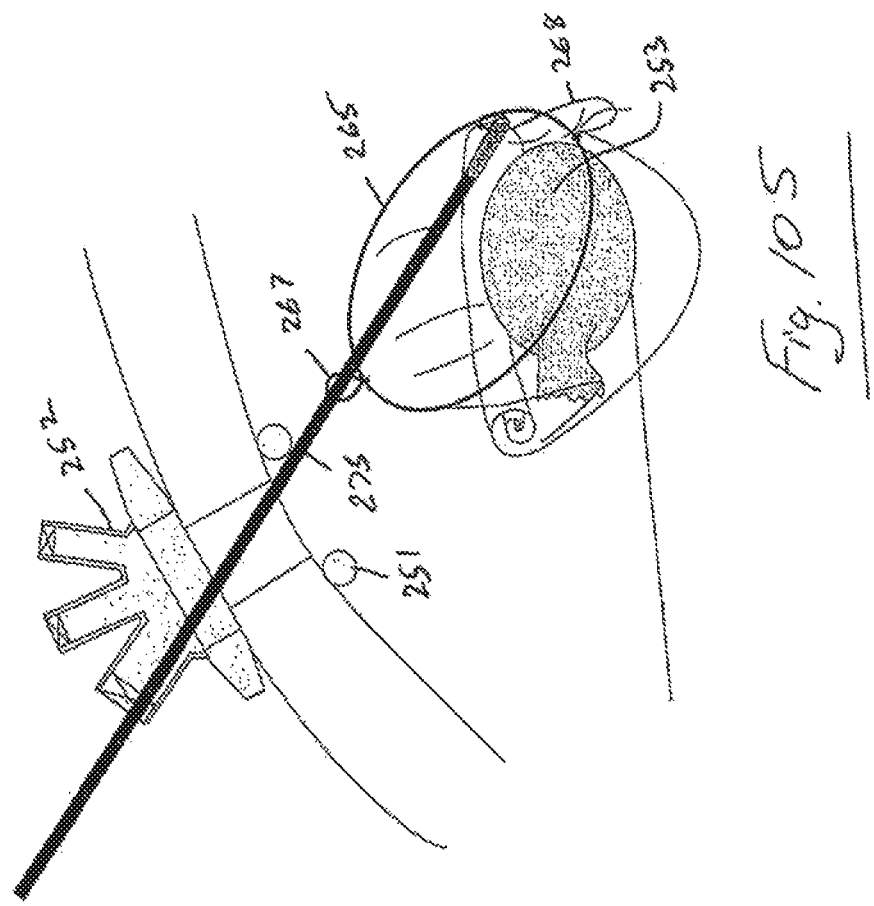

In FIG. 99 the bag device is placed in the delivery configuration in the cartridge or pouch 260. In this case the access port device 252 is in situ on top of the retractor 251 and the cartridge 260 is inserted through one lumen of the access port (FIG. 100). The plunger 261 is used to push the bag device 250 out of the cartridge 260 (FIG. 101). In this particular case the bag device is not tethered to the user, on delivery. On delivery into the body cavity, such as the abdomen, the retractor ring is free to move to its normally expanded configuration in which it opens up the bag opening (FIG. 102). The bag is folded in the delivery configuration. Using various instruments 270 a clinician manipulates a tissue specimen, organ or the like and then delivers it into the bag 250 through the open mouth of the bag (FIGS. 103, 104). FIGS. 105 and 106 illustrate one particular way in which the bag containing the tissue is retrieved. A grasper type instrument 275 is led through the proximal tether loop 267 and is used to grasp the distal tether 268 (FIG. 105). The distal tether 268 is pulled through the proximal tether loop 267 which ensures that the clinician has control over the bag as it is moved up towards the body opening (FIG. 106). As the retaining ring 265 engages with the retractor 251 it retracts allowing it to be pulled up through the body opening (FIG. 107). The access port 252 is removed and the retaining ring 265 is again free to expand (FIG. 108).

The access port 252 is re-attached and the bag is inflated to increase the operative field. The tissue sample can then readily by worked on (FIGS. 109, 110) without the risk of any potentially harmful material being released into the body cavity.

In some cases there may be a lock feature which prevents movement of one tether relative to the other in some directions. One such lock feature is illustrated in FIGS. 111 to 113. The distal tether has a one-way step feature 280 which permits the distal tether to pass through the proximal loop tether but once it has passed through this reverse movement is prevented as illustrated in FIG. 113. This ensures even greater control on the movement of the retaining ring 265 to aid closing of the bag as the ring 265 is being withdrawn.

As discussed above, the devices of the invention may be used in any suitable body cavities. One such use is in the colon and one embodiment for this use is illustrated in FIGS. 114 to 117. The device may be inserted as described above. Once in place and inflated a clinician can inspect the wall of the colon for any unusual features such as a growth. One such growth 280 is illustrated in FIG. 115. In this case, when a growth 280 is identified some or all of the growth 280 may be accessed by cutting a hole in the wall of the bag which remains in place by virtue of its engagement with the rest of the colon. Using various instruments, at least a portion of the growth 280 can be excised and removed through the bag. As in the other embodiments described a major advantage is that the tissue to be removed is retained in the bag which prevents potentially harmful material such as cancerous cells from being released in the body cavity.

Referring to FIG. 118 there is illustrated another bag device 400 of the invention. The bag device has a neck or collar region 401 between a retaining ring 402 and the main body of the bag. Because the retaining ring 402 is of smaller diameter than that of the bag it is more easily inserted through an access port. As shown in FIG. 118, the bag device 400 includes joined planar sheet portions forming the neck region 401 and a body portion 403. Also as shown in FIG. 118, the body portion 403 forms a closed cavity in fluid communication with the neck region 401, and the body portion 403 has a length and width greater than a length and width of the neck region 401. As also shown in FIG. 118, the retaining ring 402 is configured to bias the bag opening toward an open condition.

FIG. 119 illustrates another bag device 410 and shows how the main body of the bag may be folded in the retracted delivery configuration.

Referring to FIGS. 121 and 122, there is illustrated a bag 500 for use in laparoscopic surgery having an opening 502 to receive tissue and a cuff or collar 503 extending around the opening 502. The bag 500 may be inflatable.

The bag 500 comprises a main body 505 which extends from the cuff 503. The main body 505 is more flexible than the cuff 503 to assist in retaining the bag 500 open in the deployed configuration. The cuff 503 may be of a different material than that of the bag 500 or may comprise the same or a similar material which is thicker than that of the main body 505 of the bag 500. In one case the cuff 503 is of a plastics material and the main body 505 of the bag 500 is of a plastics material which is more flexible than that of the cuff 503. However, the cuff 503 is sufficiently flexible to allow closing of the opening 502. A joint 507 between the cuff 503 and the main body 505 of the bag may be reinforced in any suitable manner such as by using a double layer of the cuff material as illustrated in FIG. 3.

The cuff 503 has an axial extent which is important in maintaining the opening 502 in a fully open configuration. This has the major advantage that tissue can be more readily manoeuvred into the opening 502 by the surgeon performing a laparoscopic procedure through a small opening. When the bag 500 is in the open configuration the surgeon is able to concentrate on manipulation of the tissue/material to be inserted into the bag 500 without the added task of complex manipulation of the bag 500 at the same time as the material is being manipulated. Thus, the bag 500 greatly facilitates the laparoscopic surgical procedure.

The cuff 503 extends axially for a length which is sufficient to ensure that the opening 502 remains open to provide an axially extending delivery mouth into the main body 505 of the bag 500. For example the cuff 503 may extend for an axial length of from 2 to 20 cm, 2 to 10 cm, or about 5 cm. Alternative size dimensions for the cuff or collar 503, as well as sizes for other features of the bag, will be discussed in more detail below.

In the invention the cuff 5033 is biased into the open configuration. In this case the bag 500 comprises a biasing element to bias the cuff 503 into the open configuration.

The biasing element may comprise a loop 510 extending around the cuff 503. The loop may be of a shape memory material such as Nitinol. The loop 510 extends round the cuff 503 in any suitable manner. It may, for example, be threaded through the cuff as illustrated or may extend through a table or track provided in or on the cuff 503.

The cuff 503 has tabs 511, 512 which may be used for more readily grasping the bag during a laparoscopic procedure.

A tether 515 extends from the cuff 503 and may be used to activate the opening and/or closing of the bag 500.

Referring to FIG. 120, the bag 500 is folded and housed in an introducer sheath or pouch 520 ready for deployment. Any suitable insertion tool may be used to deliver the bag 500 through an opening. The bag 500 may be deployed in any suitable manner such as by using a plunger 516 which a user activates to deliver the bag from the introducer 520.

Figure 127:
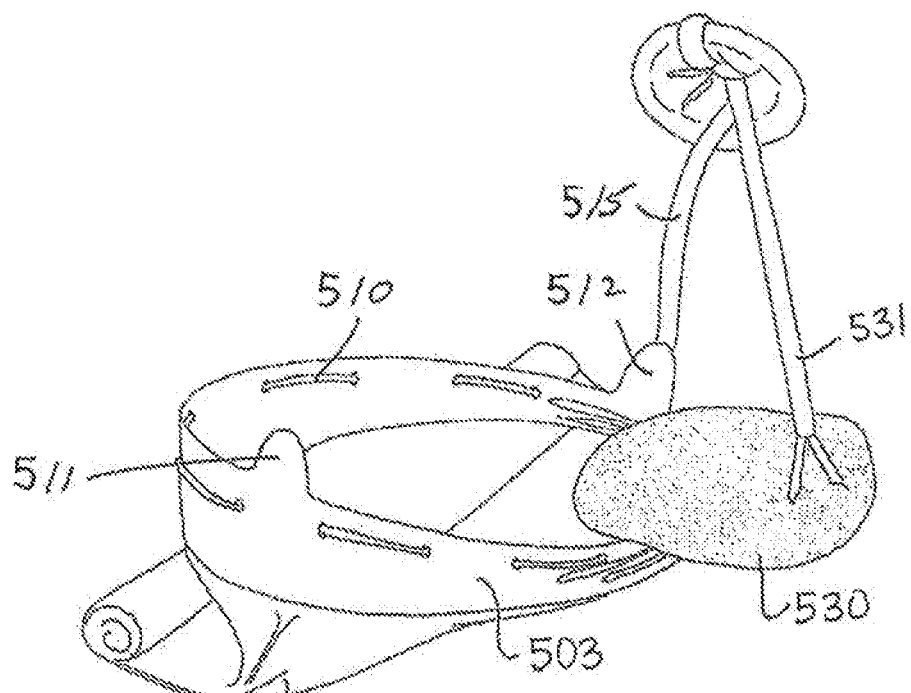
FIGS. 127 and 128 are isometric views illustrating the delivery of tissue into the bag.
Figure 128:
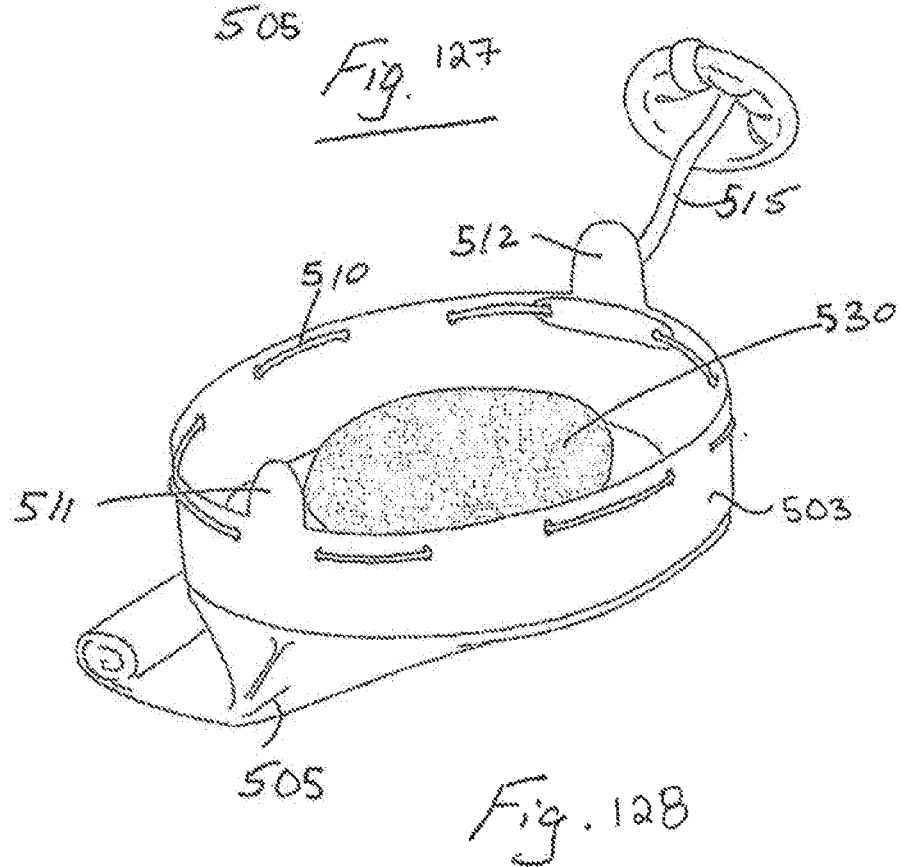
Figure 134:
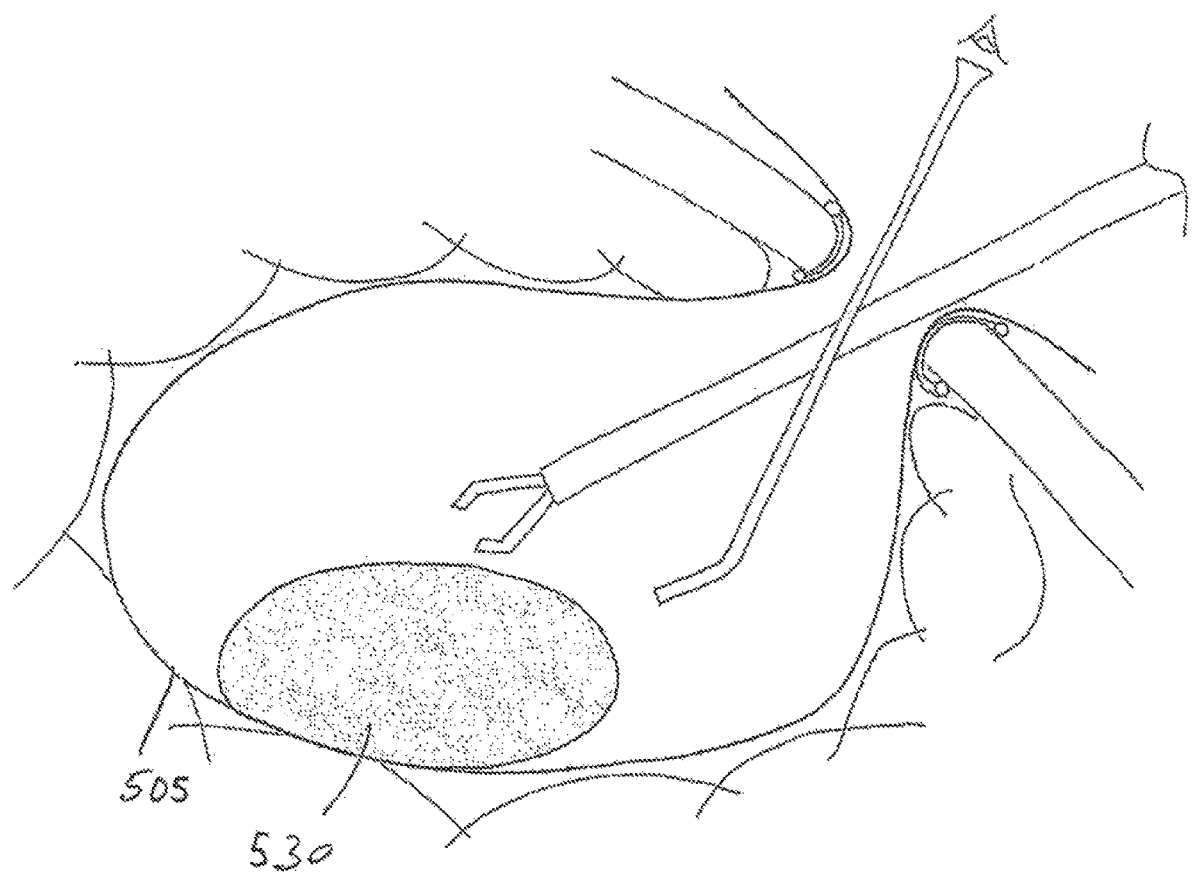
Figure 135:
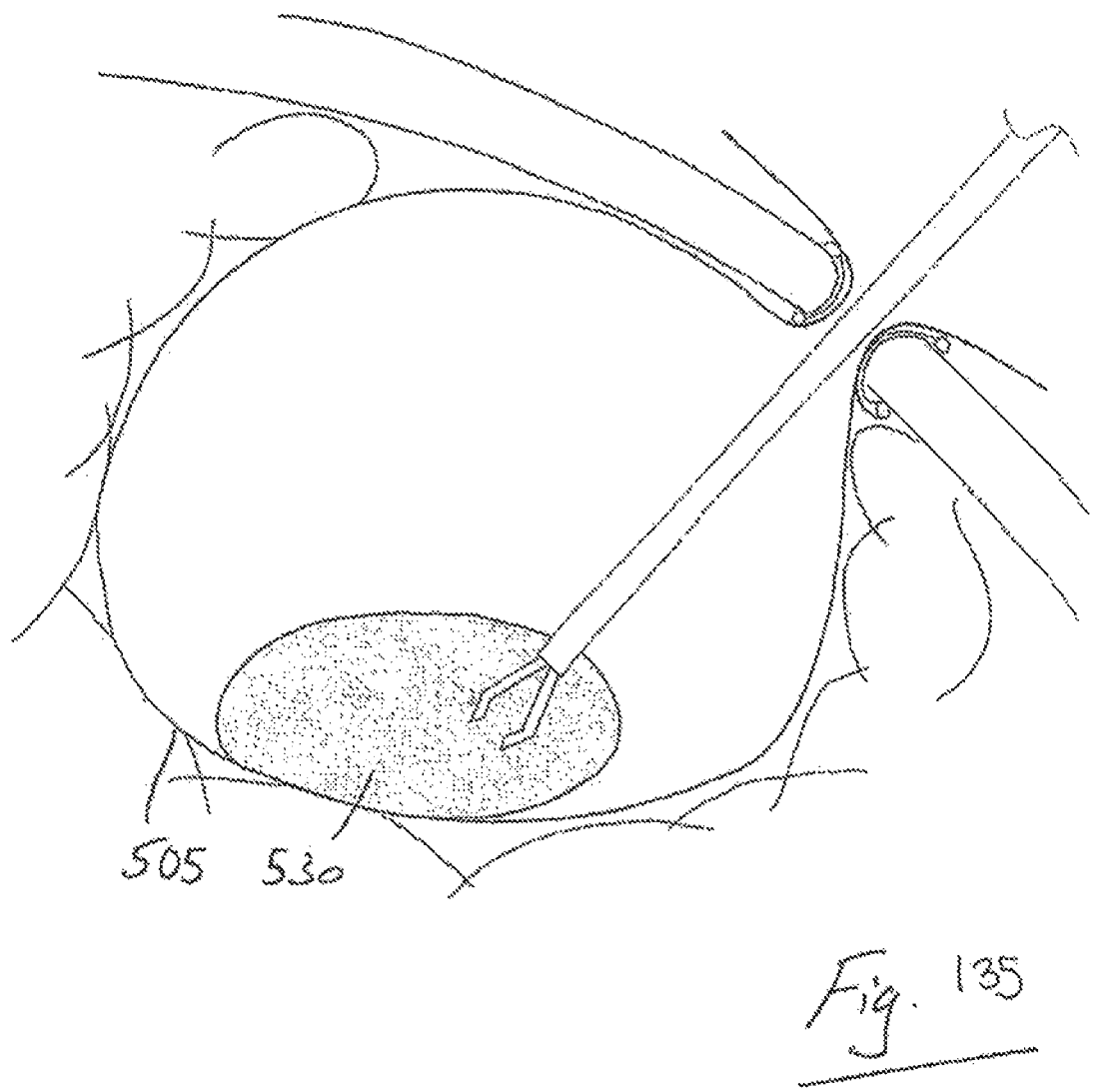
Figure 136:
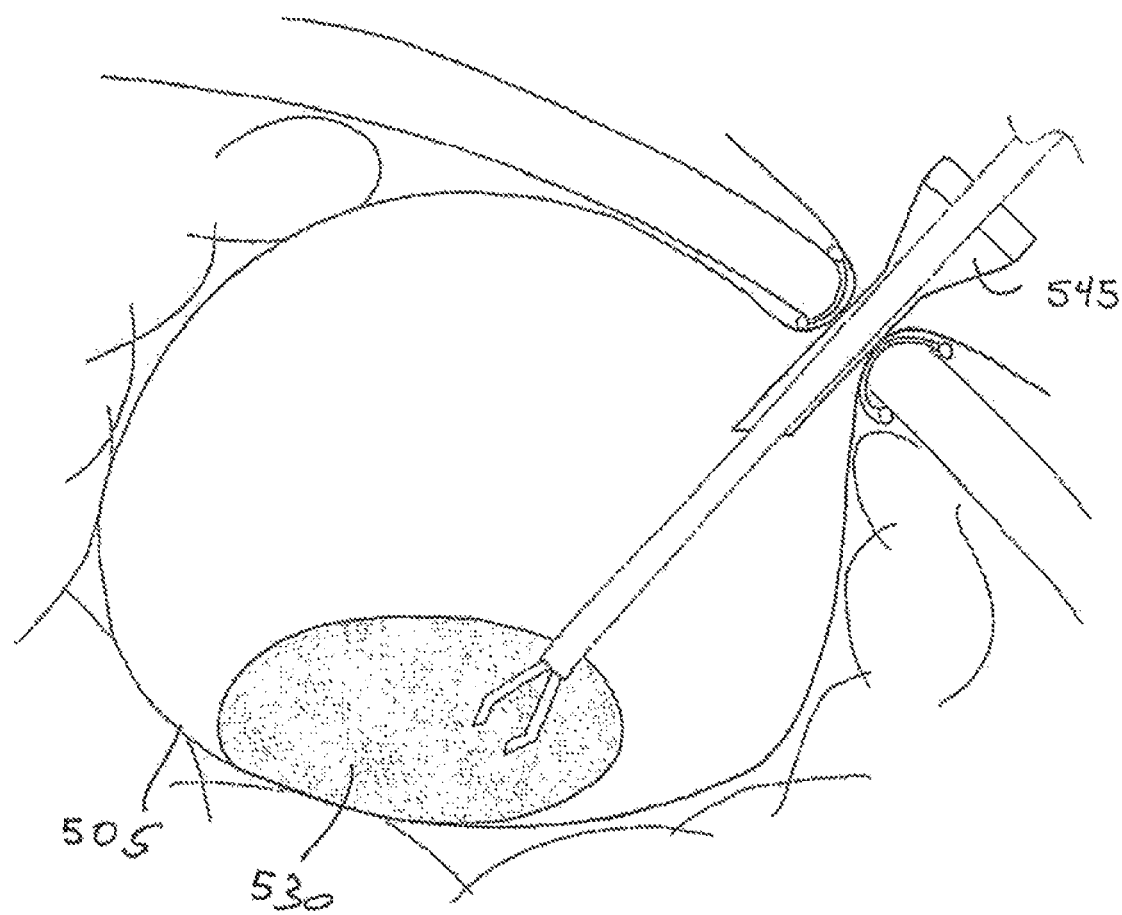

The deployment of the bag 500 through an opening such as a retracted incision 525 is illustrated in FIGS. 123 to 126. As soon as the bag starts to exit the pouch the cuff 503 opens up and when fully deployed defines an axially extending open mouth. FIGS. 127 and 128 illustrate tissue 530 being manipulated into the open mouth of the bag 500 using an instrument such as a grasper 531. When the tissue 530 is in the bag 500 the tether 515 is used to pull the cuff 503 which initially closes the opening and is then pulled out through the tissue opening 525. When the proximal end of the bag 500 has passed through the tissue opening the bag 500 may be inflated and a procedure carried out on the tissue isolated within the bag 500. This may be carried out in several different ways, depending on the procedure being performed. For example, the bag entrance may be closed with an access port 540 as illustrated in FIG. 133 which facilitates access of any suitable instruments to perform procedures such as morcellation of the tissue within the bag 500. Alternatively access is gained to the captured tissue without a requirement for an access port—see FIGS. 134, 135 and 138. Alternatively a trocar 545 may be provided through which an instrument is passed (FIG. 136). There may be additional trocars 550 used (see FIG. 137, for example).

The collar/cuff 503 may be collapsible to allow tissue to be rolled into the bag opening 502 rather than being lifted into the bag opening 502.

The bag 500 may be mounted to a retractor. One such retractor comprises a distal anchoring ring, a retractor member such as a sleeve, and a proximal ring assembly. One such retractor is described in US 2005-0090717 A, the entire contents of which are incorporated herein by reference. The distal anchoring ring is located within a wound interior, in use. In this case the distal anchoring ring is provided in the form of an O-ring. The proximal ring assembly is located externally of a wound opening, in use. The retractor member may be employed to retract laterally the sides of a wound opening. In one case the retractor member is provided in the form of a sleeve.

The proximal end of the retractor is closable by a cap which may comprise an instrument access device 540 which may have a number of instrument ports to effect a seal around an instrument extended through the device. The instrument access device may be releaseably mountable to a proximal ring assembly of a retractor. At least some of the instrument ports may include a stalk which is laterally flexible and longitudinally rigid. One such instrument access port is described in U.S. Pat. No. 8,187,178 or US2011-0071389A, the entire contents of which are incorporated herein by reference.

FIG. 127 shows an organ or tissue such as an uterus which has been severed/amputated from it's retaining structures.

FIGS. 123 to 126 illustrate the bag device being inserted into the abdominal cavity at the beginning of a procedure or as and when required. The bag is inserted in a small flattened state for ease of insertion through a small opening such as an incision. The bag may also be introduced through a valve without the need to remove an access cap.

When the bag is inserted it is opened up. An organ 530 is then readily manipulated for insertion into the bag as illustrated in FIG. 128. The relative rigidity of the cuff 503 keeps the bag open to facilitate insertion of an organ.

Figure 129:
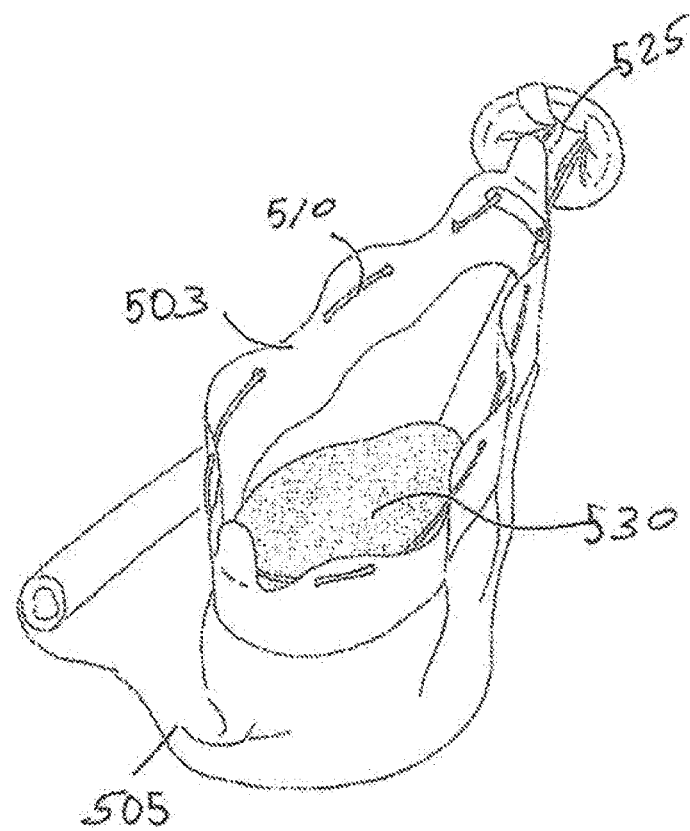
FIGS. 129 and 130 are isometric views illustrating the closing of the bag.
Figure 130:
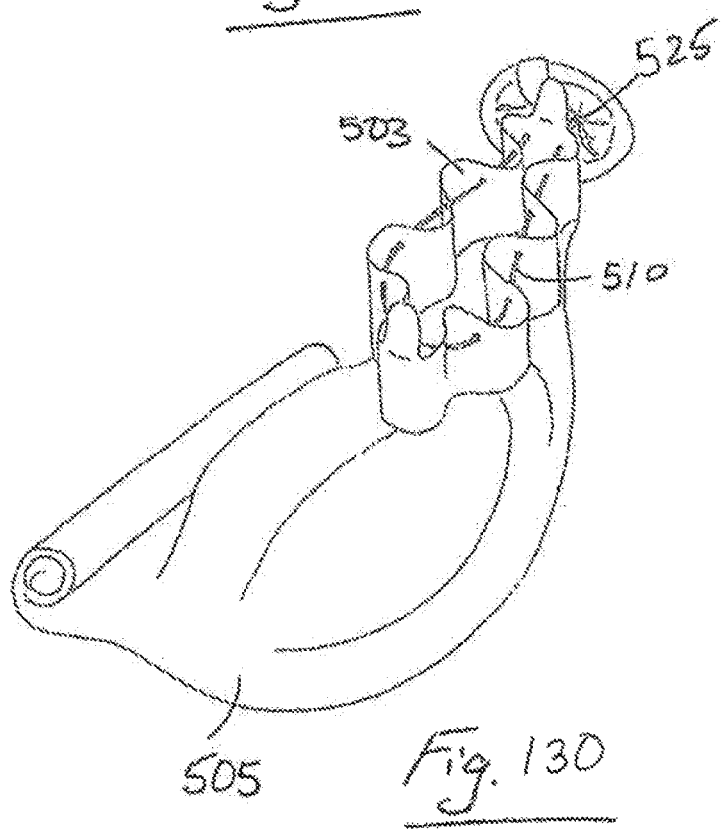

FIG. 129 shows the organ located in the bag and the cuff 503 being grasped to facilitate manipulation of the bag towards the opening. The cuff 503 is pulled out through the opening. The bag may be mounted to a proximal ring assembly of a retractor and a cap may be mounted to the proximal assembly. FIG. 131 illustrates the device in place with an organ enclosed within the bag.

The bag is then inflated (FIG. 132) through an insufflation port. The inflation of the bag has the additional benefit of applying a retracting force to the materials outside the bag thereby creating additional space.

FIG. 133 shows an organ being worked on in the inflated bag. The organ may be morcellated. The material is all retained safely within the bag and is not released into the cavity which could cause major difficulties. The bag is retained externally, for example by clamping/connecting to a retractor.

When the organ has been morcellated the bag is readily removed through the original opening. All waste, blood, tissue and the like are safely removed and sealed within the bag.

The bag device may be inserted through a standard naked incision. Once the specimen has been inserted into the bag an opening such as a cuff 503 is pulled back out through the incision and a trocar may be inserted to create a gas seal. The bag device may also be inserted directly through a trocar as illustrated in FIG. 136.

In some cases there may be one or more access trocars used in addition to the primary port. Thus, the invention includes procedures which involve two or more incision laparoscopy.

Figure 137:
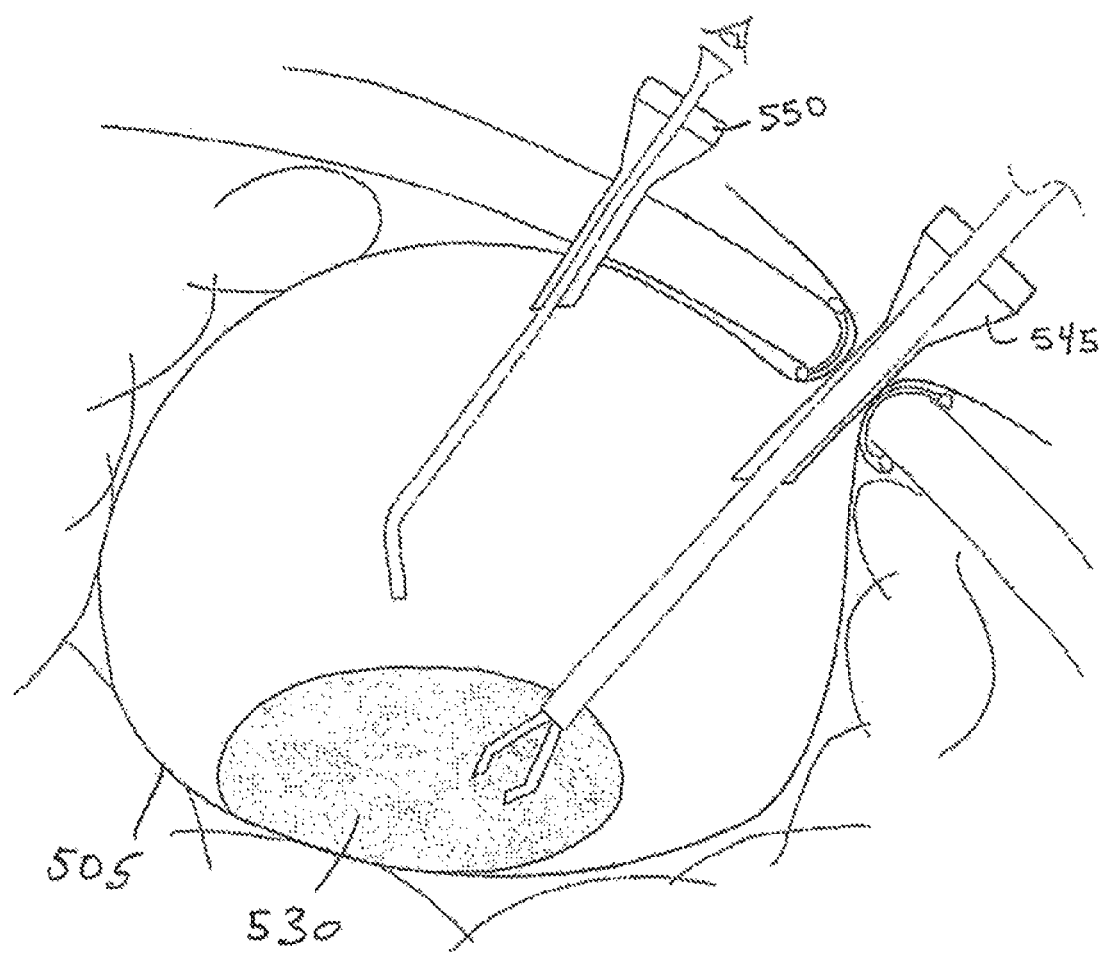

For example, FIG. 137 shows one arrangement in which an additional trocar is inserted. In some cases, the additional trocar may be extended through the bag whilst maintaining a seal.

The invention provides a method of inserting a large bag into the abdominal cavity to allow the insertion of a specimen into the bag. The bag is then sealed and inflated and procedure carried out within the bag.

As discussed above, the devices of the invention may be used in any suitable body cavities. One such use is in the colon. The device may be inserted as described above. Once in place and inflated a clinician can inspect the wall of the colon for any unusual features such as a growth. In this case, when a growth is identified some or all of the growth may be accessed by cutting a hole in the wall of the bag which remains in place by virtue of its engagement with the rest of the colon. Using various instruments, at least a portion of the growth can be excised and removed through the bag. As in the other embodiments described a major advantage is that the tissue to be removed is retained in the bag which prevents potentially harmful material such as cancerous cells from being released in the body cavity.

Referring to FIGS. 139 to 155 various embodiments of biasing loop elements which may be used in the bag device of the invention to assist in maintaining the bag open are illustrated. In these cases the loop comprises a number of loop parts which are movable relative to one another for loading deployment, and/or retrieval.

Referring to FIGS. 139 to 143 in this case there are two joined loop parts 551a, 551b which are movable circumferentially through hoops 552. In some cases a single piece loop is sufficiently flexible to allow manipulation.

Figure 144:
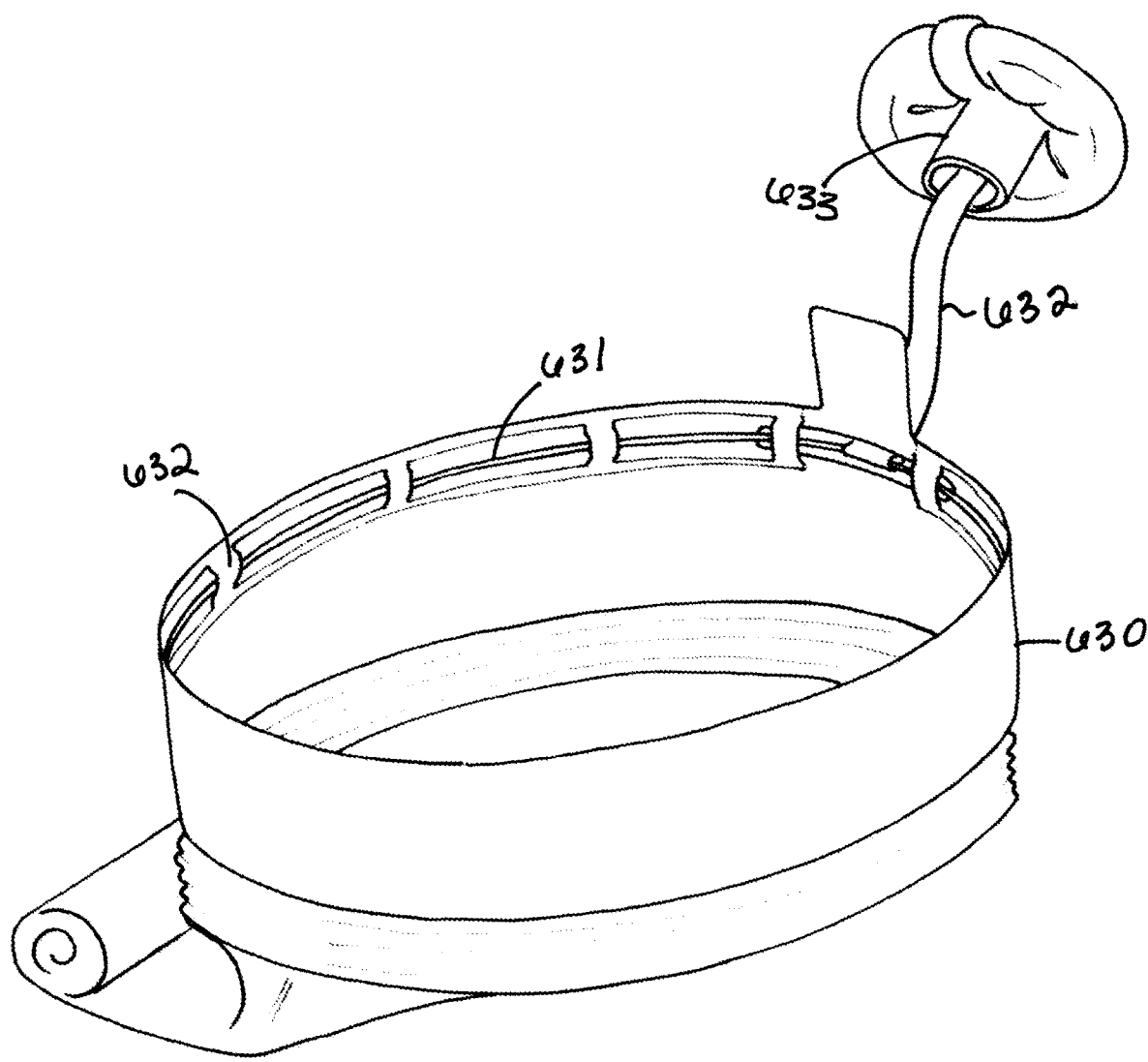

Referring to FIGS. 144 and 149 in this case a loop 560 is configured in the manner of a noose with a leg 561 extending from the loop which may be pulled to reduce the diameter of the loop. There is a closed loop 562 on one end and a kink 563 on the other end which links into the loop 562 to facilitate reducing the diameter of the loop 560.

Referring to FIGS. 150 to 153 in this case there may be closed loops 570, 571 at each end of the retaining loop 572. These may be used as tether attachment points.

Referring to FIGS. 154 to 156 in this case the ends of a retaining loop 580 have bends 581, 582 and extend to define arms 583, 584 which facilitate manipulation of the loop for retrieval.

The device of the invention may include features to isolate the contents of the bag from the wound opening and hence protect from escape of material as could occur with seeding of cancer cells and the like.

Referring to FIGS. 157 to 160 in this case the bag comprises a small opening 600 which remains closed under insufflation pressure. The opening 600 is opened on insertion of an implement such as a trocar 601 through the opening 600. The bag has excess material in the region of the opening 600 which defines a sleeve or chimney 603 which seals along part of the length of the trocar shaft when the shaft is in place in the opening 600. The opening 600 is located at the top of the bag, in use i.e. in the region that touches the abdominal wall. A trocar 601 may be inserted in a region of the abdominal wall remote from key organs and manipulated under full vision to locate the opening. The opening stays closed whilst there is internal insufflation pressure and the sleeve or chimney 603 collapses around the trocar to create a seal.

Figure 161:
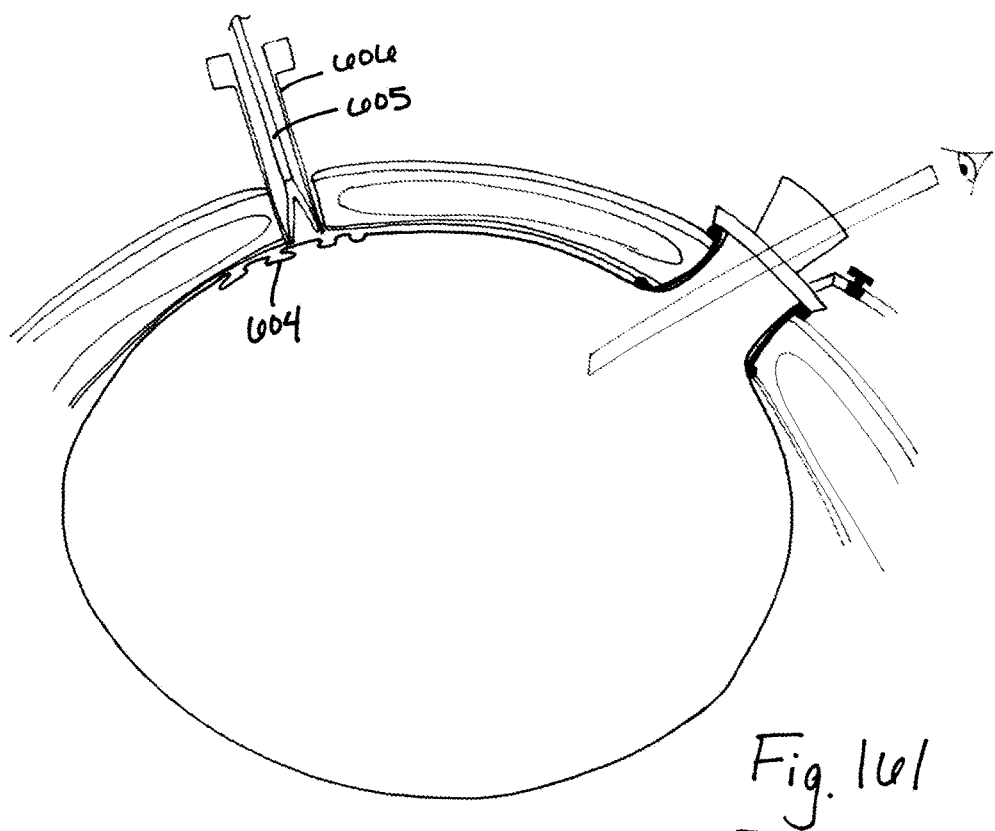
FIGS. 161 to 164 illustrate another bag device of the invention in use.
Figure 162:
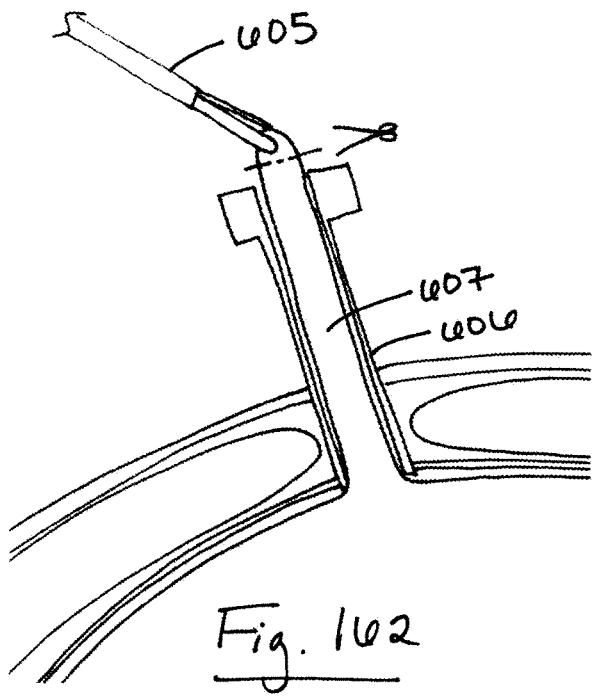
Figure 163:
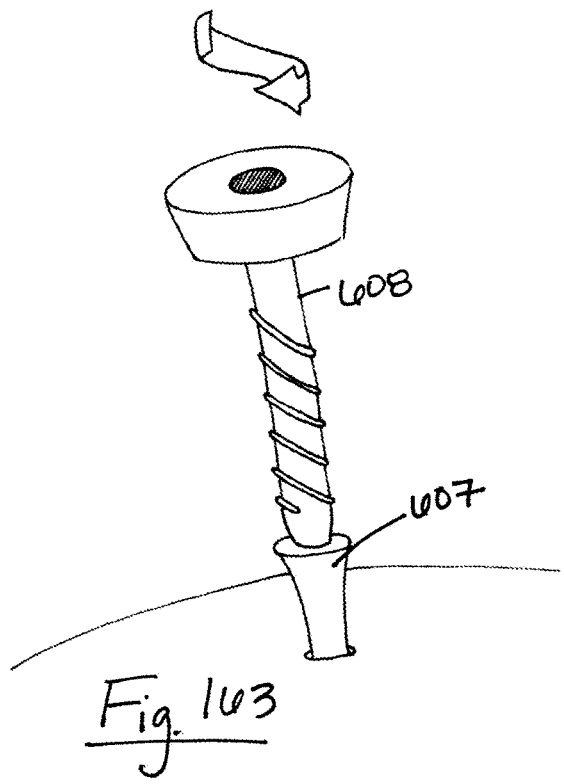

Referring to FIGS. 161 to 163, in this case any excess bag material 604 may be grasped using a grasper 605 inserted through a trocar 606. The end of the excess material may then be cut (FIG. 162) creating a chimney 607 extending from the bag. The chimney 607 is then sealed—for example using a threaded trocar 608 which is twisted inside the chimney 607 to create a seal. The chimney 607 prevents contact between the wound and debris created during morcellation. In this case the surgeon is provided with an additional port into the bag for use during the procedure. One such procedure may involve insertion of a laparascope or a grasper, for example through the secondary port.

Figure 164:
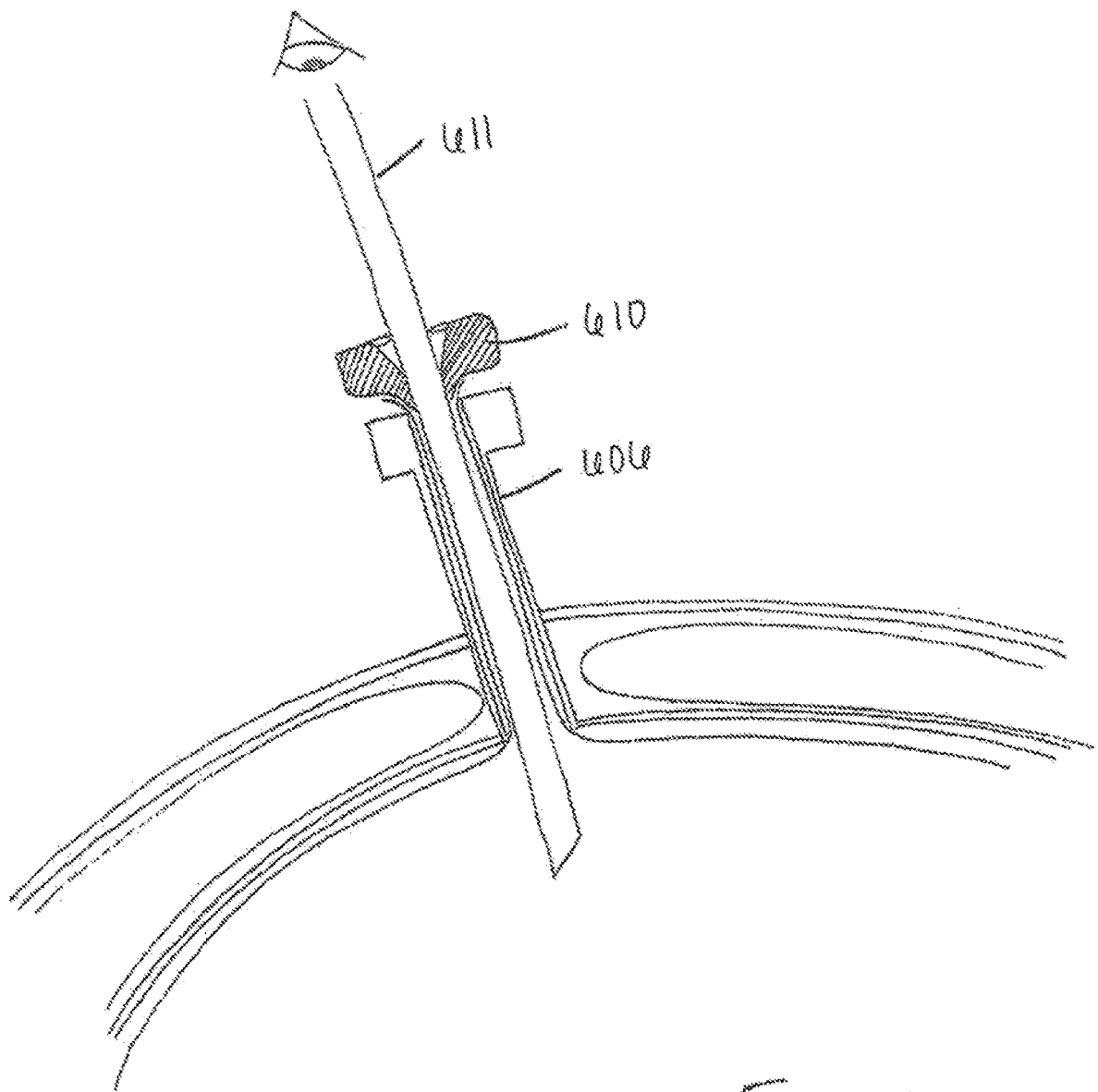

Referring to FIG. 164, in another embodiment a bung 610 may be placed inside the trocar 606, sealing the bag to the trocar. An implement such as a laparascope 611 may be inserted through the bung 610.

Figure 165:
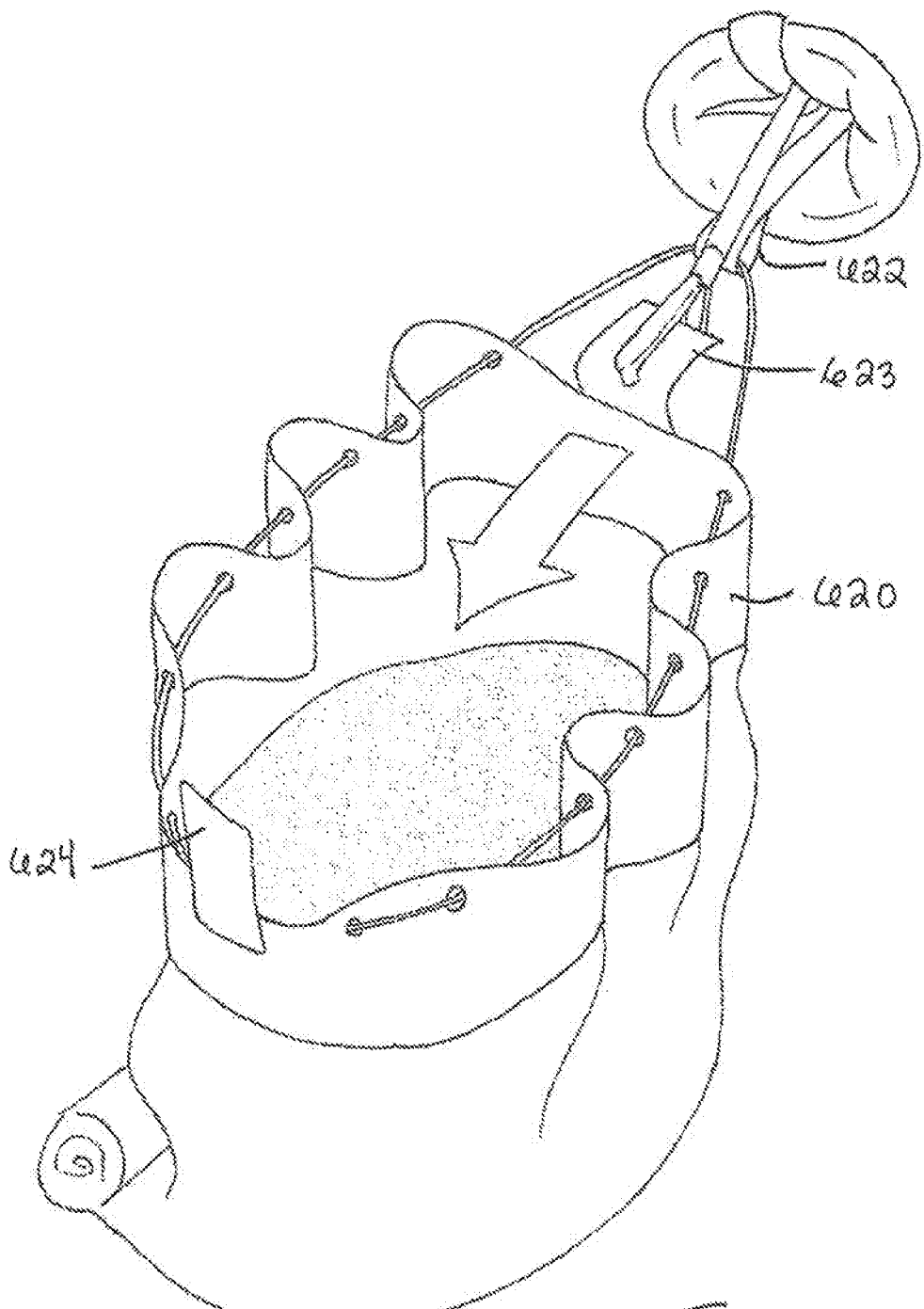
FIG. 165 is an isometric view illustrating closing of a bag device.

Referring now to FIG. 165, in this case the bag has a cuff 620 and a tether 621 loop is threaded through the cuff. The tether 621 has a strap 622 which may be used to pull on the tether from a location external of the abdomen. The cuff 620 also has grasping tabs 623, 624. In this case a grasper 625 may be used to grip the tab 623 as illustrated and then push the cuff towards the opposite side of the bag, towards the tab 624, thus closing the bag. The strap 622 enables the bag to be held firmly whilst being closed within the pneumoperitoneum.

Figure 185:
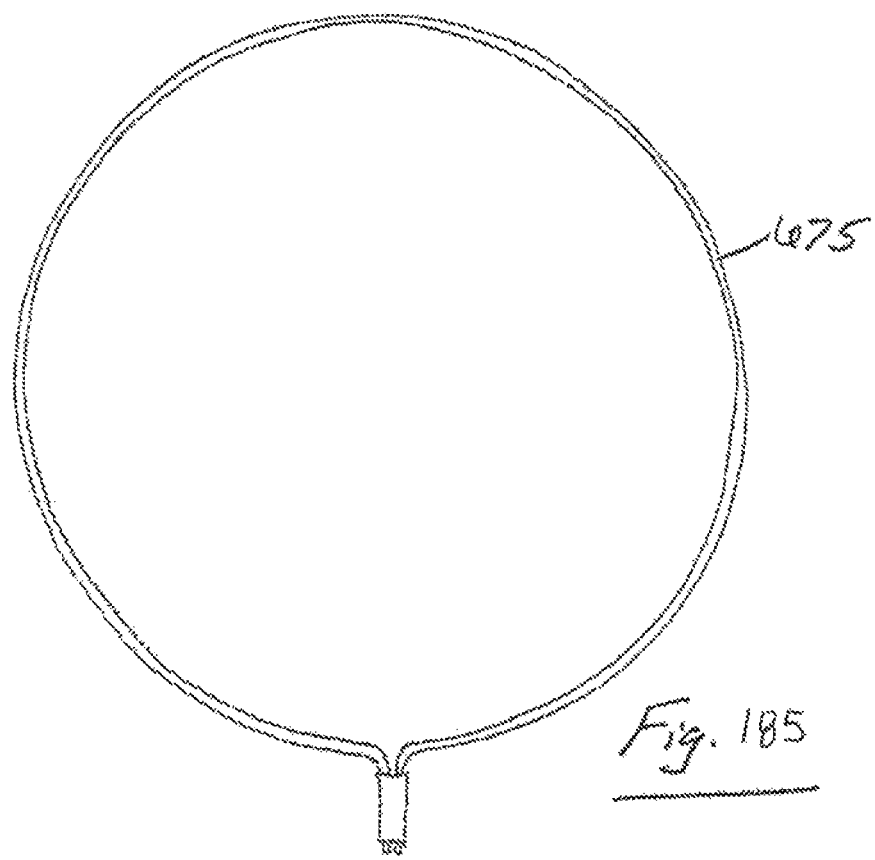
FIGS. 185 and 186 illustrate a retaining ring of the bag.
Figure 186:
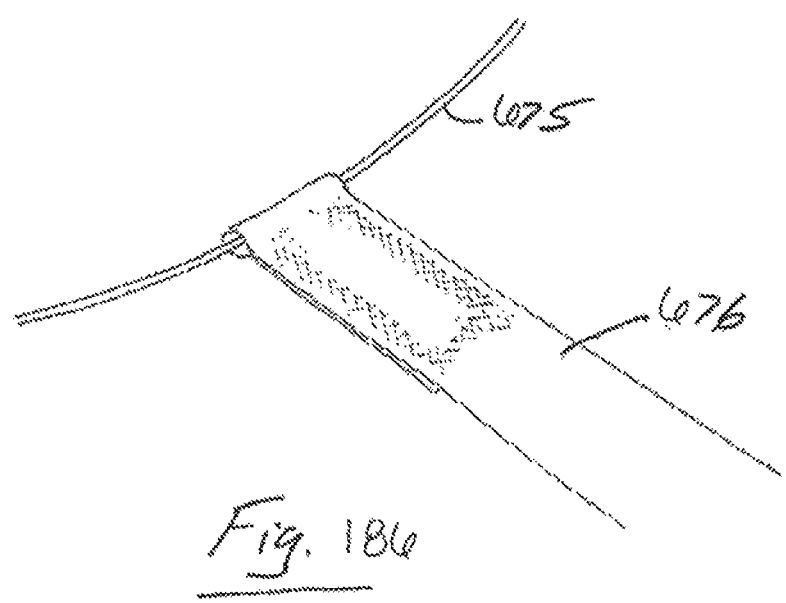
Figure 187A:
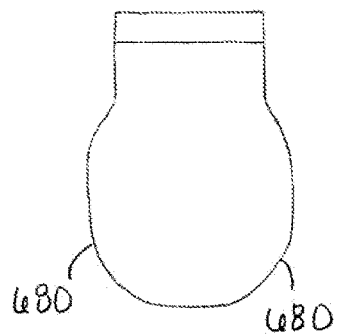
FIGS. 187(a) to 187(f) are views illustrating the loading of a bag device into an introducer.
Figure 187B:
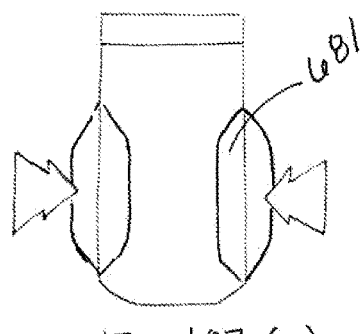
Figure 187C:
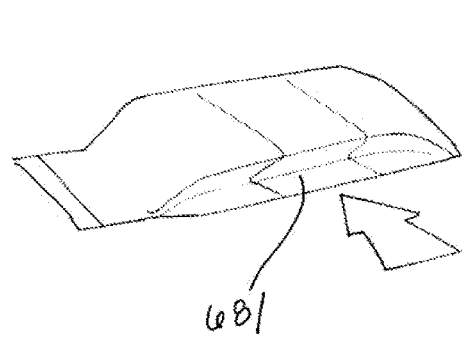
Figure 187D:
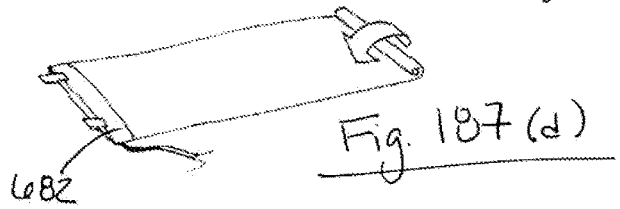
Figure 187E:
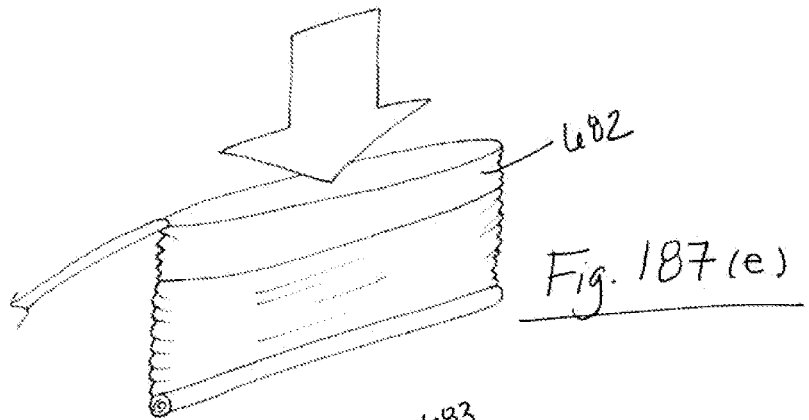
Figure 187F:
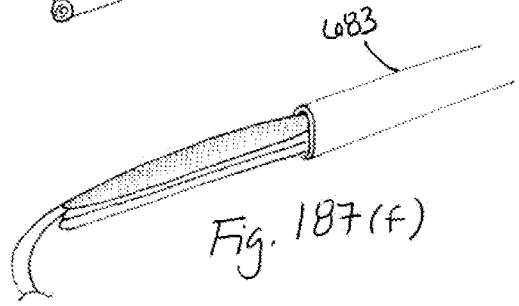

In some cases the bag is retained in the normally open configuration by a retainer ring of a shape memory material such as Nitinol. It has been found that a single ring formed by attaching, for example by welding, together the ends of a ring-forming member is most efficient in achieving rapid deployment. Referring to FIGS. 185 and 186 the retaining ring of the bag may be manufactured in any suitable manner. In one case, for example, a shape memory material 675 is formed into a loop, shape set and welded. A tether strap 676 may also be attached in any suitable manner.

In some cases the cuff of the bag may have features to facilitate mounting of the pre-formed ring to the bag.

In one embodiment illustrated in FIG. 166 the bag has a cuff 630 through which a loop 631 of a shape memory material such as Nitinol is led. Internal capturing regions 632 for the retaining loop 631 are created by cutting panels in the material of the bag and folding down over the retaining loop 631 and sealing using a suitable tool such as a circular sealing tool. A tether strap 632 is mounted to the loop 631 and extends through an access port 633 to maintain control over the bag.

Figure 167:
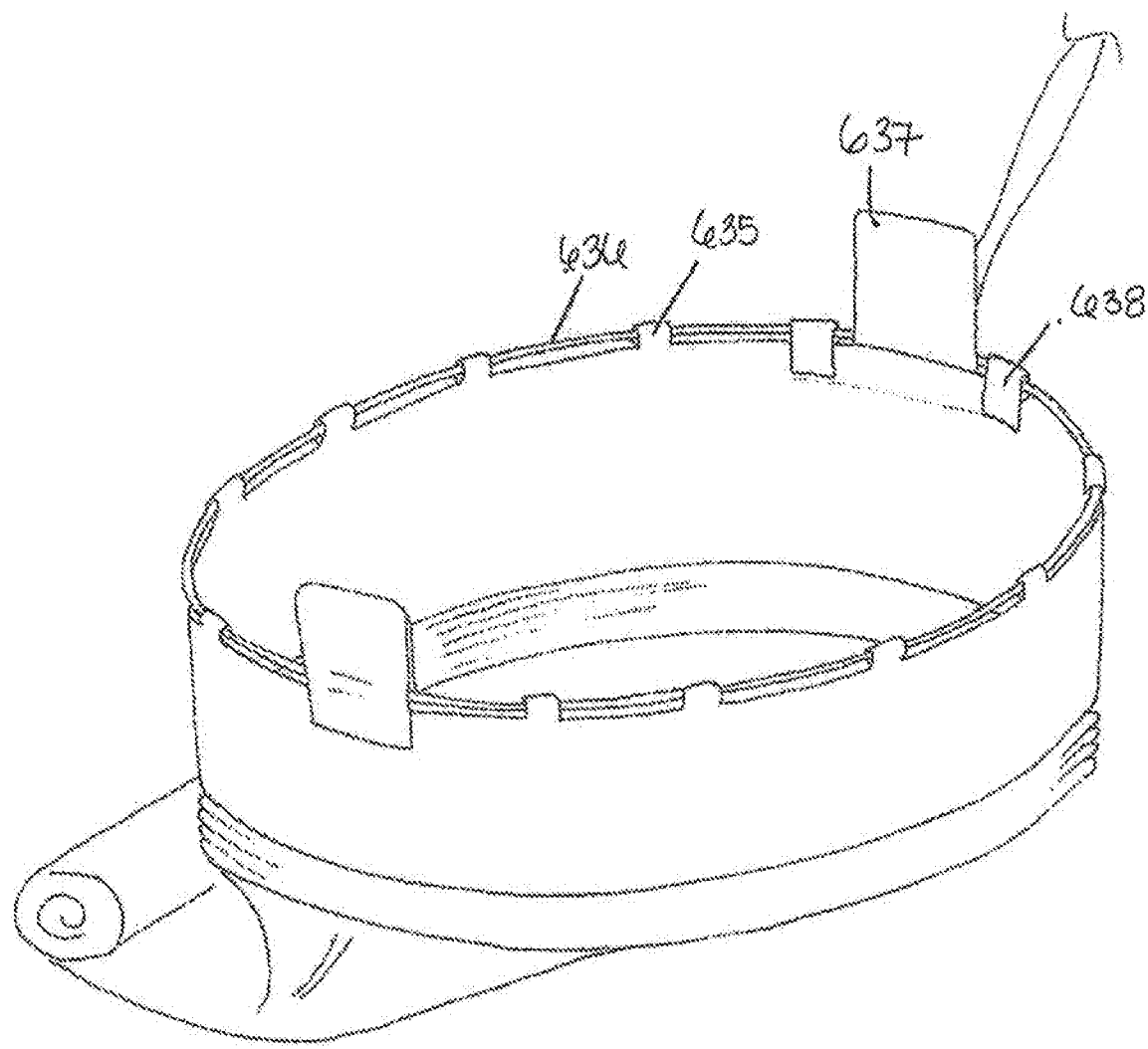

Referring to FIG. 167, in this case pressed out attachments 635 are folded over a closed retaining loop 636 of a shape memory material such as Nitinol and sealed, for example by heating. A front grasping tab 637 includes reinforced attachment loops 638.

FIGS. 168 to 170 illustrate another method of attaching a retaining loop 640 to a cuff 641 of a bag according to the invention. In this case the material of the collar or cuff 641 is punched out with a cut detail 642 extending from a hole 643 (through which the retaining ring 640 is extended) to the edge of the cuff. The cuff is formed into a collar 641 as illustrated in FIGS. 169(a) to 169(c). The retaining ring 640 is inserted through the cut details 642 and into the receiving holes 643. Using a circular sealing tool, the tabs are folded down to create an alternating overlap. The cuff is then sealed, for example by heat sealing to close the holes 643. In this way a closed loop 640 of a shape memory material such as Nitinol is attached to the bag to maximise the opening and facilitate insertion of tissue laparascopically when the bag is within the abdomen.

Figure 171:
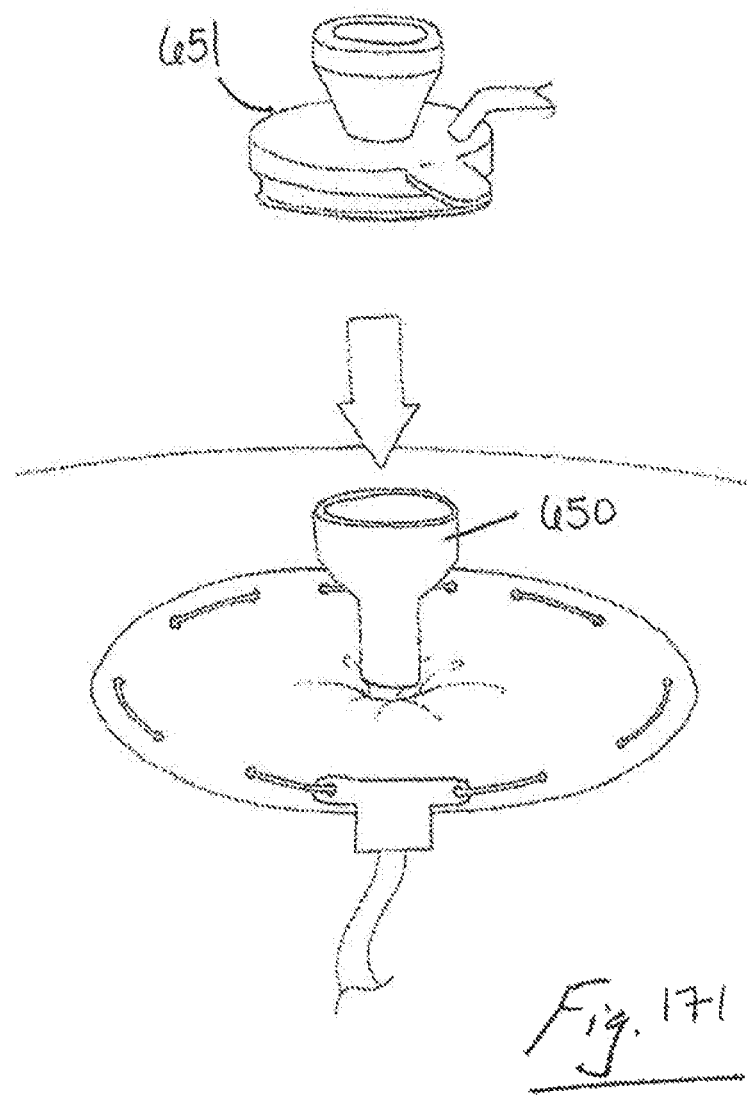
FIG. 171 shows a protector cap for a bag device.

In some embodiments the abdominal bag is protected from damage during use of a morcellator. For example, as illustrated in FIG. 171 an insert/cannula 650 may be inserted to isolate a morcellator from the material of the bag. The insert 650 may for example be rigid, flexible or of a segmented rigid material. An access port or cap 651 may be releasably mountable to the insert 650.

The device used to introduce the bag into an insufflated abdomen may be adapted to control the opening of the bag. For example, as illustrated in FIGS. 172 to 176 a tip 655 of an introducer sheath 656 may have mirrored slots 657 which allow a retaining ring of the bag to start to expand before the full bag is inserted. Such an introducer will aid maneuvering of the bag into a desired position before the bag becomes detached from the introducer. In addition, the deployed bag can be partially withdrawn into the introducer to enable further rigid movement of the bag to optimise positioning.

To limit blood or other material being pushed into the introducer by the positive insufflation pressure within the abdomen the tip of the introducer may have pressure dissipating features. For example, as illustrated in FIGS. 177 to 180 the introducer tip may have various slots 660, holes 661 and/or tapering features 662.

Figure 189:
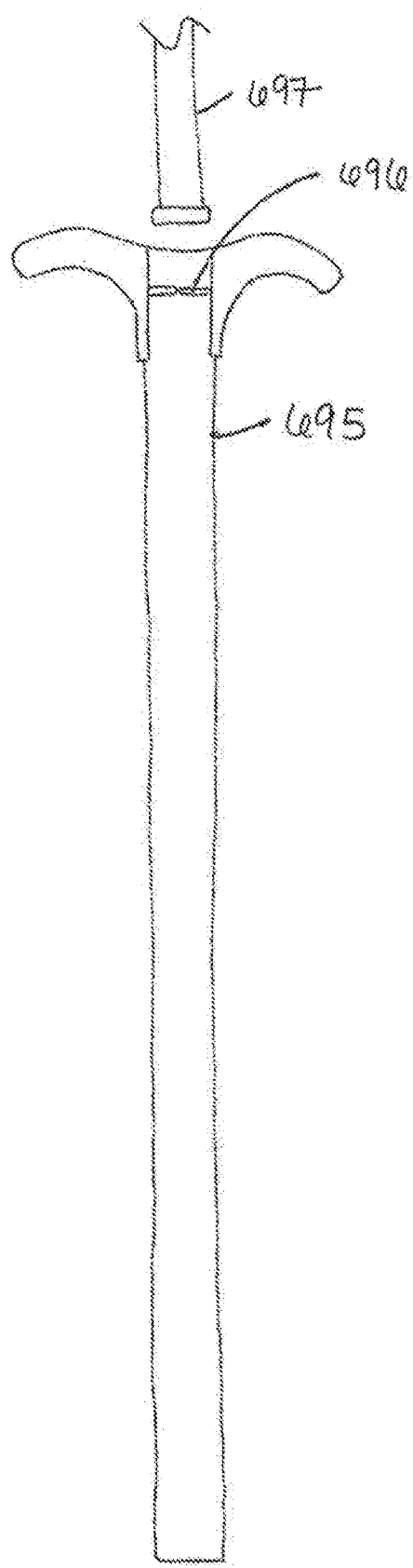
FIG. 189 shows an introducer with a valve.

In another embodiment as illustrated in FIG. 189 to restrict blood or other material from entering the introducer, a shaft 695 of the introducer may have a valve 696 at the proximal end. The valve 696 may be openable on insertion of a pusher 697 used to deploy the bag device from the introducer.

It will be appreciated that the bag of the invention may comprise different materials to fulfil different requirements for sections of the bag. For example, as illustrated in FIGS. 181 and 182 a main body 665 of the bag may be made from a relatively thin flexible material and a collar 666 of a thicker, more rigid material. For example, the main body 665 may include a sterilized polyester polyurethane, such as SS-1495-95 (95 shore A polyester polyurethane blown film with high slop surface and good clarity), and the collar or neck portion 666 may includes a sterilized polyether polyurethane, such as ST-625-85 (85 Shore A polyether polyurethane formulated for medium/high slip with good sealability).

Figure 183:
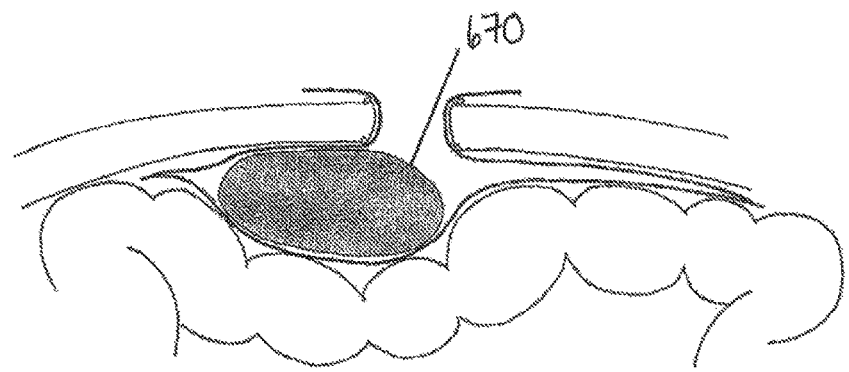
Figure 184:
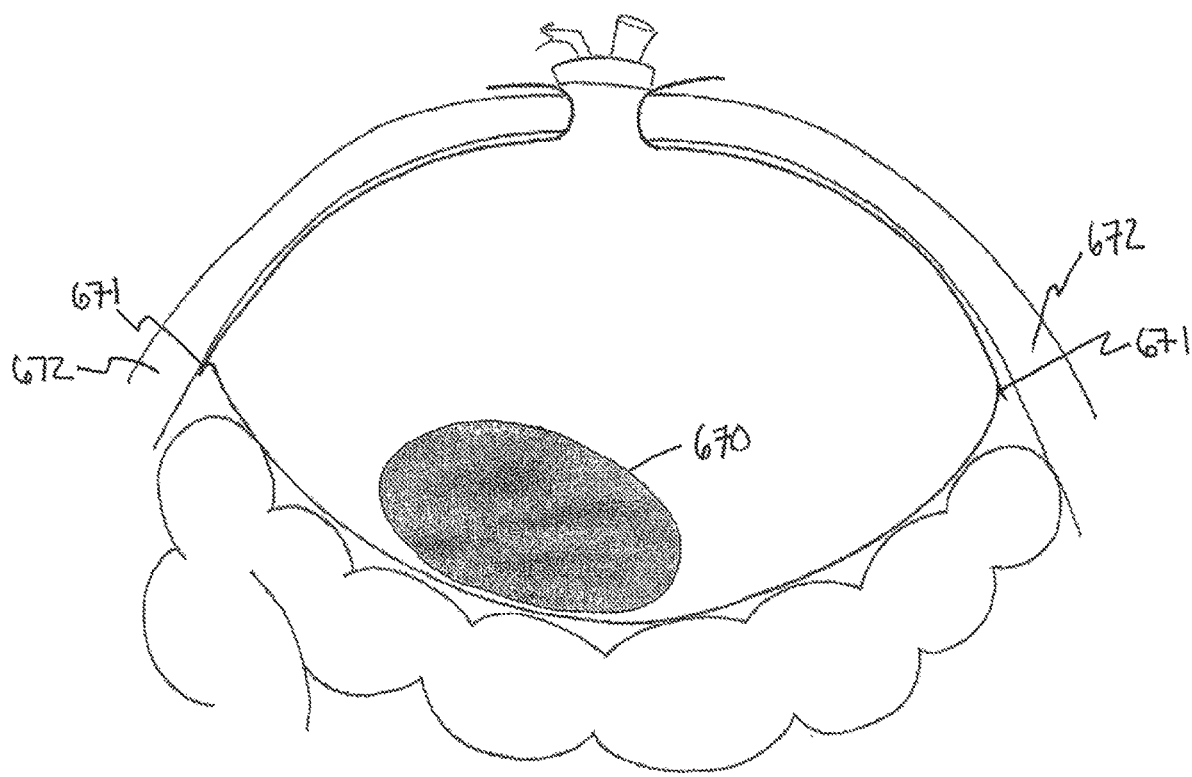

The bag may also be of any desired shape/profile. For example, the bag may be of oval or elliptical profile as illustrated in FIGS. 181 to 184. This shape assists in pushing organs such as a section of bowel away from the abdominal wall which prevents the bowel from migrating over the top of the bag. As shown in FIG. 184, the creation of the artificial pneumoperitoneum includes positioning the joined edges 671 of the bag in alignment with the lateral walls of the abdomen 672 such that one of the planar sheet portions of the bag faces, and is in contact with, the anterior abdominal wall, and the other sheet portion of the bag faces and contacts the visecera. Tissue 670 is illustrated in FIGS. 183 and 184 within the bag.

The bag may be sized to be larger than the peritoneal cavity of the patient so as to provide apposition against the abdominal wall after inflation. The oversized nature of the bag, and the loading of the bag into the introducer as described below in connection with FIGS. 187(a) to 187(f), allows any additional bag material after inflation to remain rolled at the bottom of the bag. This helps to minimize pleats or folds of the inflated bag from extending into the artificial pneumoperitoneum. Consistent with this, and as shown in FIG. 181, the bag may be sized to include a total bag length 661 of between 300 and 600 mm, or between 400 and 550 mm, or approximately 500 mm, all in an uninflated condition. The bag may also include a maximum width 677, for example in the body portion 665, of between 200 and 500 mm, or between 300 and 400 mm, or approximately 350 mm, all in the uninflated condition. The collar or neck 666 may include a constant width 663 of between 150 and 350 mm, or between 180 and 320 mm, or approximately 250 mm, all in a bag uninflated condition and when the neck 666 is flattened as shown in FIG. 181. The collar or neck 666 may also include a length 664 of between 100 and 300 mm, or between 100 and 200 mm, or approximately 150 mm, in a bag uninflated condition. The main body 665 may include a main body length 667 (not including the neck) of between 200 and 500 mm, or between 300 and 400 mm, or approximately 350 mm. Also, main body 665 may be configured to have a maximum width to maximum length ratio of approximately 1:1.

Also, as noted above, the bag may be retained in the normally open configuration by a retainer ring of a shape memory material such as Nitinol. Referring to FIGS. 166-170, the retaining ring of the bag may be formed into a loop, shape set and welded. The diameter of the bag opening when the retaining ring is in an open configuration may be between 100 and 220 mm, or between 120 and 200 mm, or approximately 160 mm.

Referring again to FIGS. 181 and 182 the bag may be formed from shaped flat sheet laid on top of one another and attached at the edges 671, for example by welding. When inflated (FIG. 182), the bag expands into an ovoid type shape with rounder corners which can more closely align with the contours of the abdomen. Also as shown in FIGS. 118, 181, and 182, the bag may be shaped to be symmetric about two different planes (668, 669) that are normal to one another. In addition, as shown in FIGS. 118 and 181, neck or collar portion (401, 666) may be shaped to extend parallel to a longitudinal axis 273 of the bag, and thus edges 674 of the neck or collar portion (401, 666) may extend parallel to the longitudinal axis 273 of the bag.

The bag of the invention in some cases may be manipulated to optimise ease of loading into an introducer and/or to optimise deployment. For example, as illustrated in FIGS. 187(a) to 187(f) the bag may be wider at certain sections 680. These extra width sections may be folded inwardly from the side to form pleats 681. The bag may then be rolled from the bottom up towards the neck 682 of the bag. The neck 682 of the bag may then be scrunched down and loaded into an introducer 683.

Figure 188:
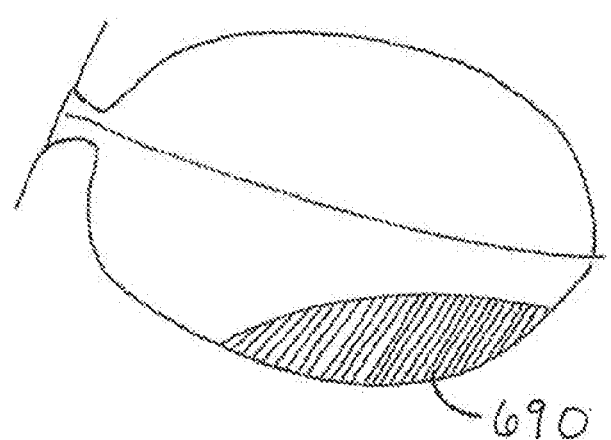
FIG. 188 is an illustration of a bag device with a re-inforced section.

Referring to FIG. 188 in some cases sections of the bag may be of a different material and or material thickness in order to provide desired properties. For example, a bottom section 690 of the bag may be of a stranger/more rigid material to resist the action of a morcellator. The section 690 may be of a rip-stop nylon material, by way of example.

Figure 190A:
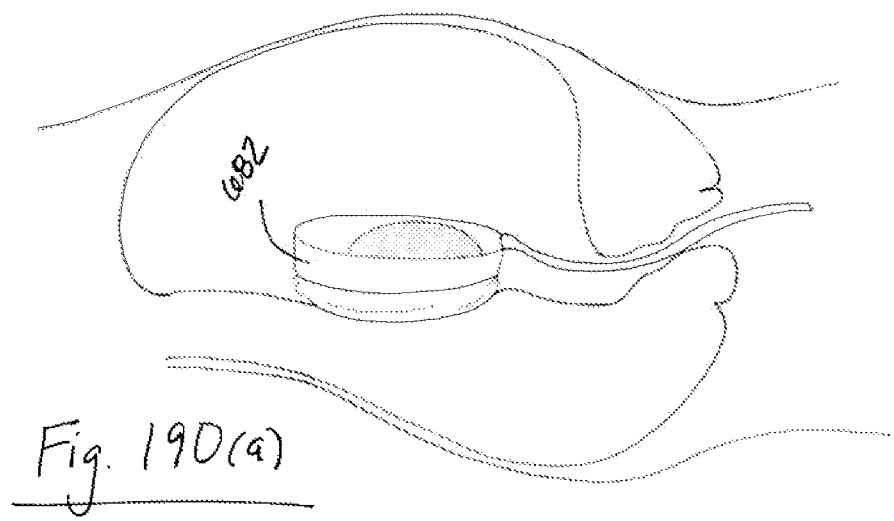
FIGS. 190(a) to 190(c) illustrate the use of a bag device in transvaginal procedures.
Figure 190B:
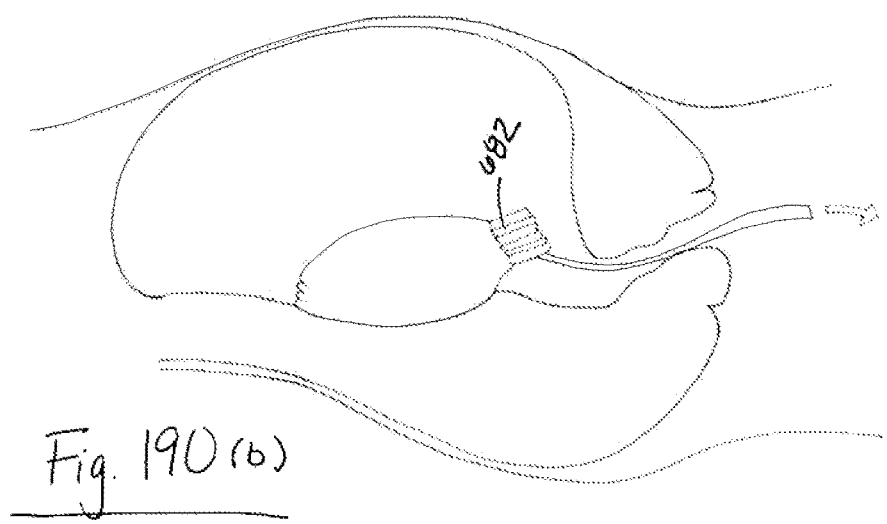
Figure 190C:
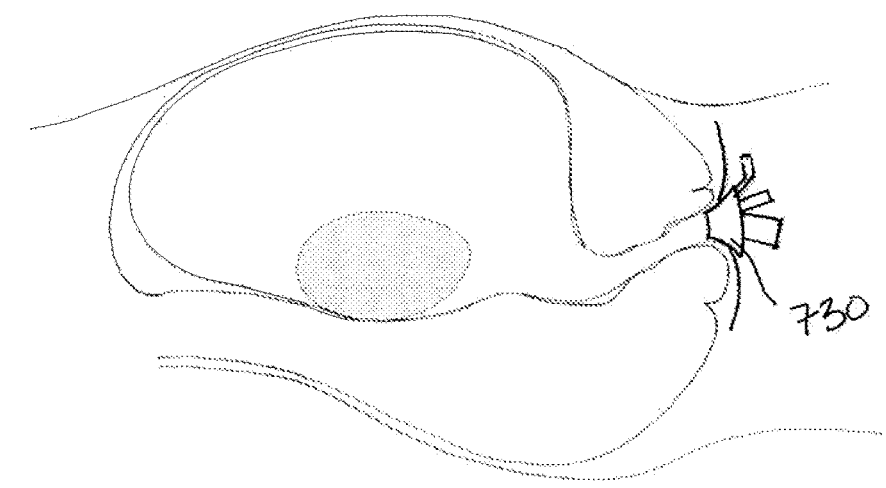

FIGS. 190(a) to 190(c) illustrate the use of the bag device of the invention in transvaginal procedures, for example hysterectomies. In some cases (FIGS. 190(a) and 190(b)) the bag device may be inserted and used directly without an access port. In other cases, the device may be used as described in other embodiments with an access port 730 (FIG. 190(c)).

Figure 191:
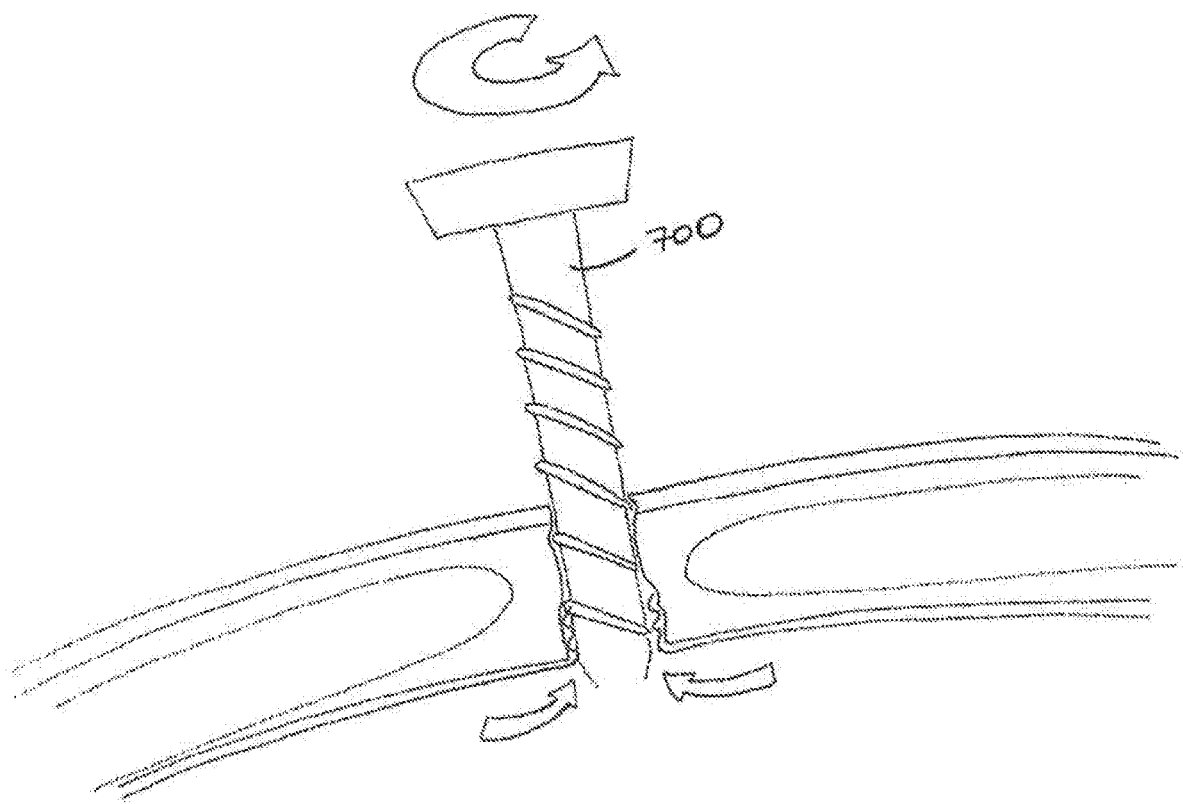
FIG. 191 is a view of a part of a bag with a threaded bung or trocar in place.

Referring to FIG. 191, in some cases the twisting action of a threaded trocar or bung 700 may assist in putting the bag up through the wound.

Figure 192A:
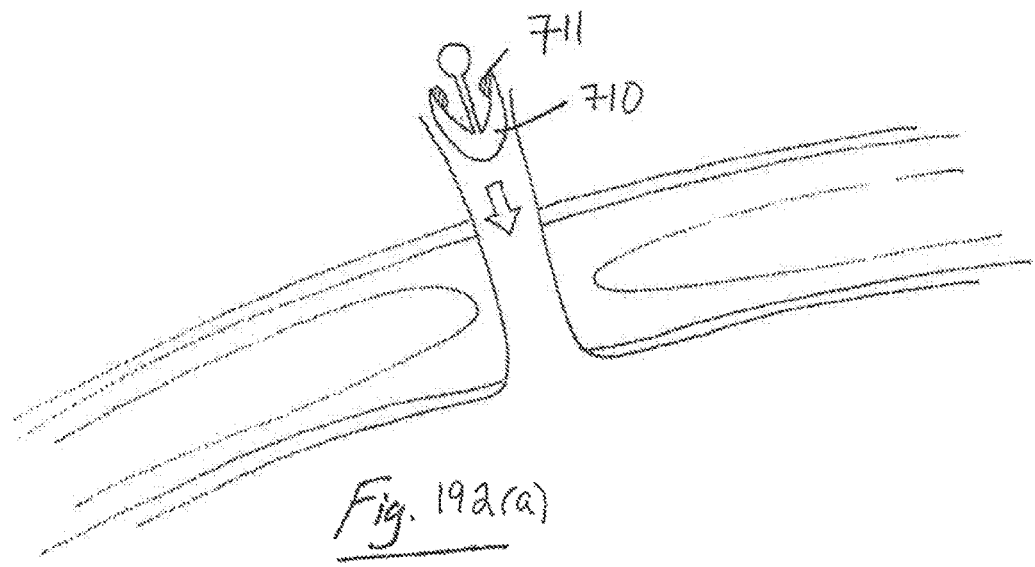
FIGS. 192(a) and 192(b) illustrate the closing of a chimney of a bag, prior to deflation.
Figure 192B:
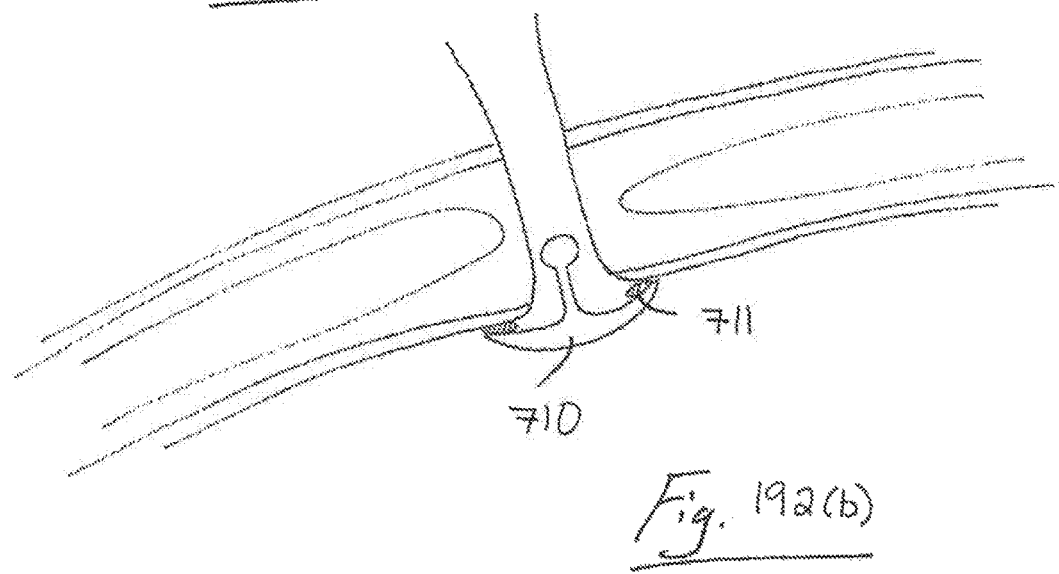

In some embodiments, in order to seal the hole into the chimney before the bag is deflated a closure device or valve may be deployed. For example, as illustrated in FIGS. 192(a) and 192(b) a closure device 710 may be inserted into the chimneys in a collapsed configuration and deployed at the distal end of the chimney. The closure device may be retained in place using any suitable retaining means such as an adhesive pad(s) 711.

Figure 193A:
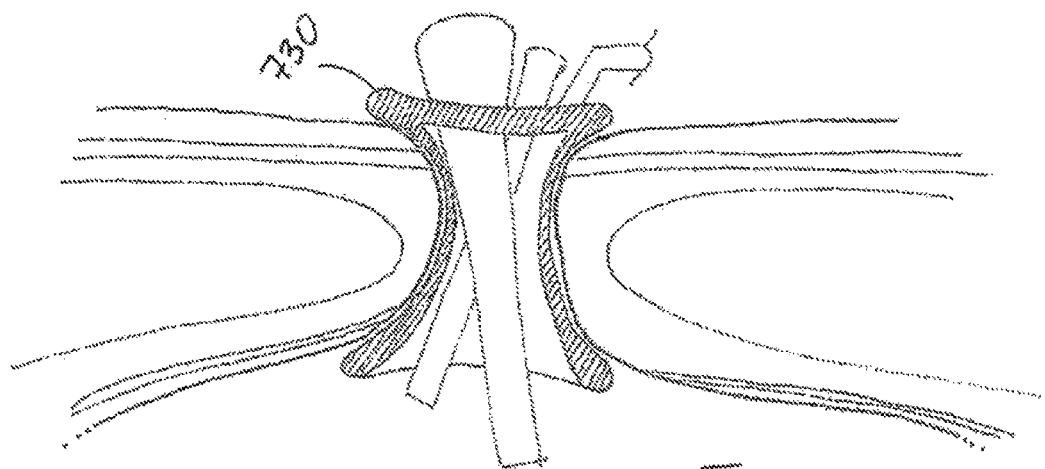
FIGS. 193(a) to 193(c) illustrate the use of the bag devices of the invention with various access devices.
Figure 193B:
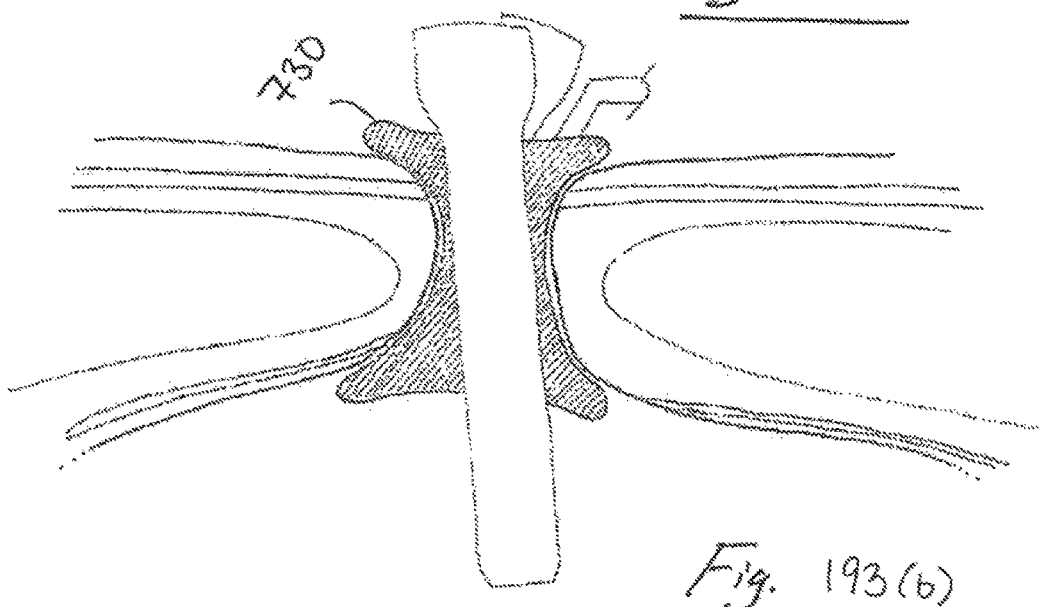
Figure 193C:
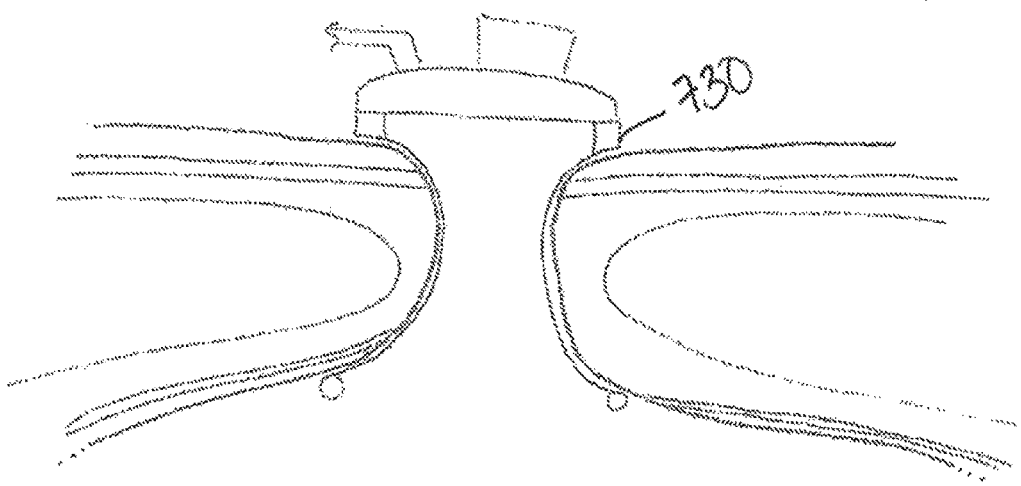

The abdominal bag device of the invention may be used with any suitable access port system 730 as illustrated, for example, in FIGS. 193(a) to 193(c). In some cases the access port is mounted within the neck of the bag.

Various features of the invention are described and illustrated. It will be appreciated that at least some of the features described in relation to one embodiment may be used not only in the embodiment specifically described but also in other appropriate embodiments. As used herein, the term "approximately" or "about" is understood to mean close in value or amount, but not precise. To the extent that such a definition for "approximate" or "about" is not considered sufficiently definite, approximate is understood to mean plus or minus 5% of the relevant parameter.

The invention is not limited to the embodiments hereinbefore described, with reference to the accompanying drawings, which may be varied in construction and detail.

The invention claimed is:

1. A method of performing a medical procedure, comprising:
    inserting a bag into a body cavity of a body through a first opening in the body;
    delivering excised tissue into an interior of the bag, wherein the excised tissue is delivered into the interior of the bag through a first opening of the bag;
    moving a portion of the bag from the body cavity to an exterior of the body via a second opening in the body;
    creating a second opening in a portion of the bag extending through the second opening in the body; and
    performing a procedure on the excised tissue in the interior of the bag, wherein performing the procedure includes accessing the interior of the bag via the first opening of the bag, accessing the interior of the bag via the second opening of the bag, and manipulating the excised tissue in the interior of the bag via at least one of the first and second openings.

2. The method of claim 1, further including insufflating the body cavity by introducing fluid into the body cavity to increase fluid pressure within the body cavity, wherein the tissue is excised with the body cavity in an insufflated state.

3. The method of claim 2, wherein the fluid pressure in the body cavity in the uninsufflated state of the body cavity is less than the fluid pressure in the body cavity in the insufflated state of the body cavity.

4. The method of claim 1, wherein the second opening is created by cutting the portion of the bag extending through the second body opening.

5. The method of claim 4, further comprising inserting one or more tools through a lumen of the trocar to access the excised tissue in the interior of the bag.

6. The method of claim 1, further comprising inserting a trocar into the second opening, wherein the trocar is configured to extend from the exterior of the body to the interior of the bag within the body cavity.

7. The method of claim 6, wherein the trocar includes a screw thread, and wherein the screw thread is configured to contact an interior surface of a channel extending from the second opening.

8. The method of claim 1, wherein accessing the interior of the bag includes accessing the interior of the bag through a wall of tissue that at least partially covers the body cavity.

9. The method of claim 1, wherein a first channel extends from the first opening of the bag, a second channel extends from the second opening of the bag, and wherein the first channel is configured to extend through the first opening in the body and the second channel is configured to extend through the second opening in the body.

10. The method of claim 9, wherein second channel includes the portion of the bag extending through the second opening.

11. The method of claim 9, further including expanding at least one of the first and second access channels from a collapsed state into an expanded state.

12. The method of claim 1, wherein manipulating the tissue includes cutting the tissue into pieces, and the method further includes removing the bag from the body cavity with pieces of the tissue remaining in the interior of the bag.

13. The method of claim 1, further comprising inflating the bag after the excised tissue is delivered into the interior of the bag and prior to creating the second opening, wherein inflating the bag urges an exterior surface of a portion of the bag that extends between the first opening and a location of the bag at which the second opening is formed, and connects the first opening to the second opening, against the interior surface of the body wall.

14. A method for performing a medical procedure, comprising:
 excising tissue within a working space in a body cavity with the body cavity in an insufflated state;
 inserting a bag into the working space;
 delivering the excised tissue into an interior of the bag;
 withdrawing a first access channel of the bag from the body cavity;
 withdrawing a second portion of the bag, different from a first portion of the bag forming the first access channel, from the body cavity; and
 forming an opening in the second portion of the bag to create a second access channel.

15. The method of claim 14, further comprising inflating the bag after the excised tissue is delivered into the interior of the bag, wherein inflating the bag urges an exterior surface of a portion of the bag that extends between the first access channel and a location on the bag in which the second access channel is formed, and connects the first access channel to the second access channel, against the interior surface of the body wall.

16. A method of performing a medical procedure, comprising:
 inserting a bag into a body cavity of a body through a first opening in the body;
 delivering excised tissue into an interior of the bag;
 moving a portion of the bag from the body cavity to an exterior of the body via a second opening in the body;
 inflation the bag within the body cavity;
 creating a second opening in a portion of the bag extending through the second opening in the body;
 inserting a trocar through the second opening; and
 performing a procedure on the excised tissue in the interior of the bag, wherein performing the procedure includes accessing the interior of the bag through via the first opening and the trocar.

17. The method of claim 16, wherein the trocar includes a screw thread, and wherein the screw thread is configured to contact an interior surface of a channel extending from the second opening.

18. The method of claim 16, wherein the trocar is configured to extend from the exterior of the body to the interior of the bag within the body cavity.

19. The method of claim 16, wherein the procedure is performed on the excised tissue when the bag is in an insufflated state, and the body cavity is in an uninsufflated state.

20. The method of claim 19, wherein fluid pressure within the portion of the bag in the insufflated state of the bag exceeds fluid pressure within the body cavity in the uninsufflated state of the body cavity.

* * * * *